(12) United States Patent
Groves et al.

(10) Patent No.: US 10,196,341 B2
(45) Date of Patent: Feb. 5, 2019

(54) C-HALOGEN BOND FORMATION

(75) Inventors: John T. Groves, Princeton, NJ (US);
Wei Liu, Plainsboro Township, NJ (US)

(73) Assignee: The Trustees Of Princeton University, Princeton, NJ (US)

( * ) Notice: Subject to any disclaimer, the term of this patent is extended or adjusted under 35 U.S.C. 154(b) by 0 days.

(21) Appl. No.: 14/239,706

(22) PCT Filed: Aug. 20, 2012

(86) PCT No.: PCT/US2012/051617
§ 371 (c)(1),
(2), (4) Date: May 19, 2014

(87) PCT Pub. No.: WO2013/081685
PCT Pub. Date: Jun. 6, 2013

(65) Prior Publication Data
US 2014/0249329 A1    Sep. 4, 2014

Related U.S. Application Data

(60) Provisional application No. 61/679,367, filed on Aug. 3, 2012, provisional application No. 61/639,523, filed on Apr. 27, 2012, provisional application No. 61/525,301, filed on Aug. 19, 2011.

(51) Int. Cl.
| | | |
|---|---|---|
| C07C 205/00 | (2006.01) | |
| C07C 67/307 | (2006.01) | |
| C07D 401/14 | (2006.01) | |
| C07B 39/00 | (2006.01) | |
| C07F 13/00 | (2006.01) | |
| C07C 17/35 | (2006.01) | |
| C07D 307/83 | (2006.01) | |
| C07F 5/02 | (2006.01) | |
| C07J 1/00 | (2006.01) | |
| C07C 17/06 | (2006.01) | |
| C07C 19/01 | (2006.01) | |
| C07C 22/00 | (2006.01) | |
| C07C 22/04 | (2006.01) | |
| C07C 22/08 | (2006.01) | |
| C07C 69/608 | (2006.01) | |
| C07C 231/12 | (2006.01) | |
| C07C 233/14 | (2006.01) | |

(52) U.S. Cl.
CPC ............ *C07C 67/307* (2013.01); *C07B 39/00* (2013.01); *C07C 17/06* (2013.01); *C07C 17/35* (2013.01); *C07C 19/01* (2013.01); *C07C 22/00* (2013.01); *C07C 22/04* (2013.01); *C07C 22/08* (2013.01); *C07C 69/608* (2013.01); *C07C 231/12* (2013.01); *C07C 233/14* (2013.01); *C07D 307/83* (2013.01); *C07D 401/14* (2013.01); *C07F 5/025* (2013.01); *C07F 13/00* (2013.01); *C07J 1/0011* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 3,749,672 A * | 7/1973 | Golton | C02F 1/50 210/756 |
| 2007/0093495 A1 | 4/2007 | Ruggero et al. | |
| 2007/0276024 A1 | 11/2007 | Bond | |
| 2008/0292534 A1 | 11/2008 | Richardson et al. | |
| 2009/0209010 A1 | 8/2009 | Fasan et al. | |
| 2010/0152502 A1 | 6/2010 | Caires et al. | |
| 2010/0233086 A1 | 9/2010 | Lehmann et al. | |

FOREIGN PATENT DOCUMENTS

| | | |
|---|---|---|
| WO | 9903802 | 1/1999 |
| WO | 09052970 | 4/2009 |
| WO | 2013/028639 A1 | 2/2013 |

OTHER PUBLICATIONS

Maugh, Science. 1979, (4422), 1058.*
Tabushi et al. Tetrahedron Lett, 38, 1979, 3681-3684.*
Qerci et al., "Nickel (salen) catalysed chlorination of saturated hydrocarbons by sodium hypochlorite," tetrahedron Lett, (1990) 31(45):6577-6580.
Brown et al., "Catalytic Homogeneous Functionalization of Adamantane. Influence of Electronic and Structural Features of the Metalloporphyrin catalyst on Atom Transfer Selectivity (Oxygenation versus Azidification/Halogenation)," J. Org. Chem (1988) 53:5762-5768.
Hill et al., Catalytic Replacement of Unactivated Alkane Carbon-Hydrogen Bonds with Carbon-X Bonds (X=Nitrogen, Oxygen, Chlorine, Bromine, or Iodine). Coupling of Intermoleuclar Hydrocarbon Activation by MnIIITPPX Complexes with Phase-Transfer Catalysis, J. Org. Chem (1983) 48:3277-3281.
Dermiek et al., "Darstellung von Primaren Alkylfluoriden Unter Einsatz Der Phasen Transfer Katalyse," Journal of Fluorine Chemistry, (1983) 22:431-437.
Olah et al., "Synthetic Methods and Reactions; 1101. fluorination of 1-Haloadamantanes and -diamantane with Nitronium Tetrafluoroborate/ Pyridine Polyhydrogen Floride or Sodium Nitrate/Pyridine Polyhydrogen Fluoride," Communications (1983) pp. 713-715.
Lee et al., "Selective electrolytic fluorinations in 70% HF/30% pyridine," Journal of Fluorine Chemistry (1996) 77:65-70.

(Continued)

Primary Examiner — Ana Z Muresan
(74) Attorney, Agent, or Firm — Volpe and Koenig, P.C.

(57) ABSTRACT

Methods of halogenating a carbon containing compound having an sp3 C—H bond are provided. Methods of fluorinating a carbon containing compound comprising halogenation with Cl or Br followed by nucleophilic substitution with F are provided. Methods of direct oxidative C—H fluorination of a carbon containing compound having an sp3 C—H bond are provided. The halogenated products of the methods are provided.

43 Claims, 56 Drawing Sheets

(56) References Cited

OTHER PUBLICATIONS

Kitamura et al., "A Practical and Convenient Fluorination of 1,3-Dicarbonyl compounds Using Aqueous HF in the Presence of Iodosylbenzene," Organic Letters (2011) 13(9):2392-2394.

Reddy et al., "A DBFOX-Ph-Based Combinatorial Catalyst for Enantioselective Fluorination of Aryl Acetyl and 3- Butenoyl Thiazolidinoes," Chemistry, an Asian Journal (2009) 4:1411-1415.

Beeson et al., "Enantioselective Organocatalytic a-Fluorination of Adelhydes," J. Am. Chem. Soc. (2005) 127:8826-8828.

Slaugher et al., "Radical Autoxidation and Autogenous O2 Evolution in Manganese-Porphyrin Catalyzed Alkane Dxidations with Chlorite," Inorganic Chemistry, vol. 43, No. 17, 2004, pp. 5198-5204.

Meunier et al., "Mechanism of Oxidation Reactions Catalyzed by Cytochrome P450 Enzymes," Chem. Rev. 2004, 104, 3947-3980.

Tang et al., "Silver-Catalyzed Late-Stage Fluorination," J. Am. Chem. Soc. 2010, 132, 12150-12154.

Liu et al., "Manganese Porphyrins Catalyze Selective C—H Bond Halogenations," J. Am. Chem. Soc. 2010, 132, 12847-12849.

Kurahashi et al., "Trigonal-Bipyramidal Geometry Induced by an External Water Ligand in a Sterically Hindered Iron Salen Complex, Related to the Active Site of Protocatechuate 3,4-Dioxygenase," Inorganic Chemistry, vol. 45, No. 19, 2006, 7709-7721.

Liu et al., "Manganese-Catalyzed Oxidative Benzylic C—H Fluorination by Fluoride Ions," Angew. Chem. Int. Ed. 2013, 52, 6024-6027.

DePoorter et al., "Catalytic Hydroxylation of Saturated Hydrocarbons with the Sodium Hypohalite/Manganese Prophyrin System," Journal of Molecular Catalysis, 31 (1985) 221-224.

Hill et al., "Alkane Activation and Functionalization under Mild Conditions by a Homogeneous Manganese (III) Porphyrin-Iodosylbenzene Oxidizing System," J. Am. Chem. Soc. 1980, 102, 6374-6375.

Prokop et al., "Unprecedented Rate Enhancements of Hydrogen-Atom Transfer to a Manganese (V)-Oxo Corrolazine Complex," Angew. Chem. Int. Ed. 2010, 49, 5091-5095.

Mirkhani et al., "Polystyrene-bound 1,4-phenylenediamine as a heterogeneous axial ligand for Mn(salophen)Cl and its use as biomimetic alkene epoxidation and alkane hydroxylation catalyst with sodium periodate.," Polyhedron 25 (2006) 2904-2914.

Kurahashi et al., "Critical Role of External Axial Ligands in Chirality Amplification of trans-Cyclohexane-1,2-diamine in Salen Complexes," J. Am. Chem. Soc. 2009, 131, 12394-12405.

Liu, W. And Groves, J. "Manganese Catalyzed C—H Halogenation" (2015) Acc. Chem. Res. 48: 1727-1735.

Chen et al. "Mechanochemical unzipping of insulating polyladderene to semiconducting polyacetylene" (2017) Science 357: 475-479, 480.

Tabushi, I. and Koga, N., "Synergetic Combination of Catalysis of the Phase Transfer-Electron Transfer Type for the Oxidation of Alcohols or Hydrocarbons" (1979) Tetrahedron Letters (38) 3681-3684.

\* cited by examiner

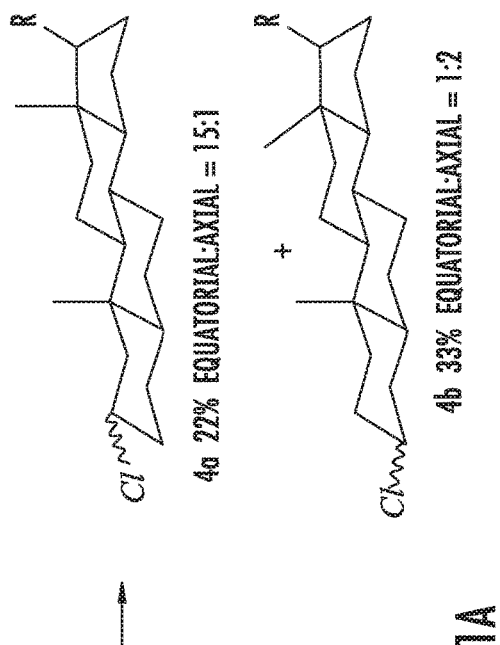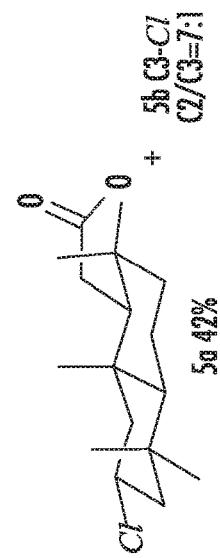
FIG. 1A
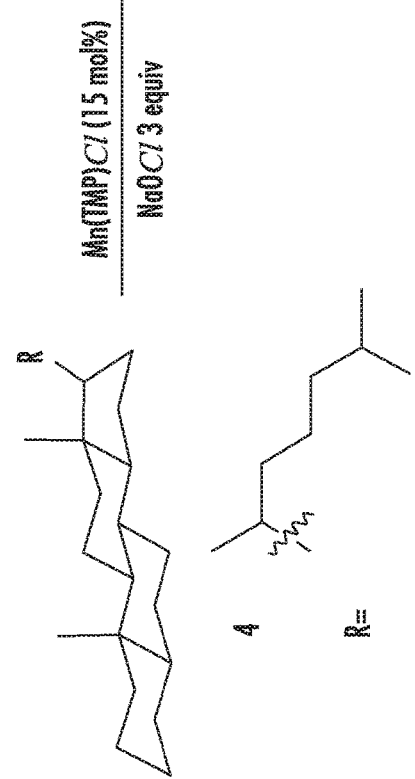
FIG. 1B

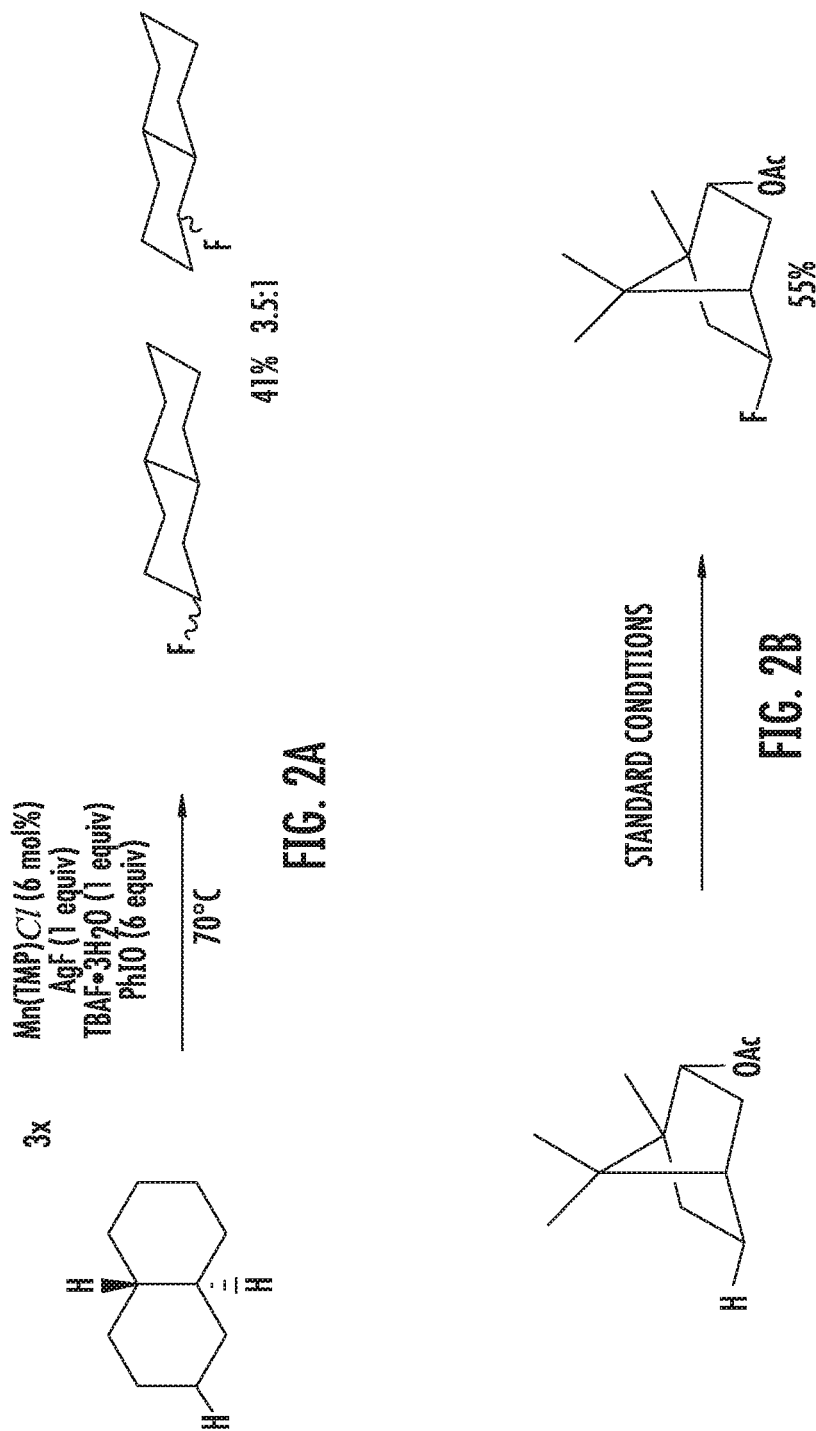

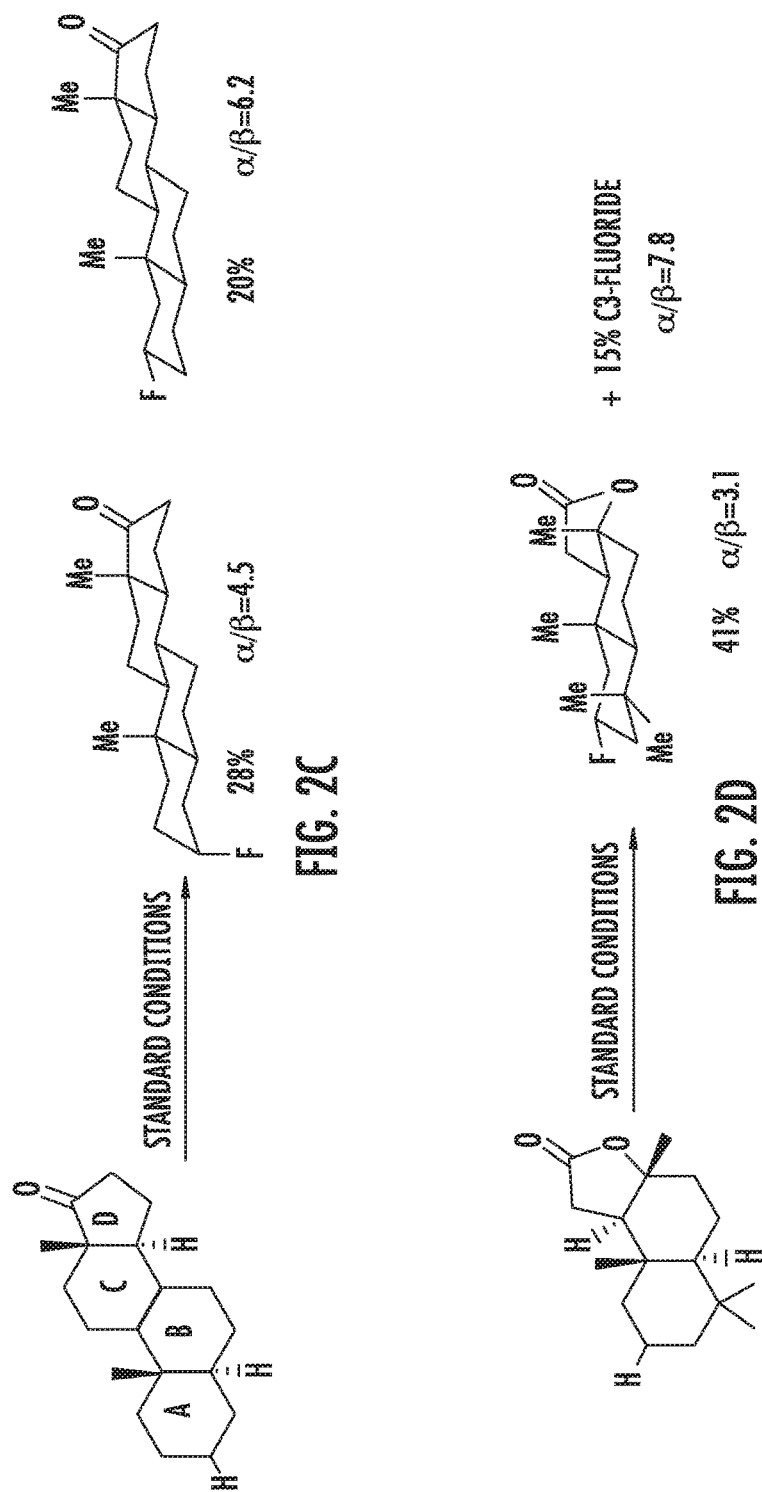

$Mn^{IV}(TMP)F_2$

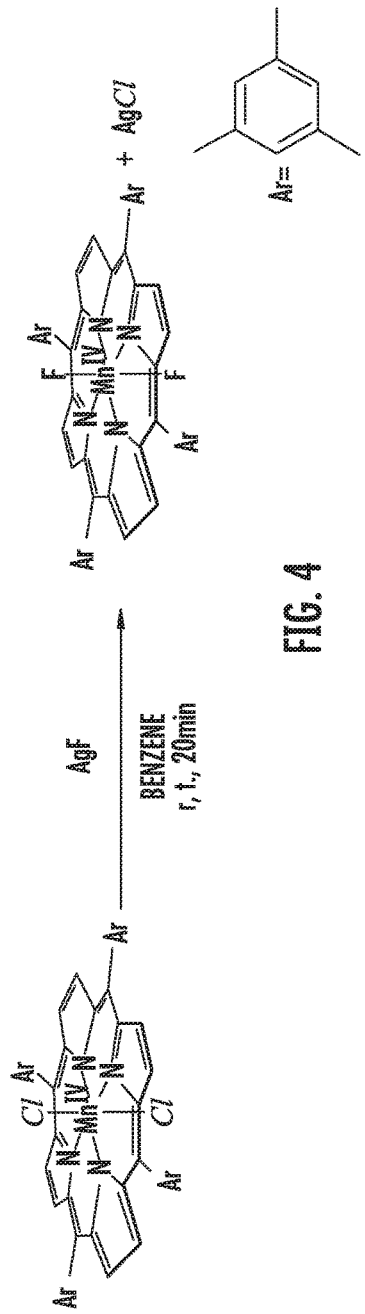

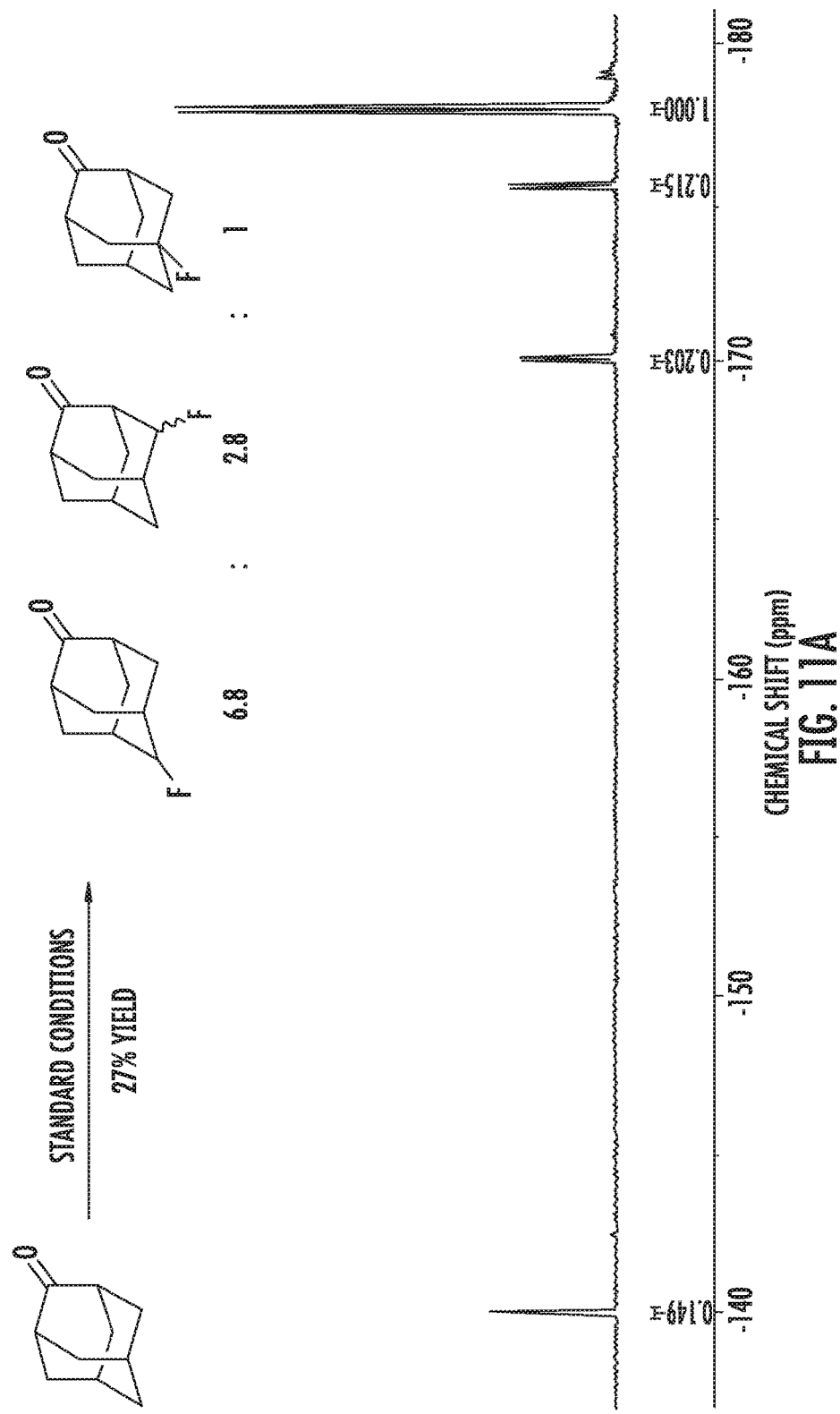

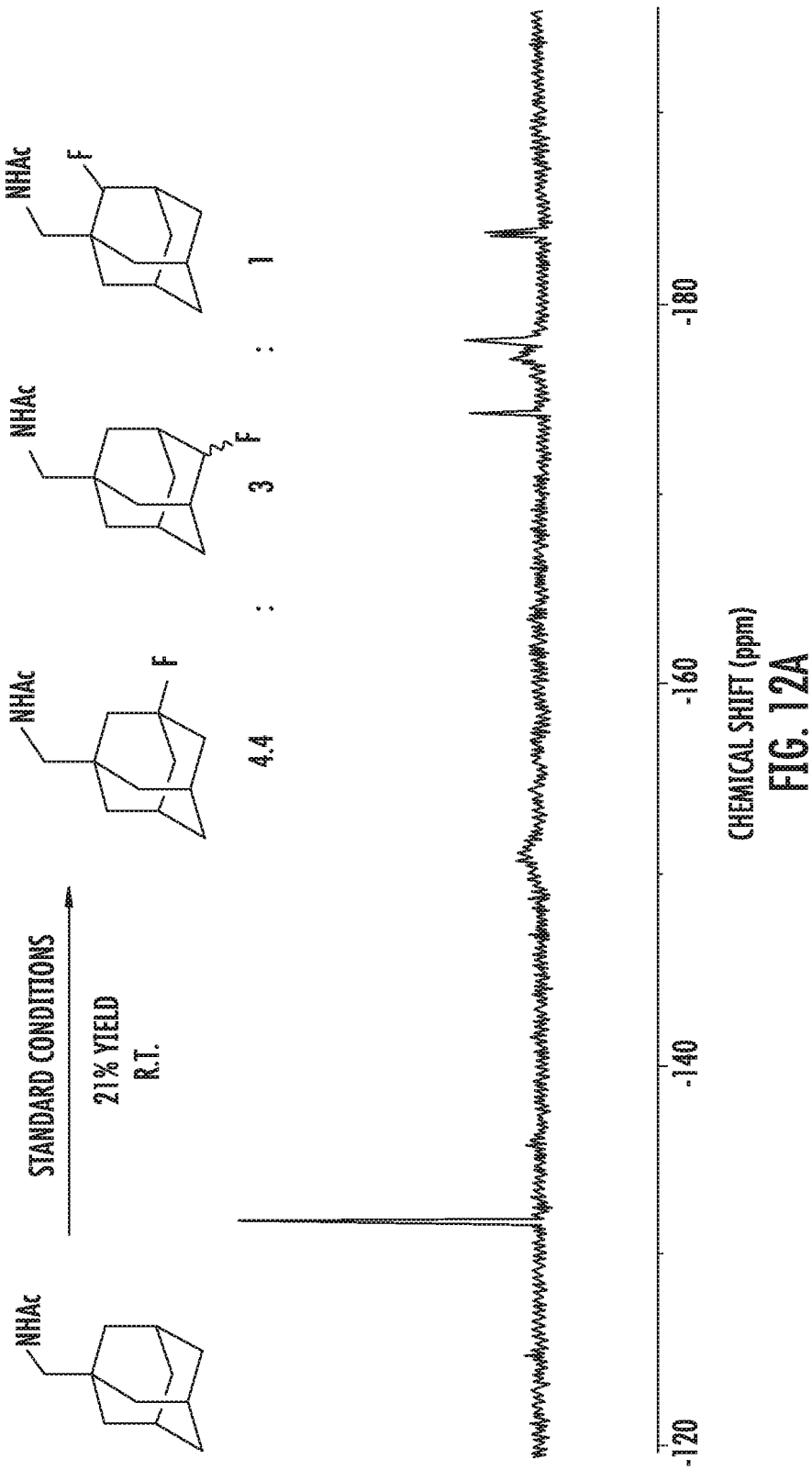

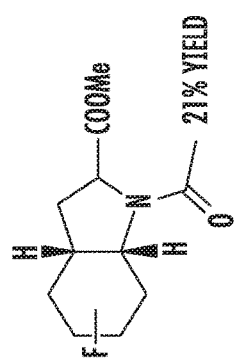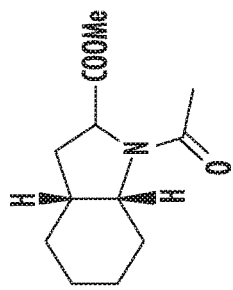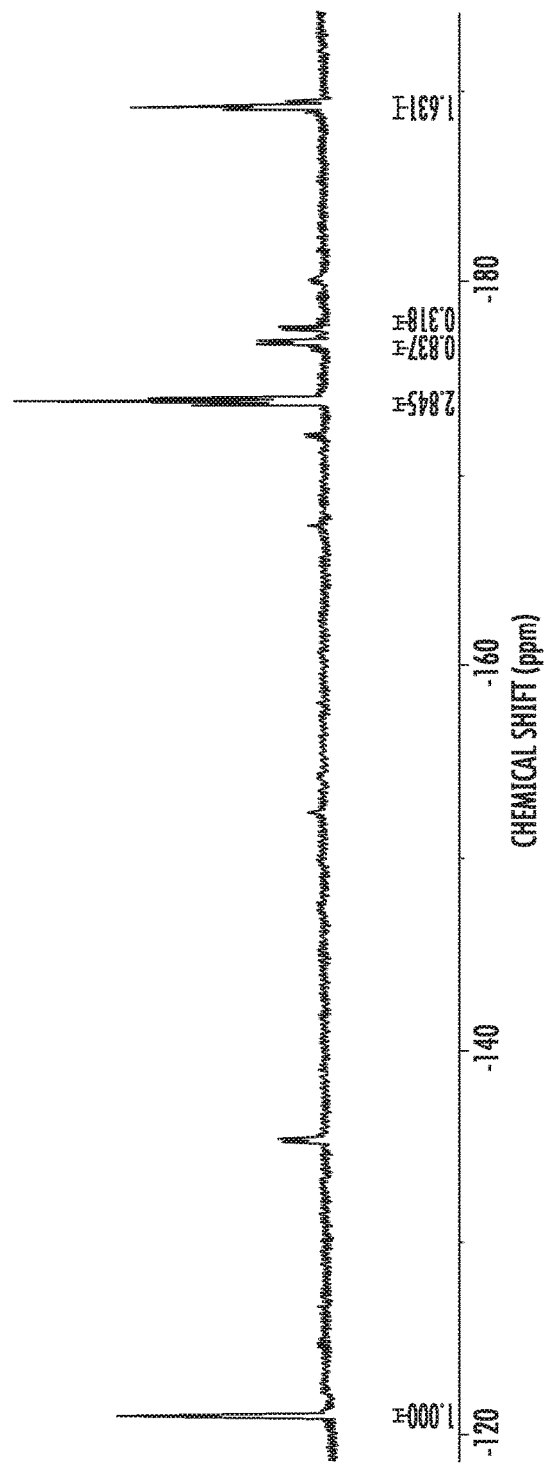
FIG. 14A

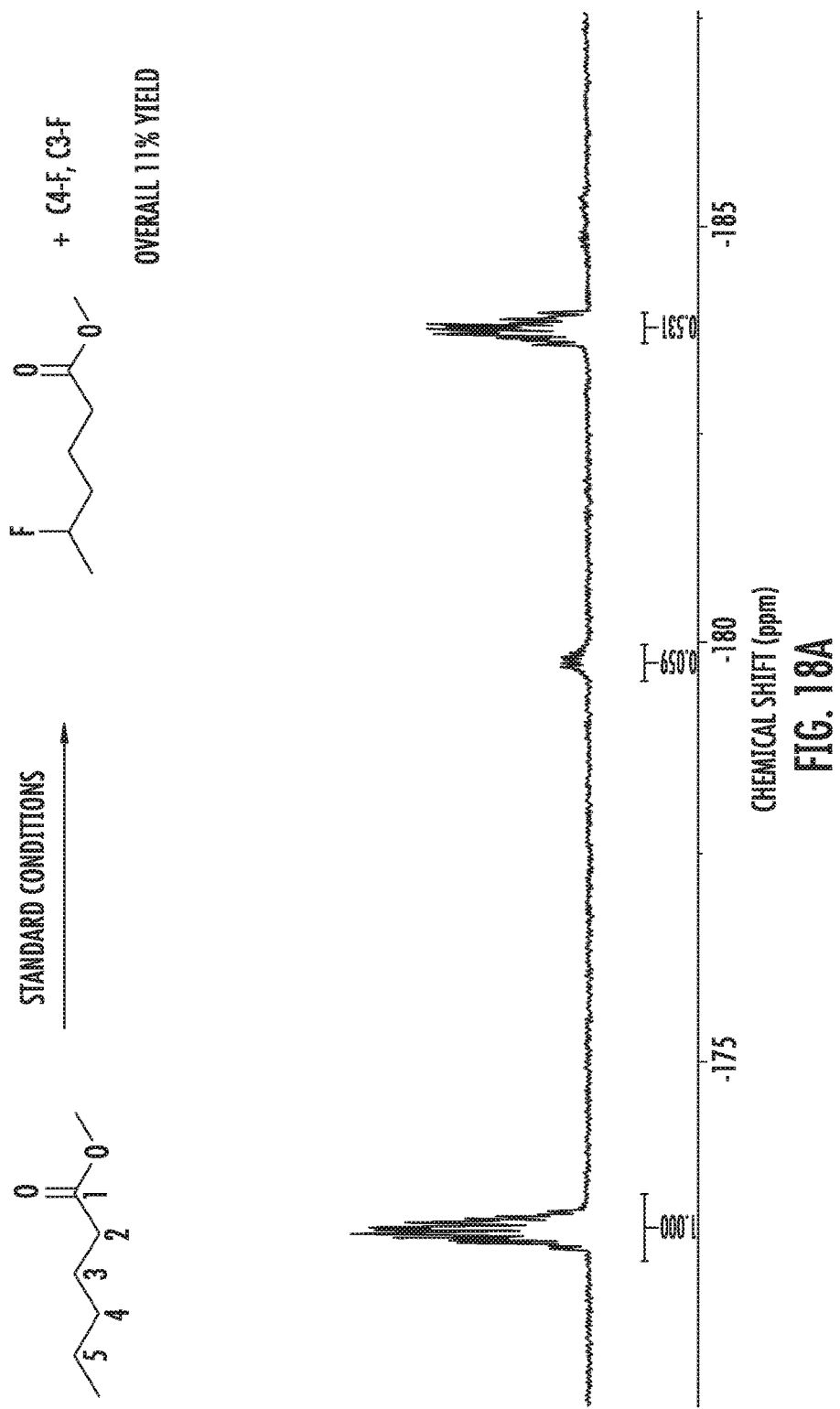

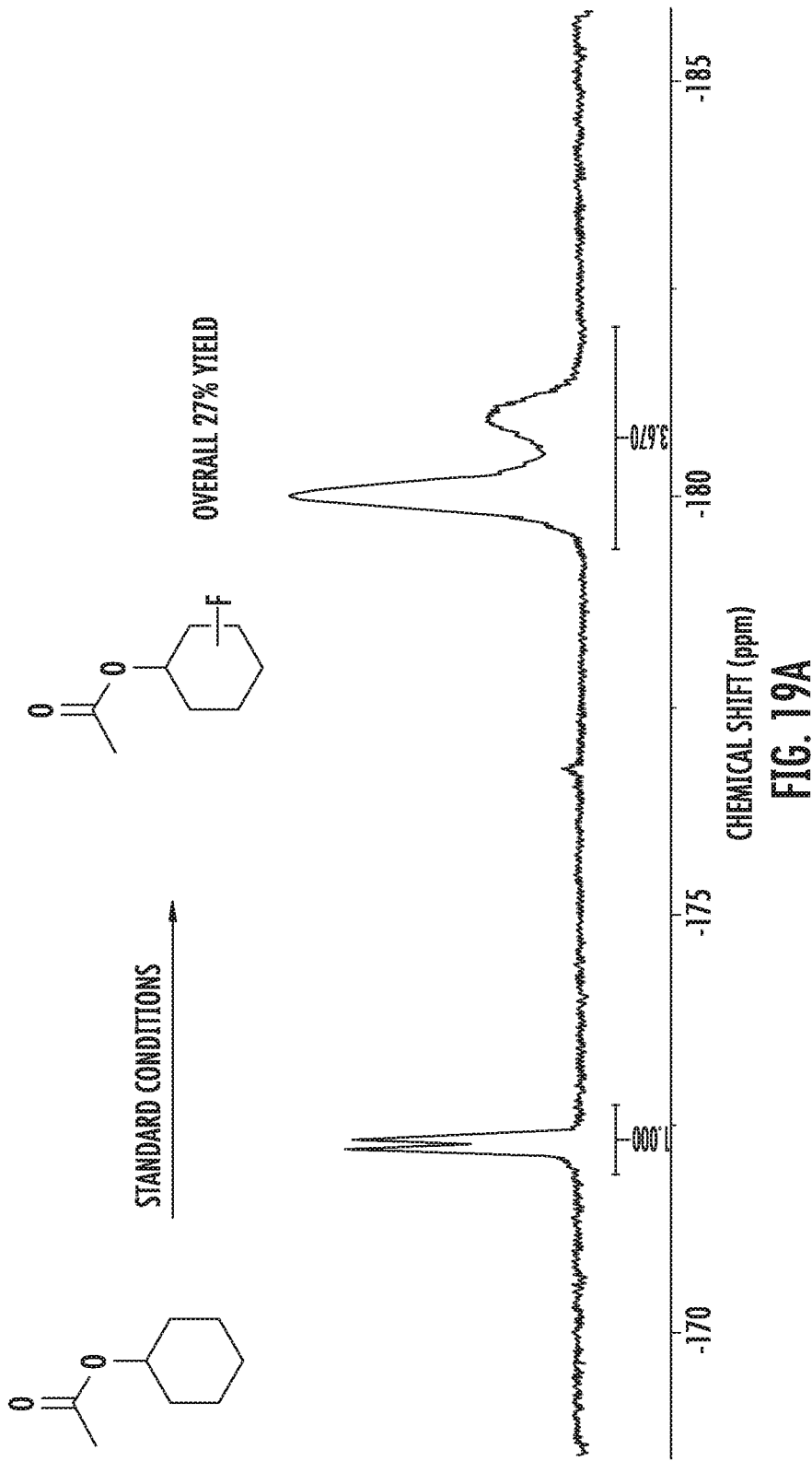

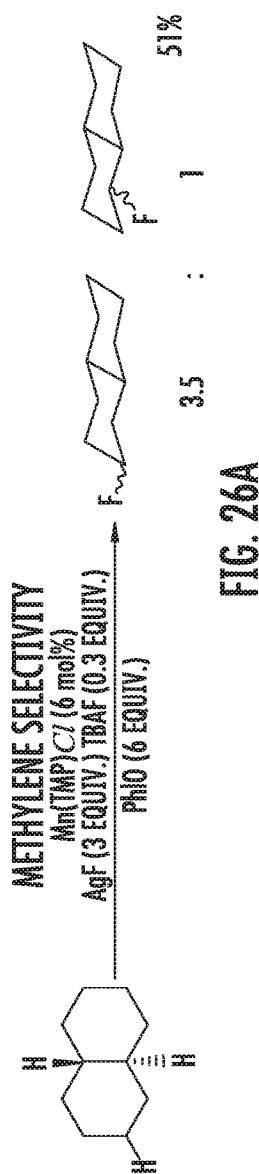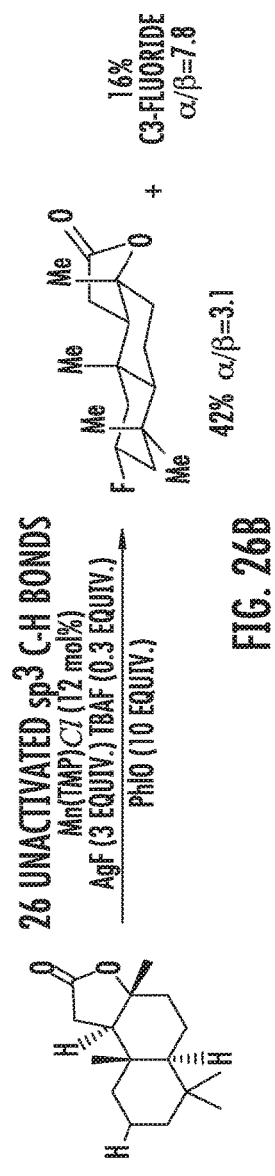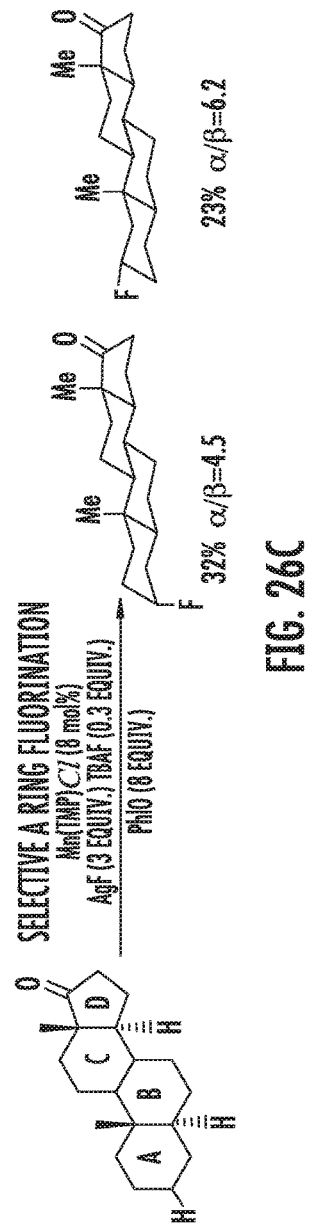
FIG. 26A
FIG. 26B
FIG. 26C

C-HALOGEN BOND FORMATION

This application is a 35 U.S.C. § 371 national stage application of PCT/US2012/051617, filed Aug. 20, 2012, claims the benefit of U.S. Provisional Application No. 61/525,301, filed Aug. 19, 2011, U.S. Provisional Application No. 61/639,523, filed Apr. 27, 2012, and U.S. Provisional Application No. 61/679,367, filed Aug. 3, 2012, all of which are incorporated herein by reference as if fully set forth.

This invention was made with government support under Grants No. CHE-0616633 and CHE-1148597 awarded by the National Science Foundation and with support from the Center for Catalytic Hydrocarbon Functionalization, an Energy Frontier Research Center funded by the U.S. Department of Energy, Office of Science, Office of Basic Energy Sciences under Award No. DE-SC0001298. The government has certain rights in this invention.

FIELD

The disclosure relates to halogenation of carbon containing compounds and the products of halogenation.

BACKGROUND

Halogenated organic compounds play a central role in organic chemistry, affording important components of a variety of biologically active molecules as well as pharmacologically active agents. Alkyl chlorides also find widespread use as intermediates in organic synthesis, as in cross-coupling reactions.

Manganese porphyrins and Schiff base complexes have long been known to be effective catalysts for the oxygenation of both unsaturated and saturated hydrocarbons. Nearly all of the advances in the field dealt with oxygenation reactions, particularly olefin epoxidation and alkane hydroxylation. Small amounts of halogenation were described in the original reports. However, most of these reactions resulted in poor selectivity for non-oxygen functionalization, since competitive oxygenation of substrates remains the main reaction. High selectivity of chlorination has been reported by Ricci et al. in the nickel(salen)/hypochlorite system, but the substrate scope was limited and the reaction was likely propagated by chloroxy radical. (Querci, C.; Strologo, S.; Ricci, M. Tetrahedron Lett. 1990, 31, 6577-6580, which is incorporated herein by reference as if fully set forth). There are at present few if any ways to incorporate halogen atoms selectively into complex compounds.

Nature has found highly selective ways to transform aliphatic C—H bonds into alcohols, halides and olefins using reactive metal-oxo intermediates within enzymes. A notable exception is aliphatic fluorination, for which there are no known biochemical precedents. There are also no direct ways to convert unreactive $sp^3$ C—H bonds into C—F bonds through chemical catalysis.

Although strategies for aromatic C—H fluorination developed over the past five years have provided novel and unprecedented access to complex aryl fluorides, (Furuya, T.; Kamlet, A. S.; Ritter, T., Catalysis for Fluorination and Trifluoromethylation Nature 2011, 473, 470-477; P. P. Tang, T. Furuya, T. Ritter, *J Am Chem Soc* 132, 12150 (2010); and D. A. Watson et al. *Science* 325, 1661 (2009), which are incorporated herein by reference as if fully set forth) there is a notable lack of recent progress for the catalytic fluorination of aliphatic C—H bonds (P. Herrmann, J. Kvicala, V. Pouzar, H. Chodounska, *Collect Czech Chem C* 73, 1825 (2008); and Rozen, S.; Gal, C., Activating Unreactive Sites of Organic-Molecules Using Elemental Fluorine, J. Org. Chem. 1987, 52, 2769-2779, which are incorporated herein by reference as if fully set forth). Traditional methods for introducing fluorine into a saturated framework require harsh conditions and highly toxic fluorine sources, such as elemental fluorine, that require specialized equipment and are not compatible with many typical substituents and functional groups (R. D. Chambers, A. M. Kenwright, M. Parsons, G. Sandford, J. S. Moilliet, *J Chem Soc Perk T* 1, 2190 (2002); S. Rozen. *Eur. J. Org. Chem.*, 2433 (2005); and S. Rozen. *Acc. Chem. Res.* 38, 803 (2005), which are incorporated herein by reference as if fully set forth). Metal catalyzed direct benzylic C—H fluorination has been achieved recently with palladium catalysts and a source of "F+" (K. L. Hull, W. Q. Anani, M. S. Sanford. *J. Am. Chem. Soc.* 128, 7134 (2006); X. S. Wang, T. S. Mei, J. Q. Yu. *J. Am. Chem. Soc.* 131, 7520 (2009); T. D. Beeson, D. W. C. MacMillan. *J. Am. Chem. Soc.* 127, 8826 (2005), which are incorporated herein by reference as if fully set forth). Also, advances in the field of enantioselective organocatalytic fluorination have been reported that are capable of introducing a fluorine atom adjacent to a carbonyl group (T. D. Beeson, D. W. C. MacMillan. *J. Am. Chem. Soc.* 127, 8826 (2005), which is incorporated herein by reference as if fully set forth) and via the ring-opening of epoxides with a fluoride nucleophile (J. A. Kalow, A. G. Doyle. *J. Am. Chem. Soc.* 132, 3268 (2010), which is incorporated herein by reference as if fully set forth). A chemo-enzymatic fluorination strategy via initial P450-mediated hydroxylation (R. Fasan, A. Rentmeister, F. H. Arnold. *Nat. Chem. Biol.* 5, 26 (2009), which is incorporated herein by reference as if fully set forth) and a stoichiometric chemical route involving initial decarboxylation (M. Rueda-Becerril et al. *J. Am. Chem. Soc.* 134, ASAP (2012), which is incorporated herein by reference as if fully set forth) have also been reported. Despite this impressive progress, a method for the selective and efficient incorporation of fluorine at unactivated C—H sites within a target molecule is singularly absent in the repertoire of chemical synthesis.

SUMMARY

In an aspect, the invention relates to a method of halogenating a carbon containing compound having an sp3 C—H bond. The method comprises combining a carbon containing compound, a halogenating agent, a halogenating catalyst, and a phase transfer catalyst.

In an aspect, the invention relates to a method of fluorinating a carbon containing compound having an sp3 C—H bond. The method comprises combining a carbon containing compound, a halogenating agent, a halogenating catalyst, and a phase transfer catalyst, obtaining a halogenated product, and conducting nucleophilic substitution on the halogenated product with a fluorine source.

In an aspect, the invention relates to a composition comprising at least two or more of a carbon containing compound having an sp3 C—H bond hydrogen, a halogenating agent, a halogenating catalyst, or a phase transfer catalyst.

In an aspect, the invention relates to a composition comprising an organic compound with a halogen in place of an sp3 C—H bond.

In an aspect, the invention relates to a kit comprising one or more container. Each container includes at least one reactant for a halogenation reaction selected from the group consisting of a carbon containing compound, a halogenating agent, a halogenating catalyst, or a phase transfer catalyst. The composition in each container includes at least one fewer substance than required to make a halogenation reaction proceed.

In an aspect, the invention relates to a composition comprising a product of a method of halogenating a carbon containing compound having an sp3 C—H bond comprising combining the carbon containing compound, a halogenating agent, a halogenating catalyst, and a phase transfer catalyst. The carbon containing compound may be but is not limited to neopentane; toluene; cyclohexane; norcarane; trans-decalin; 5α-cholestane; sclareolide; 1,3,5(10)-estratrien-17-one; (1R,4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholestane; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R,4aS,8aS)-5,5,8a-trimethyl-1-(3-oxobutyl)octahydronaphthalen-2(1H)-one; phenylalanine; donepezil precursor; amphetamine; δ-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; cyclohexane carboxylic acid methyl ester; or an analog thereof.

In an aspect, the invention relates to a composition comprising a product of a method of fluorinating a carbon containing compound having an sp3 C—H bond comprising combining the carbon containing compound, a halogenating agent, a halogenating catalyst, and a phase transfer catalyst, obtaining a halogenated product, and conducting nucleophilic substitution on the halogenated product with a fluorine source. The carbon containing compound may be but is not limited to neopentane; toluene; cyclohexane; norcarane; trans-decalin; 5α-cholestane; sclareolide; 1,3,5(10)-estratrien-17-one; (1R,4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholestane; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R,4aS,8aS)-5,5,8a-trimethyl-1-(3-oxobutyl)octahydronaphthalen-2(1H)-one; phenylalanine; donepezil precursor; amphetamine; δ-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; cyclohexane carboxylic acid methyl ester; or an analog thereof.

BRIEF DESCRIPTION OF THE DRAWINGS

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIGS. 1A-1B illustrate halogenation of complex substrates. FIG. 1A illustrates steric effects that may lead to selective chlorination of 5α-cholestane at the C2 and C3 positions. NMR yields shown. FIG. 1B illustrates C2-selective chlorination of sclareolide. Isolated yield shown.

FIGS. 2A-2D illustrate manganese porphyrin catalyzed selective C—H fluorination of complex molecules. In FIG. 2A, fluorination of trans-decalin gave predominantly (41%) methylene fluorination. In FIG. 2B, steric and electronic effects lead to selective 5-exo-fluorination of bornyl-acetate (55%). In FIG. 2C, steric effects on 5α-androstan-17-one lead to selective ring A fluorination (48%). In FIG. 2D, selective fluorination of sclareolide is illustrated.

FIGS. 3A-3D: FIG. 3A illustrates a proposed catalytic cycle for a manganese porphyrin catalyzed C—H fluorination reaction. FIG. 3B illustrates inferred stereoelectronics for hydrogen abstraction. FIG. 3C illustrates the molecular structure of trans-Mn$^{IV}$(TMP)F$_2$ drawn at 50% probability of the electron density. FIG. 3D illustrates selected bond lengths and angles of trans-Mn$^{IV}$(TMP)F$_2$.

FIG. 4 illustrates synthesis of trans-Mn$^{IV}$(TMP)F$_2$.

FIG. 5A illustrates the UV-vis spectrum of trans-Mn$^{IV}$(TMP)F$_2$. FIG. 5B illustrates experimental (top) and simulated (bottom) EPR spectra of trans-Mn$^{IV}$(TMP)F$_2$ (Detail parameters: X-band EPR (9.453 GHz) using 50/50 v/v toluene/CH$_2$Cl$_2$ glasses at 10K. Modulation frequency 100 kHz, modulation amplitude 12.5 G, time constant 163.84 ms, scan time 335 s, microwave power 15.9 mW, and spectrometer gain 10000).

FIG. 7A illustrates the product of buspirone precursor fluorination. FIG. 7B illustrates that fluorination of buspirone precursor affords fluorinated product with another unknown product. FIG. 7C illustrates the mass spectrum of the fluorinated buspirone peak. FIG. 7D illustrates the mass spectrum of the buspirone precursor starting material.

FIGS. 11A-11B illustrate fluorination of 2-adamantanone.

FIGS. 12A-12B illustrate fluorination of rimantadine analogue.

FIGS. 14A-14B illustrate fluorination of perindopril precursor.

FIGS. 18A-18C illustrate fluorination of methyl hexanoate.

FIGS. 19A-19C illustrate fluorination of cyclohexyl acetate.

FIG. 23A illustrates a porphyrin. FIG. 23B illustrates phthalocyanine. FIG. 23C illustrates a porphyrazine. FIG. 23D illustrates tetra-N-methyl-tetra-2-pyridoporphyrazine.

FIG. 24A illustrates N-Pyridylmethyl-tri-aza-cyclononane. FIG. 24B illustrates N,N-Dipyridylmethyl cyclohexadiamine. FIG. 24C illustrates tetra-aza-cyclotetra-decane. FIG. 24D illustrates N,N-dipyridylmethyl 2,2'-dipyrrolidine. FIG. 24E illustrates N,N-dipyridylmethyl ethylenediamine. FIG. 24F illustrates tripyridyl amine (TPA). FIG. 24G illustrates salen.

FIGS. 26A-26D illustrate manganese porphyrin catalyzed selective C—H fluorinations. FIG. 26A illustrates methylene-selective fluorination of trans-decalin. FIG. 26B illustrates selective fluorination of sclareolide. FIG. 26C illustrates selective A ring fluorination of 5α-androstan-17-one. FIG. 26D illustrates selective 5-exo-fluorination of bornyl-acetate.

DETAILED DESCRIPTION OF THE PREFERRED EMBODIMENTS

Figure 3A:
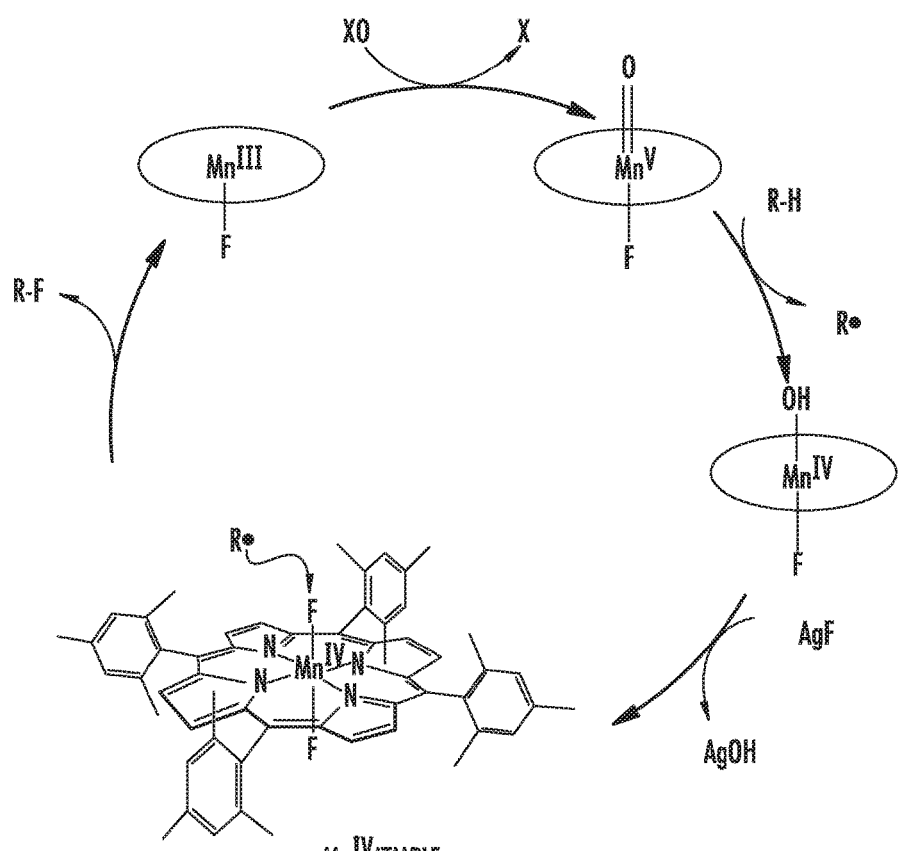

Certain terminology is used in the following description for convenience only and is not limiting. The words "a" and "one," as used in the claims and in the corresponding portions of the specification, are defined as including one or more of the referenced item unless specifically stated otherwise. The phrase "at least one" followed by a list of two or more items, such as "A, B, or C," means any individual one of A, B or C as well as any combination thereof.

Porphyrin catalysts and methods of use thereof are discussed in U.S. Publication No. 2011/0306584; U.S. Publication No. 20100093688; U.S. Pat. No. 6,969,707; U.S. Pat. No. 6,448,239; U.S. Pat. No. 6,002,026; and PCT/US2011/48396, which are incorporated herein by reference as if fully set forth. The embodiments described herein extend the knowledge of porphyrin catalysts and methods of use thereof. One or more of the porphyrin catalysts in U.S. Publication No. 2011/0306584; U.S. Publication No. 20100093688; U.S. Pat. No. 6,969,707; U.S. Pat. No. 6,448,239; U.S. Pat. No. 6,002,026; and PCT/US2011/48396 may be utilized in an embodiment herein as a halogenating catalyst or a fluorinating catalyst.

Methods of halogenating carbon containing compounds are provided herein. An embodiment provides a method of halogenating a carbon containing compound comprising reacting a carbon containing compound with a halogenating agent in the presence of a halogenating catalyst and a phase transfer catalyst. A non-limiting example follows: Under a nitrogen atmosphere, 2 mL sodium hypochlorite (0.33 M) was added to a solution of Mn(TMP)Cl (0.033 mmol), tetrabutylammonium chloride (TBACl, 0.027 mmol), and substrate (0.22 mmol) in 1 mL dichloromethane in a 4 mL sealed vial. The biphasic mixture was stirred smoothly under nitrogen. The reaction was monitored by GC/MS or TLC and additional sodium hypochlorite solution is added under nitrogen if the conversion of the substrate is low. The product was purified by flash column chromatography. The amount of hypochlorite could be 1-10 equivalents based on substrate or any specific amount within this range. The halogenating catalyst could be 1-20 mol %, 5-15 mol %, or any specific amount within these ranges. The phase transfer catalyst could be 1-20 mol %, 5-15 mol %, or any specific amount within these ranges.

A carbon containing compound may include an sp3 C—H bond, and is also referred to as a substrate or target herein. Examples of carbon containing compounds include but are not limited to simple alkanes; neopentane; toluene; cyclohexane; norcarne; simple hydrocarbons; trans-decalin; 5α-cholestane; sclarolide; 1,3,5(10)-estratrien-17-one; (1R, 4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate, and other saturated fatty acid esters; N-acetyl-Lyrica methyl ester; artemisinin, adapalene; finasteride; N-acetyl-methylphenidate; mecamylamine and N-acetyl-mecamylamine; N-acetyl-memantine; phthalimidi-memantine; N-acetyl-Enanapril precursor methyl ester; progesterone; artemisinin; adapalene; dopamine derivative; pregabalin; cholestane; finasteride; methylphenidate derivative; mecamylamine; gabapentin; memantine derivative; gabapentin; isoleucine derivative; leucine derivative; valine derivative; pregesterone; tramadol; and (1R,4aS,8aS)-5,5,8a-trimethyl-1-(3-oxobutyl)octahydronaphthalen-2(1H)-one. A carbon containing compound may also be any one of the compounds in FIG. 31, 38 or 39. Arrows in FIGS. 38 and 39 indicate positions that may be halogenated. A carbon containing compound may also include an analog of any carbon containing compound herein. An analog of a carbon containing compound may include substitution of a moiety in the compound for another moiety. The carbon containing compound is a drug or drug candidate precursor of which non-limiting examples are found in FIGS. 31, 38, and 39.

Examples of halogenating agents include but are not limited to a hypohalite, N-chlorosuccinimide (NCS), N-bromosuccinimide, hypochlorous acid, hypobromous acid, hypochlorites, sodium hypochlorite, sodium hypobromite, calcium hypochlorite, and cyanuric chloride. The halogenating agent may be provided by setting conditions to produce a hypohalite in situ.

Examples of halogenating catalysts include but are not limited to metal porphyrins. Metal porphyrins may include manganese, copper, vanadium, chromium, iron, cobalt or nickel. Manganese porphyrin halogenating catalysts may include tetraphenylporphyrinatomanganese chloride (hereinafter "Mn(TPP)Cl"), tetramesitylporphyrinatomanganese (hereinafter "Mn(TMP)Cl") and other similar manganese porphyrins. Manganese porphyrin halogenating catalysts may include tetraphenylporphyrinatomanganese (III) chloride ([Mn$^{III}$(TPP)Cl]), 5,10,15,20-tetramesitylporphyrinato-manganese (III) chloride ([Mn$^{III}$(TMP)Cl]), Mn(III)[tetra-2,6-dichlorophenyl porphyrin, Mn(III)[tetra-2-nitrophenyl porphyrin], Mn(III)[tetra-2-naphthyl porphyrin, Mn(III)[pentachlorophenyl porphyrin, Mn(III)[tetraphenyl-2,3,7,8,12,13,17,18-Octachloroporphyrin], Mn(III)[tetraphenyl-2,3,7,8,12,13,17,18-Octabromoporphyrin], and Mn(III)[tetraphenyl-2,3,7,8,12,13,17,18-Octanitroporphyrin.

Examples of halogenating catalysts include but are not limited to a catalyst having a metal complexed with a ligand. The ligand may include but is not limited to a porphyrin, a phthalocyanine, a corrole, an N-pyridylmethyl-tri-aza-cy-clononane, an N,N-dipyridylmethyl cyclohexadiamine, a tetra-aza-cyclotetra-decane, an N,N-dipyridylmethyl 2,2'-dipyrrolidine, an N,N-dipyridylmethyl ethylenediamine, a tripyridyl amine (TPA), and a salen. The halogenating catalyst may be a trans-difluoromanganese(IV) porphyrin, Mn$^{IV}$(TMP)F$_2$. Halogenating catalysts may include a manganese complex in which manganese is in the 4+ or 5+ oxidation state and which has at least one fluoride ligand bound to manganese, L5Mn(IV)-F or L5Mn(V)-F, in which L can be oxygen, nitrogen or halide, such that manganese has octahedral coordination with six total ligands and a neutral overall charge. Halogenating catalysts may include a manganese complex in which manganese is in the 4+ oxidation state and which has one or two fluoride ligands bound to manganese, L$_5$Mn(IV)-F or L$_4$Mn(IV)-F$_2$, in which L can be oxygen, nitrogen or halide, such that manganese has octahedral coordination with six total ligands and a neutral overall charge.

Examples of phase transfer catalysts include but are not limited to tetrabutylammonium chloride, tetraalkyl ammonium, mixed alkyl ammonium, aryl ammonium, benzyl-trimethylammonium chloride, benzalkonium chloride, benzyl tributylammonium chloride, benzyl triethylammonium chloride, tetrabutyl phosphonium chloride, tetramethyl phosphonium chloride, and dimethyldiphenyl phosphonium chloride.

An embodiment includes a composition including at least one of a carbon containing compound with an sp3 C—H bond, a halogenating agent, a halogenating catalyst or a phase transfer catalyst. An embodiment includes a composition including a partial mix of reactants. The partial mix includes at least one of one of a carbon containing compound with an sp3 C—H bond, a halogenating agent, a halogenating catalyst, or a phase transfer catalyst ready for mixing with the remaining necessary reaction components. The partial mix may be provided in a method of halogenating a carbon containing compound with an sp3 C—H bond, where the remaining components of the reaction are combined with at least a portion of the partial mix. An embodiment includes a kit. The kit may include one or more containers or wells. A container may include at least one of the carbon containing compound with an sp3 C—H bond, a halogenating agent, a halogenating catalyst, or a phase transfer catalyst, but would only include a subset of the reactants such that the halogenating reaction does not proceed until all of the reactants are mixed. A container or well may include a solvent. The kit may include instructions for mixing all of the necessary reactants from the one or more container and, if needed, any other source in order to make a halogenation reaction proceed. All of the necessary reactants may include the carbon containing compound, the halogenating agent, the halogenating catalyst, and the phase transfer catalyst.

An embodiment provides a method of manganese porphyrin catalyzed halogenation. The method may include hypohalites as a halogen source. The method may include halogenating a carbon containing compound in the presence of catalytic amount of Mn(TPP)Cl and tetrabutylammonium chloride as phase transfer catalyst. A catalytic amount of Mn(TPP)Cl may be 1-20 mol %, 5-15 mol %, or any specific amount in these ranges. For example, reaction of sodium hypochlorite with cyclohexane in a biphasic system with Mn(TPP)Cl results in cyclohexyl chloride as the major product at room temperature. Only trace amounts of cyclohexanol, cyclohexanone and other chlorinated products were detected under optimal conditions. The method may be utilized to add any halogen, preferably Cl, Br, I or At. Other halogenating catalysts may replace the Mn(TPP)Cl. In an embodiment, any halogenating catalyst contained herein may be used in place of the manganese porphyrin.

An embodiment provides a manganese porphyrin mediated aliphatic C—H bond chlorination using sodium hypochlorite as the chlorine source. In the presence of catalytic amounts of phase transfer catalyst and manganese porphyrin Mn(TPP)Cl, reaction of sodium hypochlorite with different unactivated alkanes afforded alkyl chlorides as the major products with only trace amounts of oxygenation products. A catalytic amount of phase transfer catalyst may be 1-20 mol %, 5-15 mol %, or any specific amount in these ranges. A catalytic amount of Mn(TPP)Cl may be 1-20 mol %, 5-15 mol %, or any specific amount in these ranges. Substrates with strong C—H bonds, for example (but not limited to) neopentane (BDE=~100 kcal/mol) can be also chlorinated with moderate yield. Chlorination of a diagnostic substrate, for example (but not limited to) norcarane, affords rearranged products indicating a long-lived carbon radical intermediate. Moreover, regioselective chlorination is provided by using a hindered catalyst, Mn(TMP)Cl. In an embodiment, chlorination of trans-decalin with Mn(TMP)Cl provided is provided. 95% selectivity for methylene-chlorinated products as well as a preference for the C2 position may be obtained in the chlorination of trans-decalin with Mn(TMP)Cl. Embodiments also include implementation of the novel halogenation system applied to complex substrates. With 5α-cholestane as the substrate, a method of chlorination is provided where only the C2 and C3 positions are chlorinated. Using this method, chlorination of 5α-cholestane at the C2 and C3 positions may be obtained at a 55% yield. The C2 and C3 positions correspond to the least sterically hindered methylene positions in the A-ring. Chlorination of sclareolide at the equatorial C2 chloride is provided. The reaction with 5α-cholestane is illustrative, and other carbon containing compounds may be similarly halogenated. In an embodiment, any halogenating catalyst contained herein may be used in place of the manganese porphyrin.

In an embodiment, a method is provided to prepare a cross-coupling reagent. The method includes halogenating a carbon containing compound as described herein with a Cl or Br. A method is provided to fluorinate a compound by first modifying the compound with a Cl or Br by a method of halogenating herein, and then replacing the Cl or Br with F. The Cl or Br may be replaced with F by nucleophilic substitution. Nucleophilic conditions may include a source of fluoride ion in a suitable solvent. The source of fluoride ion may include but is not limited to silver fluoride, potassium-crown fluoride, tetraalkyl ammonium fluoride or trialkylamine trihydrofluoride. A suitable solvent may be but is not limited to acetonitrile.

An embodiment provides drug diversification via selective metal-catalyzed halogenation of carbon containing compounds that are drugs. Drug diversification may include fluorination of the carbon containing drug. Drug diversification may include halogenating a drug with a halogenating agent in the presence of a halogenating catalyst and a phase transfer catalyst. Halogenating with Cl or Br may be followed by nucleophilic substitution with F. The method may be utilized for late-stage drug candidate diversification. The halogenating catalyst may be a manganese porphyrin.

The development of metalloporphyrin-catalyzed halogenations of unactivated hydrocarbons could provide a significant new avenue for late-stage drug candidate diversification. Drug diversification may include direct oxidative C—H fluorination of a drug. Further, the realization of such a process could provide insight into the mechanisms of halogenating enzymes such as chloroperoxidase, a heme-containing chlorinating enzyme, and Syr3, a nonheme Fe(II) R-ketoglutaratedependent halogenase.

Methods of manganese-catalyzed direct oxidative C—H fluorination using fluoride ion are embodiments herein. A method of direct oxidative fluorination of a carbon containing compound with an sp3 C—H bond includes reacting a carbon containing compound with a fluorinating agent in the presence of a fluorinating catalyst and an oxidant.

A carbon containing compound may have a sp3 C—H bond, and is also referred to as a substrate or target herein. Examples of carbon containing compounds that can be the target of direct oxidative C—H fluorination include but are not limited to those listed above with respect to halogenation, cyclic alkanes, steroids, steroid derivatives, 5α-androstan-17-one, bornyl acetate, azo-bis-α-phenylethane, trepanoids, simple hydrocarbons, substituted alkanes, ester, tertiary alcohol, ketone and amine substituents, mono-substituted five and seven membered cycloalkanes, cyclohexane, ethylbenzene, methyl cyclopentanone, methyl cyclohexylcarboxylate, methyl cyclohexanol, cycloheylacetate, N-acetyl-gabapentin methyl ester; acetyl-amantidine; phthalimido-amantadine; methyloctanoate, and other saturated fatty acid esters; N-acetyl-Lyrica methyl ester; artemisinin, adapalene; finasteride; N-acetyl-methylphenidate; mecamylamine and N-acetyl-mecamylamine; N-acetyl-memantine; phthalimidi-memantine; N-acetyl-Enanapril precursor methyl ester; progesterone; artemisinin; adapalene; dopamine derivative; pregabalin; cholestane; finasteride; methylphenidate derivative; mecamylamine; gabapentin; memantine derivative; gabapentin; isoleucine derivative; leucine derivative; valine derivative; pregesterone; tramadol; and (1R,4aS,8aS)-5,5,8a-trimethyl-1-(3-oxobutyl)octahydronaphthalen-2(1H)-one. Carbon containing compounds utilized in direct fluorination may further include any compound illustrated in FIGS. 31, 38 and 39. Arrows in FIGS. 38 and 39 indicate positions that may be fluorinated. Similar fluorinations may occur to the targets in FIG. 31. A carbon containing compound may also include an analog of any carbon containing compound herein. An analog of a carbon containing compound may include substitution of a moiety in the compound for another moiety. The carbon containing compound is a drug or drug candidate precursor of which non-limiting examples are found in FIGS. 31, 38, and 39.

Examples of fluorinating agents include but are not limited to silver (I) fluoride, silver (II) fluoride, tetrabutyl ammonium fluoride ("TBAF"), sodium fluoride, potassium fluoride, tetra alkyl ammonium fluoride, trialkyl amine trihydrofluoride designated as $R_3N(HF)_3$ or as the ammonium salt $[R_3NH][H_2F_3]$, and potassium crown ether fluoride.

Examples of fluorinating catalysts include but are not limited to a catalyst having a metal complexed with a ligand. The ligand may include but is not limited to a porphyrin, a phthalocyanine, a corrole, an N-pyridylmethyl-tri-aza-cyclononane, an N,N-dipyridylmethyl cyclohexadiamine, a tetra-aza-cyclotetra-decane, an N,N-dipyridylmethyl 2,2'-dipyrrolidine, an N,N-dipyridylmethyl ethylenediamine, a tripyridyl amine (TPA), and a salen. The metal may be V, Mn, Fe, Co and Ni. Fluorinating catalysts may include manganese porphyrins including Mn(TPP)Cl, Mn(TMP)Cl, $Mn^{III}$(TPP)C, $Mn^{III}$(TMP)Cl or other similar manganese porphyrins. The fluorinating catalyst may be a trans-difluoromanganese(IV) porphyrin, $Mn^{IV}$(TMP)$F_2$. Fluorinating catalysts may include a manganese complex in which manganese is in the 4+ or 5+ oxidation state and which has at least one fluoride ligand bound to manganese, L5Mn(IV)-F or $L_5$Mn(V)-F, in which L can be oxygen, nitrogen or halide, such that manganese has octahedral coordination with six total ligands and a neutral overall charge. Fluorinating catalysts may include a manganese complex in which manganese is in the 4+ oxidation state and which has one or two fluoride ligands bound to manganese, $L_5$Mn(IV)-F or $L_4$Mn(IV)-$F_2$, in which L can be oxygen, nitrogen or halide, such that manganese has octahedral coordination with six total ligands and a neutral overall charge.

Oxidants may be meta-chloroperoxybenzoic acid (mCPBA), idosylbenzene, peroxyacid, alkyl peroxide, peroxy sulfate(oxone), peroxycarbonate, peroxyborate, iodosyl mesitylene, pentafluoro-iodosylbenzene, benzene difluoroiodinane [phenyl-IF2], diacetoxyiodobenzene, 2-iodosylbenzoic acid, peroxyacetic acid, peroxyphthalic acid, and peroxytungstic acid.

An embodiment includes a composition including at least one of a carbon containing compound with an sp3 C—H bond, a fluorinating agent, a fluorinating catalyst, or an oxidant. An embodiment includes a composition including a partial mix of reactants. The partial mix includes at least one of one of a carbon containing compound with an sp3 C—H bond, a fluorinating agent, a fluorinating catalyst, or an oxidant ready for mixing with the remaining necessary reaction components. The partial mix may be provided in a method of fluorinating a carbon containing compound, where the remaining components of the reaction are combined with at least a portion of the partial mix. An embodiment includes a kit. The kit may include one or more container. Each container would include at least one of a carbon containing compound, a fluorinating agent, a fluorinating catalyst, or an oxidant, but would only include a subset of the reactants such that the fluorinating reaction does not proceed until all of the reactants are added. The kit may include instructions for mixing all of the necessary reactants from the one or more container and, if needed, any other source in order to make the reaction proceed. All of the necessary reactants may include the carbon containing compound, the fluorinating agent, the fluorinating catalyst, and the oxidant.

An embodiment includes a composition comprising a manganese complex in which manganese is in the 4+ or 5+ oxidation state and which has at least one fluoride ligand bound to manganese, L5Mn(IV)-F or $L_5$Mn(V)-F, in which L can be oxygen, nitrogen or halide, such that manganese has octahedral coordination with six total ligands and a neutral overall charge. An embodiment includes a composition comprising a manganese complex in which manganese is in the 4+ oxidation state and which has one or two fluoride ligands bound to manganese, $L_5$Mn(IV)-F or L4Mn(IV)-$F_2$, in which L can be oxygen, nitrogen or halide, such that manganese has octahedral coordination with six total ligands and a neutral overall charge.

The manganese porphyrin-fluoride ion direct oxidative fluorination herein accomplishes this transformation under mild conditions. Simple alkanes, terpenoids and even steroids can be selectively fluorinated at otherwise inaccessible sites in 50-80% yield. As an example, decalin was fluorinated predominantly at the C2 and C3 methylene positions. Also, bornyl acetate afforded exo-5-fluoro-bornyl acetate and 5α-androstan-17-one was fluorinated selectively in the A ring. Mechanistic analysis indicates that the regioselectivity for C—H bond cleavage is directed by an oxomanganese(V) catalyst intermediate, while fluorine delivery is suggested to occur via an unusual manganese(IV) fluoride that has been isolated and structurally characterized. This one-step C—H fluorination using fluoride ion is rapid enough to be applied to 18F radiofluorination for positron emission applications.

Embodiments herein place fluorine at such inaccessible sites in biomolecules and drug candidates. Fluorination of drugs can block sites of phase I metabolism by cytochrome P450 enzymes as well as improving target binding affinities. Further, the incorporation of $^{18}F$ into biomolecules can allow direct imaging of metabolic activity and drug targets using the exquisite sensitivity of positron emission tomography. An embodiment includes any carbon containing compound halogenated or fluorinated by a method herein. The products include modified drugs and imaging agents.

An embodiment includes a method of creating fluorinated analogs of drug molecules, natural products and precursors thereof in which $sp^3$ C—H bonds are replaced with fluorine using fluoride ion as a fluorine source.

An embodiment includes a method of incorporating $^{18}F$ from fluoride ion into known drug molecules, natural products and precursors thereof in which $sp^3$ C—H bonds are replaced with fluorine.

Direct oxidative fluorination herein is similar to the halogenation reactions described in examples 1-6, but with several changes in the reaction conditions and reaction reagents to lead to fluorination. The method may include manganese porphyrin catalyzed halogenation where the halide is fluoride. The method may include at least one of silver(I) fluoride or silver(II) fluoride as a halogen source. The method may include halogenating a carbon containing compound in the presence of catalytic amount of Mn(TPP)Cl and tetrabutylammonium fluoride, which can be an additional source of fluoride or may act as a phase transfer catalyst (PTC). The method may employ both silver(I) fluoride and tetrabutylammonium fluoride and fluorine sources. The method may also employ silver(I) (18-F) fluoride, silver(II) (18-F)fluoride and tetrabutylammonium (18-F)fluoride as sources and the 18-F labeled products may be used for positron emitting tomography (PET) applications. An oxidant may be used. The oxidant may be one such as a peroxyacid, alkyl peroxide, peroxy sulfate (Oxone®), peroxycarbonate or peroxyborate. For example, reaction of m-chloroperoxybenzoic acid with cyclooctane in a monophasic system employing either acetonitrile or methylene chloride as solvents, or both by direct oxidative fluorination results in cyclooctyl fluoride in greater than 50% conversion. Temperatures between and including 0° C. and 80° C. may be used. The temperature may be in a range between any two integer value temperatures selected from 0° C. to 80° C. The temperature may be in a range between and including 0° C. and 10° C., 10° C. and 20° C., 20° C. and 30° C., 30° C. and 40° C., 40° C. and 50° C., 50° C. and 60° C., 60° C. and 70° C., or 70° C. and 80° C. The temperature may be any one integer value temperature selected from those including and between 0° C. and 80° C. Temperatures between room temperature and 70° C. may be used. The temperature may be any one temperature including and between room temperature and 70° C. Temperatures between 25° C. and 70° C. may be used. The temperature may be any temperature including and between 25° C. and 70° C. Only trace amounts of cyclooctanol, cyclooctanone or other fluorinated or chlorinated products were detected under optimal conditions, as discussed in example 7, general procedures. The temperature ranges in this paragraph may also be provided in a method of halogenating herein.

Figure 8:
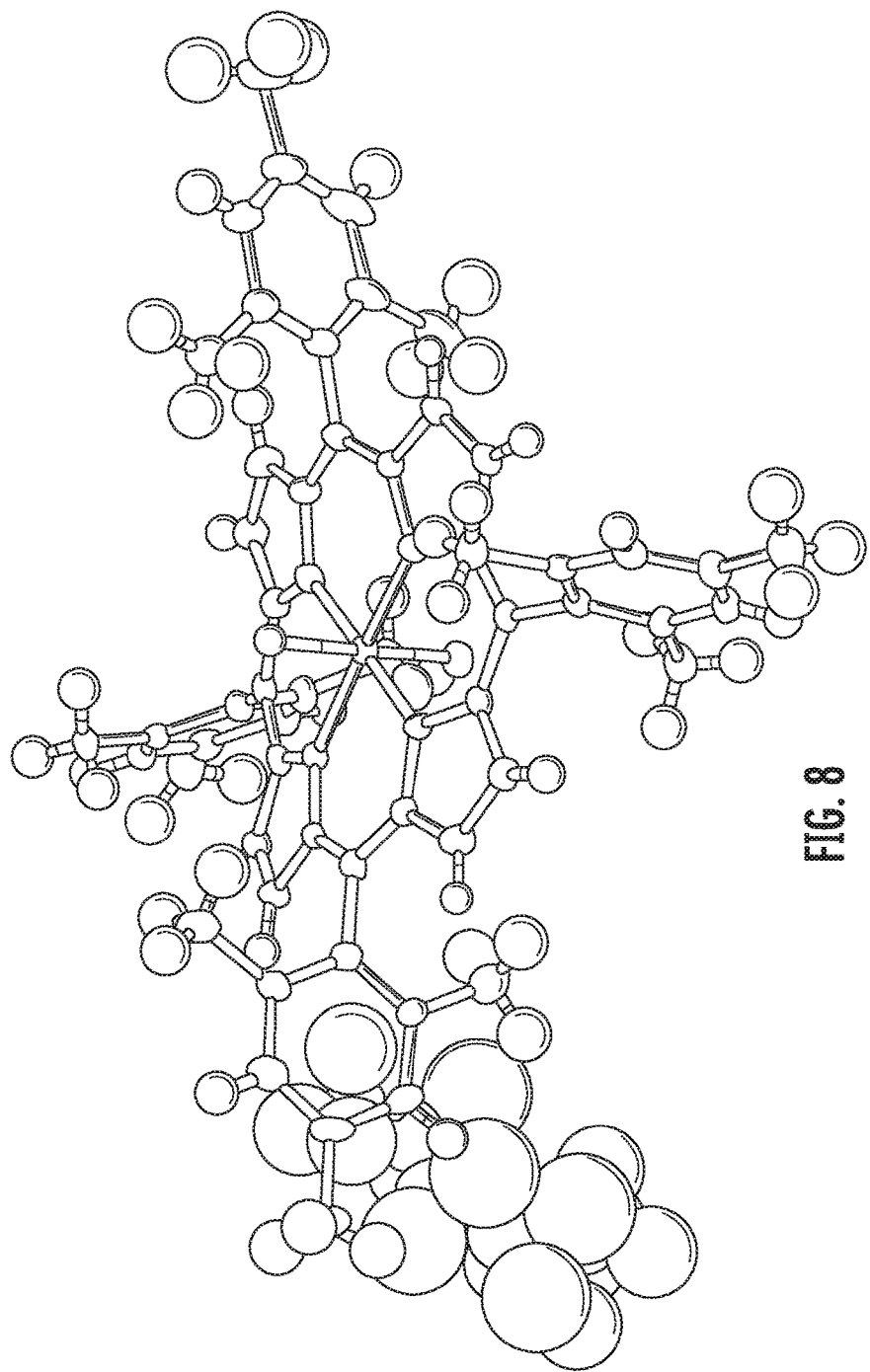
FIG. 8 illustrates the structure of Mn(TMP)F$_2$.
Figure 27:
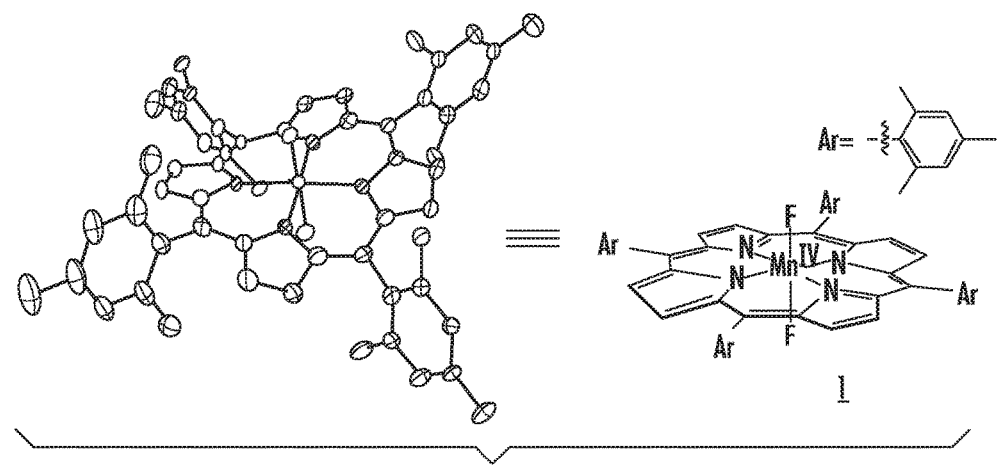
FIG. 27 illustrates an $Mn^{IV}(TMP)F_2$ structure.

An embodiment includes a composition comprising trans-difluoromanganese(IV) porphyrin, $Mn^{IV}(TMP)F_2$. The structure of $Mn^{IV}(TMP)F_2$ is illustrated in FIGS. 2, 8 and 27.

An embodiment includes a method of fluorinating a compound with 18-F (or $^{18}F$), and the compounds produced thereby. Fluorinating a carbon containing compound with 18-F may be achieved by a method of halogenation followed by nucleophilic substitution. Fluorinating a carbon containing compound with 18-F may be achieved by a method of direct oxidative C—H fluorination herein. The method may include fluorinating the compound with 18-F on site for delivery to the patient shortly after synthesis. The visualization of cellular processes by molecular imaging is a promising and non-invasive way to observe disease states and to improve the diagnoses (See Signore, A., Mather, S. J., Piaggio, G., Malviya, G., and Dierckx, R. A. Molecular imaging of inflammation/infection: nuclear medicine and optical imaging agents and methods. Chem. Rev. 2010, 110, 3112-3145; and Pysz, M. A., Gambhir, S. S., and Willmann, J. K. Molecular imaging: current status and emerging strategies. Clin. Radiol. 2010, 65, 500-516, which are incorporated herein by reference as if fully set forth). Positron-emission tomography (PET) in particular, has emerged as a modality of choice because it yields well-resolved images with excellent sensitivity (See Wong, F. C., and Kim, E. E. A review of molecular imaging studies reaching the clinical stage. Eur. J. Radiol. 2009, 70, 205-211; Ametamey, S. M., Honer, M., and Schubiger, P. A. Molecular imaging with PET. Chem. Rev. 2008, 108, 1501-1516; and Chen, K., and Conti, P. S. Target-specific delivery of peptide-based probes for PET imaging. Adv. Drug Delivery Rev. 2010, 62, 1005-1022, which are incorporated herein by reference as if fully set forth). Among the seven positron-emitting isotopes, $^{18}$F has the advantages of a two-hour half and a β+-emission at 635 keV (See Miller, P. W., Long, N. J., Vilar, R., and Gee, A. D. Synthesis of $^{11}$C, $^{18}$F, $^{15}$O, and $^{13}$N radiolabels for positron emission tomography. Angew. Chem., Int. Ed. 2008, 47, 8998-9033; and Cai, L., Lu, S., and Pike, V. W. Chemistry with [$^{18}$F] fluoride ion. Eur. J. Org. Chem. 2008, 2853-2873, which is incorporated herein by reference as if fully set forth). Imaging agents such as $^{18}$F-fluorodeoxyglucose (18F-FDG) have proved to be efficacious for imaging tissue and cells with high glucose metabolism (See Wadsak, W., and Mitterhauser, M. Basic principles of radiopharmaceuticals for PET/CT. Eur. J. Radiol. 2010, 73, 461-469, which is incorporated herein by reference as if fully set forth). A short-coming of current methods of $^{18}$F labeling is that the usual replacement of an oxygen functional group with fluorine changes the polarity of the detection molecule. The method of direct oxidative fluorination herein allows for the one-step replacement of a carbon-bound hydrogen, which has the advantages of using $^{18}$F from a fluoride ion source and creating a detection molecule that does not change the hydrogen bonding pattern of the starting compound.

An embodiment includes visualization by steps including 1) direct oxidative C—H fluorination of a carbon containing compound by a method herein to create an imaging agent, 2) administration of the imaging agent to a patient, and 3) positron emission tomography of the patient. An embodiment includes visualization by steps including 1) Cl or Br halogenation of a carbon containing compound with an sp3 C—H by a method herein, followed by nucleophilic substitution with F to create an imaging agent, 2) administration of the imaging agent to a patient, and 3) positron emission tomography of the patient.

An embodiment includes a composition including a partial mix of reactants necessary to create an imaging agent. The partial mix includes at least one of one of a carbon containing compound, a fluorinating agent, a fluorinating catalyst, or an oxidant ready for mixing with the remaining necessary reaction components. The fluorinating agent may include an $^{18}$F source. The partial mix may be provided in a method of fluorinating a carbon containing compound with $^{18}$F, where the remaining components of the reaction are combined with at least a portion of the partial mix. An embodiment includes a kit for the creation of an imaging agent. The kit may include one or more container. Each container would include at least one of a carbon containing compound, a fluorinating agent, a fluorinating catalyst, or an oxidant, but would only include a subset of the reactants such that the fluorinating reaction does not proceed until all of the reactants are added. The kit may include instructions for mixing all of the necessary reactants from the one or more container and, if needed, any other source in order to make the reaction proceed. All of the necessary reactants may include the carbon containing compound, the fluorinating agent, the fluorinating catalyst, and the oxidant. The fluorinating agent may include an $^{18}$F source.

An embodiment provides a manganese porphyrin mediated aliphatic C—H bond fluorination using tetrabutylammonium fluoride/silver(I) fluoride as the fluorine source. In the presence of catalytic amounts of manganese porphyrin Mn(TPP)Cl, or similar manganese porphyrins or phthalocyanines or porphyrazines, reaction of mCPBA or Oxone with different unactivated alkanes afforded alkyl fluorides as the major products with only trace amounts of oxygenation or chlorinated products. Substrates with strong C—H bonds, for example (but not limited to) neopentane (BDE=~100 kcal/mol) can be also fluorinated with moderate yield. Moreover, regioselective fluorination is provided by using a hindered catalyst. The hindered catalyst may be Mn(TMP)Cl. In an example, fluorination of trans-decalin with Mn(TMP)Cl provided 85% selectivity for methylene-fluorinated products. A preference for the C2 position may be obtained in the fluorination of trans-decalin with Mn(TMP)Cl. Embodiments also include implementation of the novel method of direct oxidative fluorination system applied to complex substrates. The complex substrate may be but is not limited to 5α-cholestane, and the method of direct oxidative fluorination results in fluorination of positions in ring A of 5α-cholestane. Embodiments also include direct oxidative fluorination of sclareolide at the equatorial C2 position and fluorination of bornyl acetate at the C3 position under these conditions.

The combination of tetrabutylammonium fluoride, silver fluoride and various oxidants described above were observed to transform the starting manganese(III) chloride catalyst into the active fluorinating catalyst. These active forms of the catalyst include manganese(III) monofluoride as the axial metal ligand, a trans-difluoromanganese(III), a trans-oxo-fluoromanganese(IV) and trans-difluoromanganese(IV) and a trans-oxofluoromanganese(V). Manganese may be substituted with other first row transition metals including but not limited to copper, vanadium, chromium, iron, cobalt and nickel. An embodiment includes a composition including any of the catalysts above. An embodiment includes a composition including at least one of the catalysts above, a fluorinating agent, an oxidant or a carbon containing compound.

In some embodiments above, specific halogenating agents that are hypohalites are utilized. In situ production of hypohalite using said manganese porphyrins, a halide and a peroxide may also be provided in embodiments herein. See Lahaye, D. and Groves, J. T. J. Inorg. Biochem. 2007, 101, 1786-1797; and N. Jin, J. L. Bourassa, S. C. Tizio, and J. T. Groves, "Rapid, Reversible Oxygen Atom Transfer between an Oxomanganese(V) Porphyrin and Bromide. A Haloperoxidase Mimic with Enzymatic Rates." Angew. Chem. 2000, 39, 3849-3851, which are incorporated herein by reference as if fully set forth. In an embodiment, conditions may be provided that produce hypohalites in situ in place or in addition to directly utilizing a hypohalite. For example, a halogenating method may include providing peroxide, a halide and a manganese porphyrin along with the carbon containing compound. A halogenating method may include providing peroxide, a halide and a nickel porphyrin along with the carbon containing compound.

Figure 7A:
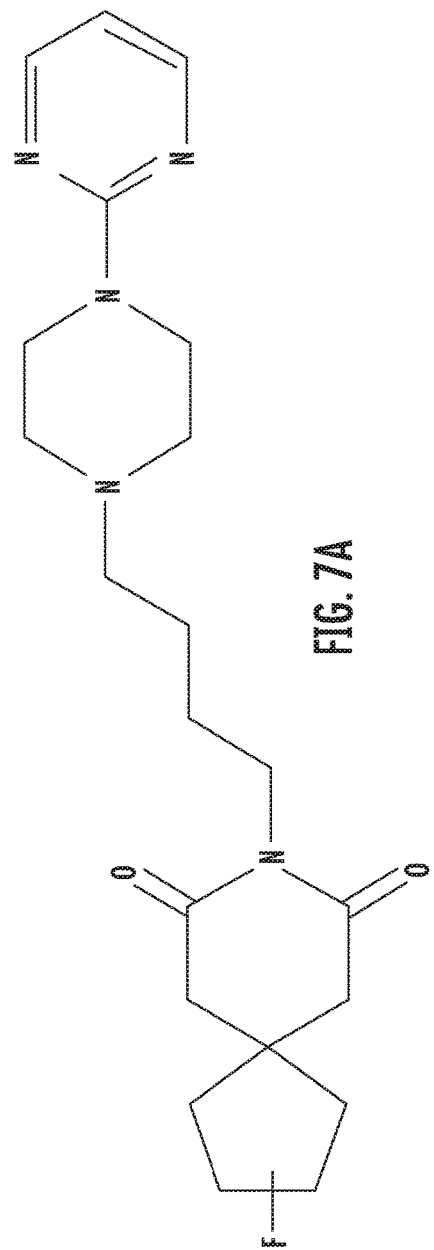
FIGS. 7A-7D.

Embodiments include a compound comprising fluorobuspirone and a method of synthesis thereof. Referring to FIG. 7A, a fluoro-buspirone compound is illustrated. Example 26, below, outlines the synthesis of fluoro-buspirone.

In an embodiment, shorter reaction times for 18F applications may be present. For example, much shorter reaction times (about 1 hr) could be achieved by adding iodosylbenzene oxidant while maintaining the reaction mixture between 60 and 80° C. Also, by using mCPBA as the oxidant, up to 40% yields could be obtained within 1 hr at room temperature and up to 60° C. Each addition of 1 equiv. oxidant may be followed by another charge of Mn(TMP)Cl catalyst (13.2 mg, 1 mmol %) added dissolved in minimal amount of solvents.

An embodiment includes a composition comprising at least one halogenated compound described herein, or an analog thereof. An embodiment includes a composition comprising at least one fluorinated compound described herein, or an analog thereof. An embodiment includes a composition comprising an organic compound with a halogen in place of an aliphatic hydrogen. The halogen replacing an aliphatic hydrogen is not limited to but may be Cl, Br, or F. An embodiment includes a composition comprising an organic compound with an F in place of an aliphatic hydrogen.

An embodiment includes a composition comprising the product of a method of halogenating a carbon containing compound having an sp3 C—H bond herein. The product may be from the method as it is conducted on any target herein or an analog thereof.

An embodiment includes a composition comprising the product of a method of halogenating a carbon containing compound having an sp3 C—H bond herein with Cl or Br to obtain a halogenated product, followed by nucleophilic substitution of the halogenated product with F. The product may be from the method as it is conducted on any target herein or an analog thereof.

An embodiment includes a composition comprising the product of a method of fluorinating a carbon containing compound having an sp3 C—H bond herein. The product may from the method as it is conducted on any target contained herein or an analog thereof.

The fluorinated drug molecules created by methods herein will have nearly the same steric size as the parent drug. But they will contain only one, or possibly two or three fluorine atoms. Fluorine NMR spectroscopy is a very powerful tool for studying such molecules since 19F is NMR active and 100% abundant. Further fluorine has nearly as high a detection level as protons and, importantly, a much larger chemical shift range. Moreover, when a fluorinated molecule binds to another molecule, such as a protein receptor, the fluorine chemical shift can change by as much as 8 ppm, while proton chemical shift changes of only a few tenths (+/−0.3) of a ppm are observed in similar situations. The covalent structure of the molecule is not changed upon binding, but molecular electric fields are affected by such things as hydrogen bonding and hydrogen bonding does occur to fluorine. Accordingly, fluorinated derivatives of drug molecules have the utility of being detectable by fluorine NMR that will not be complicated by the large number of protons found in such molecules. Further, fluorine NMR chemical shift changes will indicate the degree of binding of the fluorinated molecule to a receptor binding site.

EMBODIMENTS

The following list includes particular embodiments of the present invention. The list, however, is not limiting and does not exclude alternate embodiments, as would be appreciated by one of ordinary skill in the art.

1. A method of halogenating a carbon containing compound having an sp3 C—H bond comprising: combining a carbon containing compound, a halogenating agent, a halogenating catalyst, and a phase transfer catalyst.

2. The method of embodiment 1, wherein the carbon containing compound is added in a concentration from 1 mM to 1 M, the halogenating agent is added in a concentration from 1 mM to 3 M, the halogenating catalyst is added in a concentration from 1 to 20 mole percent, and the phase transfer catalyst is added in a concentration from 1 to 20 mole percent.

3. The method of any one or more of the preceding embodiments, further comprising allowing the carbon containing compound, the halogenating agent, the halogenating catalyst, and the phase transfer catalyst to react for 30 minutes to 12 hours.

4. The method of any one or more of the preceding embodiments further comprising maintaining the carbon containing compound, the halogenating agent, the halogenating catalyst, and the phase transfer catalyst at a temperature from 0° C. to 80° C.

5. The method of any one or more of the preceding embodiments, wherein combining further comprises: mixing the phase transfer catalyst, the halogenating catalyst and the carbon containing compound in a solvent to form a first mixture; and adding the halogenating agent to the first mixture to form a second mixture.

6. The method of embodiment 5 further comprising providing an inert gas over at least one of the first mixture or the second mixture.

7. The method of embodiment 6, wherein the inert gas is $N_2$.

8. The method of any one or more of the preceding embodiments, wherein the solvent is at least one selected from the group consisting of dichloromethane, dichlorobenzene, acetonitrile and 1,2-dichloroethane.

9. The method of any one or more of the preceding embodiments, wherein the carbon containing compound includes a compound selected from the group consisting of neopentane; toluene; cyclohexane; norcarane; trans-decalin; 5α-cholestane; sclareolide; 1,3,5(10)-estratrien-17-one; (1R,4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholestane; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R,4aS,8aS)-5,5,8a-trimethyl-1-(3-oxobutyl)octahydronaphthalen-2(1H)-one; phenylalanine; donepezil precursor; amphetamine; δ-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; and cyclohexane carboxylic acid methyl ester; or an analog of any one of the foregoing.

10. The method of any one or more of the preceding embodiments, wherein the carbon containing compound is a drug or drug candidate precursor.

11. The method of any one or more of the preceding embodiments, wherein the halogenating agent is includes a substance selected from the group consisting of a hypohalite, N-chlorosuccinimide (NCS), N-bromosuccinimide, hypochlorous acid, hypobromous acid, hypochlorites, NaOCl, NaOBr, calcium hypochlorite, and cyanuric chloride.

12. The method of embodiment 11, wherein the hypohalite is provided by setting conditions to produce a hypohalite in situ by adding chlorine gas to a water solution of sodium or potassium hydroxide.

13. The method of any one or more of the preceding embodiments, wherein the halogenating catalyst includes a substance selected from the group consisting of tetraphenylporphyrinatomanganese (III) chloride ([Mn$^{III}$(TPP)Cl]), 5,10,15,20-tetramesitylporphyrinatomanganese (III) chloride ([Mn$^{III}$(TMP)Cl]), Mn(III)[tetra-2,6-dichlorophenyl porphyrin, Mn(III)[tetra-2-nitrophenyl porphyrin], Mn(III)[tetra-2-naphthyl porphyrin, Mn(III)[pentachlorophenyl porphyrin, Mn(III)[tetraphenyl-2,3,7,8,12,13,17,18-Octachloroporphyrin], Mn(III)[tetraphenyl-2,3,7,8,12,13,17,18-Octabromoporphyrin], and Mn(III)[tetraphenyl-2,3,7,8,12,13,17,18-Octanitroporphyrin.

14. The method of any one or more of the preceding embodiments, wherein the halogenating catalyst is selected from the group consisting of M(TPP)Cl, M (TMP)Cl, M[tetra-2,6-dichlorophenyl porphyrin, M[tetra-2-nitrophenyl porphyrin], M[tetra-2-naphthyl porphyrin, M[pentachlorophenyl porphyrin, M[tetraphenyl-2,3,7,8,12,13,17,18-Octachloroporphyrin], M[tetraphenyl-2,3,7,8,12,13,17,18-Octabromoporphyrin], M[tetraphenyl-2,3,7,8,12,13,17,18-Octanitroporphyrin], metal salen complexes having the formula M(salen), metal salophen complexes having the formula M(salophen), metal phthalocyanine complexes having the formula M(phth), and metal porphyrazine complexes having the formula M(Pz), where M is a metal.

15. The method of embodiment 14, wherein M is selected from the group consisting of manganese, copper, vanadium, chromium, iron, cobalt and nickel.

16. The method of any one or more of the preceding embodiments, wherein the phase transfer catalyst includes a substance selected from the group consisting of tetrabutylammonium chloride, tetraalkyl ammonium, mixed alkyl ammonium, aryl ammonium, benzyl-trimethylammonium chloride, benzalkonium chloride, benzyl tributylammonium chloride, benzyl triethylammonium chloride, tetrabutyl phosphonium chloride, tetramethyl phosphonium chloride, and dimethyldiphenyl phosphonium chloride.

17. A method of fluorinating a carbon containing compound having an sp3 C—H bond comprising: combining a carbon containing compound, a halogenating agent, a halogenating catalyst, and a phase transfer catalyst; obtaining a halogenated product; and conducting nucleophilic substitution on the halogenated product with a fluorine source.

18. The method of embodiment 17, wherein the fluorine source is potassium fluoride.

19. The method of any one or more of the preceding embodiments, wherein the step of nucleophilic substitution is conducted in the presence of a phase transfer catalyst.

20. The method of any one or more of the preceding embodiments, wherein the carbon containing compound includes a compound selected from the group consisting of neopentane; toluene; cyclohexane; norcarane; trans-decalin; 5α-cholestane; sclareolide; 1,3,5(10)-estratrien-17-one; (1R,4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholestane; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R, 4aS,8aS)-5,5,8a-trimethyl-1-(3-oxobutyl)octahydronaphthalen-2(1H)-one; phenylalanine; donepezil precursor; amphetamine; δ-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; and cyclohexane carboxylic acid methyl ester; or an analog of any one of the foregoing.

21. The method of any one or more of the preceding embodiments, wherein the carbon containing compound is a drug or drug candidate precursor.

22. The method of any one or more of the preceding embodiments, wherein the halogenating agent is includes a substance selected from the group consisting of a hypohalite, N-chlorosuccinimide (NCS), N-bromosuccinimide, hypochlorous acid, hypobromous acid, hypochlorites, NaOCl, NaOBr, calcium hypochlorite, and cyanuric chloride.

23. The method of any one or more of the preceding embodiments, wherein the hypohalite is provided by setting conditions to produce a hypohalite in situ by adding chlorine gas to a water solution of sodium or potassium hydroxide.

24. The method of any one or more of the preceding embodiments, wherein the halogenating catalyst includes a substance selected from the group consisting of tetraphenylporphyrinatomanganese (III) chloride ([Mn$^{III}$(TPP)Cl]), 5,10,15,20-tetramesitylporphyrinatomanganese (III) chloride ([Mn$^{III}$(TMP)Cl]), Mn(III)[tetra-2,6-dichlorophenyl porphyrin, Mn(III)[tetra-2-nitrophenyl porphyrin], Mn(III)[tetra-2-naphthyl porphyrin, Mn(III)[pentachlorophenyl porphyrin, Mn(III)[tetraphenyl-2,3,7,8,12,13,17,18-Octachloroporphyrin], Mn(III)[tetraphenyl-2,3,7,8,12,13,17,18-Octabromoporphyrin], and Mn(III)[tetraphenyl-2,3,7,8,12,13,17,18-Octanitroporphyrin.

25. The method of any one or more of the preceding embodiments, wherein the halogenating catalyst is selected from the group consisting of M(TPP)Cl, M (TMP)Cl, M[tetra-2,6-dichlorophenyl porphyrin, M[tetra-2-nitrophenyl porphyrin], M[tetra-2-naphthyl porphyrin, M[pentachlorophenyl porphyrin, M[tetraphenyl-2,3,7,8,12,13,17,18-Octachloroporphyrin], M[tetraphenyl-2,3,7,8,12,13,17,18-Octabromoporphyrin], M[tetraphenyl-2,3,7,8,12,13,17,18-Octanitroporphyrin], metal salen complexes having the formula M(salen), metal salophen complexes having the formula M(salophen), metal phthalocyanine complexes having the formula M(phth), and metal porphyrazine complexes having the formula M(Pz), where M is a metal.

26. The method of any one or more of the preceding embodiments, wherein M is selected from the group consisting of manganese, copper, vanadium, chromium, iron, cobalt and nickel.

27. The method of any one or more of the preceding embodiments, wherein the phase transfer catalyst includes a substance selected from the group consisting of tetrabutylammonium chloride, tetraalkyl ammonium, mixed alkyl ammonium, aryl ammonium, benzyl-trimethylammonium chloride, benzalkonium chloride, benzyl tributylammonium chloride, benzyl triethylammonium chloride, tetrabutyl phosphonium chloride, tetramethyl phosphonium chloride, and dimethyldiphenyl phosphonium chloride.

28. A composition comprising the product of the method of any one of embodiments 1-27.

29. A composition comprising at least two or more of a carbon containing compound having an sp3 C—H bond hydrogen, a halogenating agent, a halogenating catalyst, or a phase transfer catalyst.

30. The composition of embodiment 29, wherein the carbon containing compound includes a compound selected from the group consisting of neopentane; toluene; cyclohexane; norcarane; trans-decalin; 5α-cholestane; sclareolide; 1,3,5(10)-estratrien-17-one; (1R,4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholestane; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R,4aS,8aS)-5,5,8a-trimethyl-1-(3-oxobutyl)octahydronaphthalen-2(1H)-one; phenylalanine; donepezil precursor; amphetamine; δ-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; and cyclohexane carboxylic acid methyl ester; or an analog of any one of the foregoing.

31. The composition of any one or more of the preceding embodiments, wherein the halogenating agent is includes a substance selected from the group consisting of a hypohalite, N-chlorosuccinimide (NCS), N-bromosuccinimide, hypochlorous acid, hypobromous acid, hypochlorites, NaOCl, NaOBr, calcium hypochlorite, and cyanuric chloride.

32. The composition of any one or more of the preceding embodiments, wherein the hypohalite is provided by setting conditions to produce a hypohalite in situ by adding chlorine gas to a water solution of sodium or potassium hydroxide.

33. The composition of any one or more of the preceding embodiments, wherein the halogenating catalyst includes a substance selected from the group consisting of tetraphenylporphyrinatomanganese (III) chloride ([Mn$^{III}$(TPP)Cl]), 5,10,15,20-tetramesitylporphyrinatomanganese (III) chloride ([Mn$^{III}$(TMP)Cl]), Mn(III)[tetra-2,6-dichlorophenyl porphyrin, Mn(III)[tetra-2-nitrophenyl porphyrin], Mn(III)[tetra-2-naphthyl porphyrin, Mn(III)[pentachlorophenyl porphyrin, Mn(III)[tetraphenyl-2,3,7,8,12,13,17,18-Octachloroporphyrin], Mn(III)[tetraphenyl-2,3,7,8,12,13,17,18-Octabromoporphyrin], and Mn(III)[tetraphenyl-2,3,7,8,12,13,17,18-Octanitroporphyrin.

34. The composition of any one or more of the preceding embodiments, wherein the halogenating catalyst is selected from the group consisting of M(TPP)Cl, M (TMP)Cl, M[tetra-2,6-dichlorophenyl porphyrin, M[tetra-2-nitrophenyl porphyrin], M[tetra-2-naphthyl porphyrin, M[pentachlorophenyl porphyrin, M[tetraphenyl-2,3,7,8,12,13,17,18-Octachloroporphyrin], M[tetraphenyl-2,3,7,8,12,13,17,18-Octabromoporphyrin], M[tetraphenyl-2,3,7,8,12,13,17,18-Octanitroporphyrin], metal salen complexes having the formula M(salen), metal salophen complexes having the formula M(salophen), metal phthalocyanine complexes having the formula M(phth), and metal porphyrazine complexes having the formula M(Pz), where M is a metal.

35. The composition of any one or more of the preceding embodiments, wherein M is selected from the group consisting of manganese, copper, vanadium, chromium, iron, cobalt and nickel.

36. The composition of any one or more of the preceding embodiments, wherein the phase transfer catalyst includes a substance selected from the group consisting of tetrabutylammonium chloride, tetraalkyl ammonium, mixed alkyl ammonium, aryl ammonium, benzyl-trimethylammonium chloride, benzalkonium chloride, benzyl tributylammonium chloride, benzyl triethylammonium chloride, tetrabutyl phosphonium chloride, tetramethyl phosphonium chloride, and dimethyldiphenyl phosphonium chloride.

37. A composition comprising an organic compound with a halogen in place of an sp3 C—H bond.

38. The composition of embodiment 37, wherein the halogen is selected from the group consisting of chlorine, bromine and fluorine.

39. A kit comprising one or more container, wherein each container includes at least one reactant for a halogenation reaction selected from the group consisting of a carbon containing compound, a halogenating agent, a halogenating catalyst, or a phase transfer catalyst, wherein the composition includes at least one fewer substance than required to make a halogenation reaction proceed.

40. The kit of embodiment 39, further comprising a container having a solvent.

41. The kit of any one or more of the preceding embodiments, wherein the one or more containers in combination include all substances required to make the halogenation reaction proceed.

42. The kit of any one or more of the preceding embodiments, further including instructions for mixing the reactants from the at least one container.

43. A composition comprising a product of a method of halogenating a carbon containing compound having an sp3 C—H bond comprising combining the carbon containing compound, a halogenating agent, a halogenating catalyst, and a phase transfer catalyst.

44. The composition of embodiment 43, wherein the carbon containing compound is neopentane; toluene; cyclohexane; norcarane; trans-decalin; 5α-cholestane; sclareolide; 1,3,5(10)-estratrien-17-one; (1R,4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine;

N-acetyl-enanapril precursor methyl ester; progesterone; artemisinin; adapalene; dopamine derivative; pregabalin; cholesterol; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R,4aS,8aS)-5,5,8a-trimethyl-1-(3-oxobutyl)octahydronaphthalen-2(1H)—one; phenylalanine; donepezil precursor; amphetamine; δ-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; and cyclohexane carboxylic acid methyl ester; or an analog of any one of the foregoing.

45. A composition comprising a product of a method of fluorinating a carbon containing compound having an sp3 C—H bond comprising combining the carbon containing compound, a halogenating agent providing Cl or Br, a halogenating catalyst, and a phase transfer catalyst, obtaining a halogenated product, and conducting nucleophilic substitution on the halogenated product with a fluorine source.

46. The composition of embodiment 45, wherein the carbon containing compound is neopentane; toluene; cyclohexane; norcarane; trans-decalin; 5α-cholestane; sclareolide; 1,3,5(10)-estratrien-17-one; (1R,4aS,8aS)-octahydro-5,5,8a-trimethyl-1-(3-oxobutyl)-naphtalenone; (1R,4S,6S,10S)-4,12,12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholesterol; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R,4aS,8aS)-5,5,8a-trimethyl-1-(3-oxobutyl)octahydronaphthalen-2(1H)—one; phenylalanine; donepezil precursor; amphetamine; δ-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; cyclohexane carboxylic acid methyl ester; or an analog thereof.

47. A composition comprising any halogenated compound described herein or obtained by a reaction herein.

48. A composition comprising any halogenating catalyst herein.

49. A composition comprising the product of any reaction herein.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

As discussed herein, substrates and targets are carbon containing compounds that halogenated or fluorinated by the methods herein.

Example 1—Mn(TPP)Cl Catalyzed Halogenation

It was found that a biphasic system with catalytic amounts of Mn(TPP)Cl, tetrabutylammonium chloride as a phase transfer catalyst (PTC), and sodium hypochlorite transformed a variety of simple alkanes to alkyl chlorides with high selectivity (Table 1, below). Only trace amounts of oxygenated and other chlorinated products were detected under optimal conditions. There was negligible reaction in the absence of the Mn or PTC. Interestingly, even substrates with strong C—H bonds, such as neopentane (BDE=~100 kcal/mol) could be chlorinated with a useful yield by using Mn(TMP)Cl, as the catalyst. When toluene was used as the substrate, the benzylic position was chlorinated exclusively. Interestingly, cyclohexane and toluene were found to have similar reactivities in a competitive reaction, despite the 11 kcal/mol difference in C—H BDE. Moreover, when norcarane was used as a diagnostic substrate, the major product was rearranged, indicating the involvement of a long-lived radical intermediate, similar to manganese porphyrin mediated hydroxylation reactions. The chlorination reaction may be expanded to bromination simply by replacing NaOCl with NaOBr. The bromination of cyclohexane provided cylcohexyl bromide as the main product with insignificant amounts of cyclohexyl chloride, indicating that the hypohalite is the halogen source rather than the solvent or the axial ligand.

Representative, Non-Limiting Materials.

Sodium hypochlorite (NaOCl, Aldrich) was standardized spectroscopically (λmax292 nm, ε350M-1 cm-1). Sodium hypobromite was prepared by mixing NaOCl with 10% excess sodium bromide (NaBr, 99.99% Aldrich) and used immediately. 5,10,15,20-tetraphenylporphyrinatomanganese(III) chloride [$Mn^{III}$(TPP)Cl] was purchased from Aldrich. 5,10,15,20-tetramesitylporphyrinatomanganese (III) chloride [$Mn^{III}$(TMP)Cl] was prepared by metallation of tetramesitylporphyrin. Bicyclo[4.1.0] heptane (norcarane) was prepared according to a literature method (Smith, R. D.; Simmons, H. E. Org. Synth. 1961, 41, 72). Dichloromethane (HPLC grade) was distilled from $CaH_2$. Water was distilled and deionized with a Millipore system. Other materials were purchased of the highest purity from Aldrich and used without further purification.

Instrumentation.

NMR spectra were obtained on a 500 MHz Varian INOVA spectrometer and are reported in ppm using solvent as an internal standard ($CDCl_3$ at 7.26 ppm). GC/MS analyses were performed on an Agilent 7890A Gas chromatograph equipped with an Agilent 5975 mass selective detector. Internal standards were used for quantification by measuring the relative response factors.

Catalytic Chlorination of Simple Hydrocarbons.

Exemplary simple substrates (i.e., carbon containing compounds) are listed in Table 1, below, and the method exemplified here may be utilized with other substrates. Under a nitrogen atmosphere, 2 mL NaOCl(0.33 MpH=11) was added to a solution of manganese porphyrin (0.013 mmol), tetrabutylammonium chloride (TBACl, 0.027 mmol), and substrate (2 mmol) in 1 mL dichlormethane in a 4 mL sealed vial. The biphasic mixture was stirred smoothly under nitrogen. Reactions were run at ambient temperature and completion of the reaction was indicated by disappearance of the brown red color of high valent porphyrin and formation of the green color of manganese(III) species. The catalysts were removed by a short silica gel column eluted by $CH_2Cl_2$ and the solution was analyzed by GC/MS. Yields of chlorinated products were calculated based on oxidant added. The assignment of the products was based on the comparison of GC retention times and fragmentation with authentic samples.

TABLE 1

Halogenation of simple hydrocarbons[a]

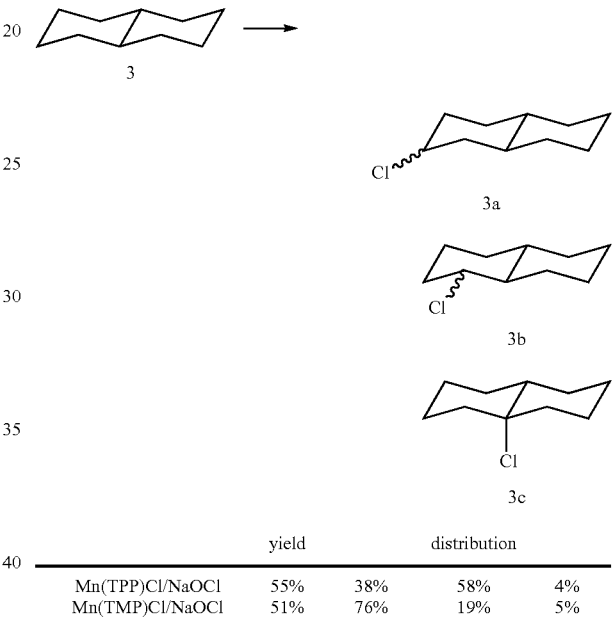

| Substrate | Product | Yield[b] |
|---|---|---|
| 1 | | 69%, 57% |
| 2 | | 74% |
| 3 | | 38% |
| 4[c] | | 31% |
| 5 | | 12%, 28% |
| 6[d] | | 49% |

[a]Standard conditions: Substrate/oxidant/1/PTC = 300:100:2:4.
[b]Yield based on oxidant. Yield determined by GC.
[c]Mn(TMP)Cl was used as catalyst.
[d]NaOBr, prepared by treatment of NaOCl with a slight excess of NaBr, was used as the oxidant.

Example 2—Chlorination of Trans-Decalin

The chlorination of trans-decalin catalyzed by Mn(TPP)Cl or Mn(TMP)Cl was very revealing. With commonly employed chlorinating agents such as N-chlorosuccinimide (NCS) or hypochlorous acid, this substrate provides a mixture of products with poor regioselectivity and tertiary/secondary selectivities of ~1.4 and ~3, respectively. Significantly, chlorination of trans-decalin with Mn(TPP)Cl as the catalyst provided 95% selectivity for methylene-chlorinated products (Scheme 1, below). Furthermore, when the more hindered catalyst Mn(TMP)Cl was used, 2-chlorodecalins (3a, below) were obtained with 76% selectivity. Such a high selectivity for chlorination of unactivated methylene C—H bonds has not been observed before.

The products of trans-decalin chlorination were assigned by comparing the GC retention time with authentic samples, prepared by treating corresponding alcohols with thionyl chloride. The ratio of equatorial and axial isomers was ~1 for both C1 and C2 chlorination.

Scheme 1: Chlorination of trans-Decalin

| | yield | distribution | | |
|---|---|---|---|---|
| Mn(TPP)Cl/NaOCl | 55% | 38% | 58% | 4% |
| Mn(TMP)Cl/NaOCl | 51% | 76% | 19% | 5% |

Example 3—Methods for Halogenating Complex Substrates

Referring to FIGS. 1A and 1B, example methods for halogenating complex substrates are illustrated. An exemplary complex substrate may be 5α-cholestane but the method herein may be utilized with other substrates. The chlorination of 5α-cholestane, a saturated steroid that contains 48 unactivated C—H bonds, was examined. Remarkably, despite six tertiary C—H bonds and 13 possible methylene sites of chlorination, chlorination was only observed at the C2 and C3 positions, the least sterically hindered methylene positions in the A-ring, in a net 55% yield. Referring to FIG. 1A, the C2 chlorination afforded a 15:1 selectivity for the equatorial chloride (4a in FIG. 1A), while a mixture of epimers was found at C3 (4b in FIG. 1A). This example highlights the capacity of steric factors to produce high selectivity for the chlorination of secondary C—H bonds in a simple, intermolecular event.

5α-cholestane chlorination: Under a nitrogen atmosphere, 2 mLNaOCl (0.33M pH=11) was added to a solution of Mn(TMP)Cl (0.033 mmol), tetrabutylammonium chloride (TBACl, 0.027 mmol), cholestane (0.22 mmol) in 1 mL dichloromethane in a 4 mL sealed vial. The biphasic mixture was stirred smoothly under nitrogen. The aqueous layer was removed after 12 h and another equiv of fresh hypochlorite was added under $N_2$. The reaction was run for another 12 h and the crude mixture was analyzed by $^1H$ NMR.

The Mn(TPP)Cl catalyzed chlorination of cholestane resulted in a more complex product mixture. Significantly, the ratio of equatorial to axial C2 chloride was approximately 1:1 compared to 15:1 for Mn(TMP)Cl, suggesting that a porphyrin species is involved in the halogen transfer step.

Sclareolide is a plant-derived terpenoid with antifungal and cytotoxic activities. Referring to FIG. 1B, the Mn(TMP)Cl catalyzed chlorination of sclareolide afforded a 42% isolated yield of the C2 equatorial chloride (5a in FIG. 1B). The structure was confirmed by observing the signature triplet of triplets at δ 4.22 (J) 12.1, 4.2 Hz) in the $^1H$-NMR of 5a. The C2/C3 selectivity was 7:1. The method may be extended to any complex substrate.

Sclareolide chlorination: The procedure is similar to the cholestane chlorination described above, with the exception that products were purified by flash chromatography (5% EtOAc/hexanes) and starting material was recycled twice. The assignment of the major product was based on the unique $^1H$ NMR coupling pattern of the axial C2 proton $H_a$ at δ 4.22, which displayed one large (anti) and one small (gauche) J-value (triplet of triplets). $^1H$ NMR (500 MHz, CDCl$_3$) δ 4.22 (tt, J=12.1, 4.2 Hz, 1H), 2.43 (dd, J=15.5, 14.8 Hz, 1H), 2.27 (dd, J=16.1, 6.5 Hz, 1H), 2.10 (dt, J=12.0, 3.4 Hz, 1H), 2.05-1.96 (m, 3H), 1.90 (dq, J=14.3, 3.7 Hz, 1H), 1.70 (td, J=12.6, 4.2 Hz, 1H) 1.55-1.33 (m, 6H), 1.12 (dd, J=9.9, 2.8 Hz, 1H), 0.96 (s, 3H), 0.96 (s, 3H), 0.89 (s, 3H).

Regioselective chlorinations of unactivated methylene C—H bonds are rare, with the few known examples involving the use of internal directing groups. In the examples herein, the regioselectivity may derive from intermolecular interactions, rather than structurally enforced positioning of the catalyst.

A possible mechanism for this new transformation is outlined in Scheme 2, below. While the details are yet to be elucidated, only the O=Mn$^{IV}$-OH porphyrin or a very similar species were observed during catalysis. Further, the C—H selectivity depended upon the nature of the porphyrin meso-substituent. It is expected that basic sodium hypochlorite will oxidize the starting Mn$^{III}$ porphyrin to a dioxo- or oxohydroxoMn$^V$ complex. Subsequent hydrogen atom abstraction from the substrate would afford an alkyl radical and a hydroxoMn$^{IV}$ complex. For the product-forming step, it is suggested that a chlorine atom transfer from the L-Mn$^{IV}$-OCl complex to the incipient carbon radical center also regenerating the reactive oxoMn$^V$ species. For this chain reaction to work, the initially formed alkyl radical must escape the [L-Mn$^{IV}$-OH.R] cage, as evidenced by the rearrangement accompanying the chlorination of norcarane. It is expected that a second ligating hydroxide, or hypochlorite anion, would lower the redox potential of the L-Mn$^{IV}$-OH intermediate under these basic conditions (pH 12 in the aqueous phase), thus slowing down the rebound rate of the alkyl radical and preventing the formation of the oxygenated products. Other axial ligands such as pyridines led to a loss of the selectivity for halogenation. Further, the formation of Mn$^{IV}$ porphyrin species during C—H oxygenation reactions has been noted recently at high pH.

Scheme 2. Proposed C—H Chlorination Mechanism

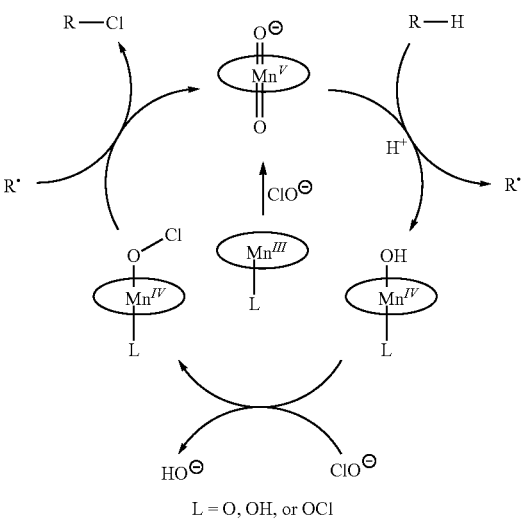

L = O, OH, or OCl

The preference for the least hindered methylene position is attributed to intermolecular nonbonded catalyst-substrate interactions resulting from the approach of the sissile C—H bond to the Mn$^V$=O(dπ-pπ)* frontier orbital. A collinear [Mn$^V$=O—H—C] transition state geometry with σ-symmetry would not explain this obvious preference for methylene sites, whereas a bent, π-approach for H-atom abstraction would result in significant interactions between the meso-aryl groups of the Mn-porphyrin catalyst and steric bulk flanking the substrate C—H bond.

The results demonstrate that highly regioselective aliphatic halogenations can be achieved predictably with catalysts as simple as Mn(TPP)Cl and Mn(TMP)Cl and halogenating agents as ubiquitous as hypochlorite or hypobromite. OxoMn$^V$ species can also oxygenate halogen ions and similar halogenations may be accessible with other oxidants.

Example 4—Additional Substrates for Halogenation

A variety of useful substrates could be halogenated with the method of halogenating provided herein. In the exemplary, non-limiting substrates below, the hydrogen indicated by an arrow may be replaced by a halogen. A hydrogen on positions adjacent to the arrows may also be replaced with halogen. The halogen may be a fluorine, chlorine or bromine.

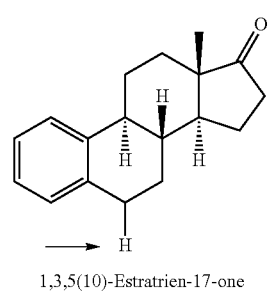

1,3,5(10)-Estratrien-17-one

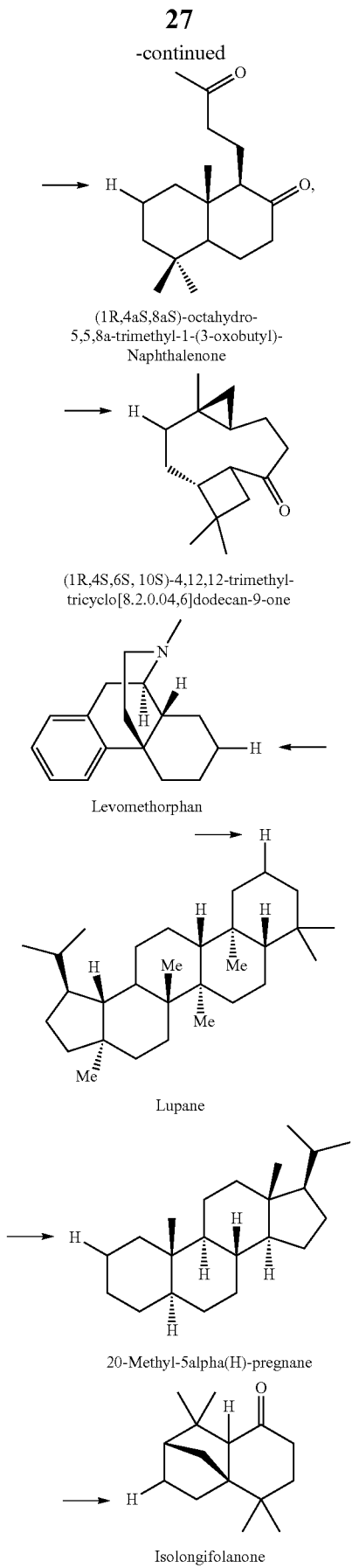
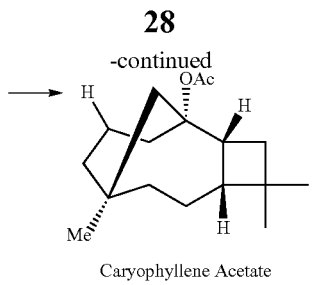

Caryophyllene Acetate

→ H = possible activated hydrogen

Exemplary simple substrates are listed above, and the method exemplified here may be utilized with other substrates. Under a nitrogen atmosphere, NaOCl (0.1-3 M, pH=9-13) could be added to a solution of manganese porphyrin (0.001-1 mmol), tetrabutylammonium chloride (TBACl, 0.005-0.5 mmol) and substrate (0.1-20 mmol) in dichlormethane in a sealed vial. The biphasic mixture could be stirred smoothly under nitrogen. Reactions could be run at ambient temperature and completion of the reaction may be indicated by disappearance of the brown red color of high valent porphyrin and formation of the green color of manganese(III) species. The catalysts may be removed by a short silica gel column eluted by $CH_2Cl_2$ and the solution analyzed by GC/MS. Yields of chlorinated products could be calculated based on oxidant added. The assignment of the products could be based on the comparison of GC retention times and fragmentation with authentic samples.

Example 5—Brominations

Substrates may be brominated by substituting hypochlorite with hypobromite. Likewise, added bromide ion may be oxidized in situ by equivalent amounts of hypochlorite to afford substrate bromination.

Example 6—Fluorinations

Alkyl chlorides and bromides obtained by any method herein can be converted to alkyl fluorides via nucleophilic substitution using literature methods. See, for example, Landini, D., Montanar, R., and Rolla, F. "Reaction of Alkyl-Halides and Methanesulfonates with Aqueous Potassium Fluoride in Presence of Phase-Transfer Catalysts—Facile Synthesis of Primary and Secondary Alkyl Fluorides" (1974) Synthesis-Stuttgart, Issue: 6, pages: 428-430, which is incorporated herein by reference as if fully set forth. Such reactions may be provided in a combination with any method described herein.

Example 7—Manganese Porphyrin Catalyzed Direct C—H Oxidative Fluorination

Figure 25:
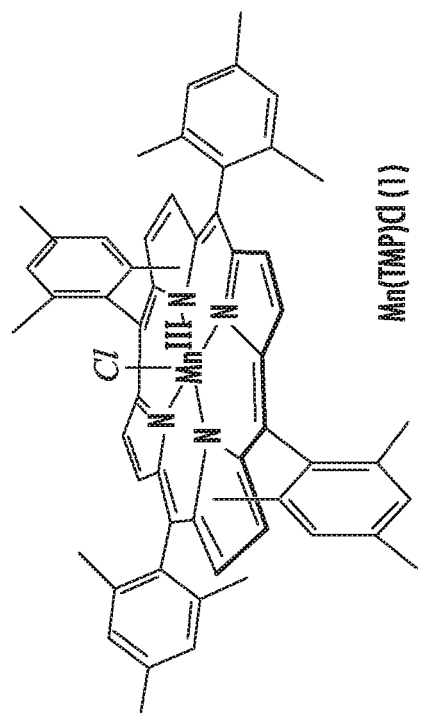
FIG. 25 illustrates a manganese porphyrin-catalyzed fluorination reaction scheme.

In the presence of mCPBA as oxidant, silver fluoride and tetrabutylammonium fluoride as fluorine source, Mn(TMP)Cl as catalyst, different substrates can be selectively fluorinated. Different cyclic alkanes can be selectively fluorinated with moderate yield. Benzylic position can be also selectively fluorinated, albeit in a poor but unoptimized yield. Examples are provided in Tables 2 and 3, below. Referring to FIG. 25, a manganese porphyrin-catalyzed reaction scheme is illustrated.

TABLE 2

Simple hydrocarbon fluorination.[a]

$$R-H \xrightarrow[\text{Mn(TMP)Cl, TBAF·3H}_2\text{O}]{\text{m-CPBA, AgF}} R-F$$

Mn(TMP)Cl

| Entry | Substrate | Product | Yield[b] |
|---|---|---|---|
| 1 | cyclooctane | fluorocyclooctane | 45% (81%) |
| 2 | cyclohexane | fluorocyclohexane | 40% (77%) |
| 3 | cycloheptane | fluorocycloheptane | 41% (73%) |
| 4 | norbornane | fluoronorbornane | 42% (79%) exo:endo = 5.7:1 |
| 5 | adamantane | 1-F and 2-F adamantane | 51% (76%) 1:1.4 |
| 6 | ethylbenzene | 1-fluoroethylbenzene | 35% (61%) |
| 7 | norcarane | fluoronorcarane + ring-opened product | 2:1[c] |

[a]Reactions run at 70° C. under N$_2$ in 4:1 CH$_3$CN/CH$_2$Cl$_2$. Substrate:catalyst:oxidant:AgF = 1:0.06:6:2.
[b]Yields based on total starting material determined by GC (yields based on converted starting material in parentheses).
[c]Identified by the characteristic m-(CH$_2$F) peak in the mass spectrum.

TABLE 3

Example Fluorinations.

$$R-H \xrightarrow[\substack{\text{Mn(TMP)Cl (6 mol \%), TBAF:3H}_2\text{O (1.5 equiv.)} \\ \text{CH3CN:CH2Cl2 = 5:1, 70° C.}}]{\text{mCPBA (6 equiv.) AgF (2 equiv.)}} R-F$$

| Entry | substrates | Product | Yield |
|---|---|---|---|
| 1 | cyclooctane | fluorocyclooctane | 45% |
| 2 | cyclohexane | fluorocyclohexane | 40% |
| 3 | cycloheptane | fluorocycloheptane | 41% |
| 4 | norbornane | fluoronorbornane | 42% exo:endo = 5.7:1 |
| 5 | adamantane | 1-F and 2-F adamantane | 51% = 1.4:1 |
| 6 | ethylbenzene | 1-fluoroethylbenzene | 21% |

Yield based on substrate

Intrigued by this unusual fluorination reaction mediated by manganese porphyrin, the regioselective chlorination with trans-decalin above as a model substrate was compared to the direct oxidative fluorination of the same compound. Interestingly, fluorination of this substrate gives similar regioselectivity as the chlorination reaction, indicating a similar C—H abstractor. Reaction of trans-decalin under the same conditions afforded methylene fluorination products with a 3.5 to 1 preference for C2 over C1 (FIG. 2A). A reactive oxo- or dioxo-manganese(V) intermediate may be responsible for abstracting a hydrogen in the reaction. Less sterically hindered manganese porphyrin catalysts were less selective.

Fluorination reactions were run under nitrogen with no precautions taken to exclude moisture. Solvents were purified according to the method of Grubbs. (A. B. Pangborn, M. A. Giardello, R. H. Grubbs, R. K. Rosen, F. J. Timmers. *Organometallics* 15, 1518 (1996), which is incorporated herein by reference as if fully set forth). 5,10,15,20-tetramesitylporphyrinatomanganese(III) chloride [Mn$^{III}$(TMP)Cl] was prepared by metallation of tetramesitylporphyrin. Iodosylbenzene was prepared by hydrolysis of iodobenzene diacetate with sodium hydroxide solution. Bicyclo[4.1.0] heptane (norcarane) was prepared according to a literature method. (Smith, R. D.; Simmons, H. E. Org. Synth. 1961, 41, 72, which is incorporated herein by reference as if fully set forth). Other purchased materials were of the highest purity available from Aldrich and used without further purification. GC/MS analyses were performed on an Agilent 7890A gas chromatograph equipped with an Agilent 5975 mass selective detector. $^1$H NMR spectra were obtained on a Varian INOVA 400 (400 Hz) or a Bruker Avance 500 (500 MHz) spectrometer and are reported in ppm using solvent as an internal standard (CDCl$_3$ at δ 7.26). Data reported as: chemical shift (δ or ppm), multiplicity (s=singlet, d=doublet, t=triplet, q=quartet, m=multiplet), coupling constant (Hz); integrated intensity. Proton decoupled $^{13}$C NMR spectra were recorded on a Bruker Avance 500 (125 MHz) spectrometer and are reported in ppm using solvents as an internal standard (CDCl$_3$ at 77.15 ppm). $^{19}$F NMR spectra were obtained on a Varian INOVA 400 (375 Hz) spectrometer and are reported in ppm by adding external neat PhF ($^{19}$F, δ –113.15 relative to CFCl$_3$)

General Procedures for Mn(TMP)Cl Catalyzed C—H Bond Fluorinations

An oven-dried 25 mL Schlenk flask equipped with a magnetic stir bar was charged with the following: the pre-catalyst, Mn(TMP)Cl (13.2 mg, 0.015 mmol, 1 mol %), TBAF.3H$_2$O (0.3 mmol), AgF (4.5 mmol, 3 equiv.), substrate (1.5 mmol) and naphthalene (internal standard, 0.5 mmol). Under these conditions the UV-vis $\lambda_{max}$ observed for (TMP)Mn$^{III}$-Cl (475 nm) changed immediately to that of a 1:2 mixture of (TMP)Mn$^{III}$-F (453 nm) and [(TMP)Mn$^{III}$(F)$_2$]-(440 nm). The flask was capped and purged with nitrogen for 5 min. Then, CH$_3$CN (1.5 mL) and CH$_2$Cl$_2$ (0.5 mL) were added by syringe and the flask was heated at 50° C. in an oil bath. Iodosylbenzene (6-15 mmol, 4-10 equivalent) was added slowly to the reaction mixture in solid form over a period of 6-15 hours. Significant decreases in yield were noted when the iodosylbenzene was added rapidly. Much shorter reaction times (1-2 hours) could be achieved at higher temperatures. With mCPBA as the oxidant, up to 40% yields could be obtained within 1 hour. Each addition of 1 equiv. oxidant was followed by Mn(TMP)Cl (13.2 mg, 1 mmol %) added dissolved in minimal amount of solvents. When the reaction was completed, the solution was allowed to cool to room temperature and was then passed through a short pad of silica gel (washing with dichloromethane). The filtrate was analyzed by GC/MS and then concentrated under vacuum. Products were separated from the reaction residue by column chromatography.

Example 8—5α-Androstan-17-One Fluorination (FIG. 26C)

Fluorine-substituted steroids, such as in flumethasone and fluasterone, have been found to be beneficial in blocking metabolic pathways (J. P. Begue, D. Bonnet-Delpon, *J Fluorine Chem* 127, 992 (2006), which are incorporated herein by reference as if fully set forth) and $^{18}$F-fluorodihydrotestosterone has shown promise as a new radiotracer for imaging prostate cancer in man. (P. B. Zanzonico et al. *J. Nucl. Med.* 45, 1966 (2004), which is incorporated herein by reference as if fully set forth). Since a direct, late-stage steroid fluorination protocol could greatly extend the applications of these important techniques, application of this manganese-catalyzed fluorination reaction to simple steroids was sought. The fluorination of 5α-androstan-17-one was examined, which contains 30 unactivated sp$^3$ C—H bonds (FIG. 2C). Analysis of this molecule suggested that the carbonyl group would electronically deactivate ring D. Rings B and C are sterically hindered, leaving the methylene groups of A ring as the most likely sites for oxidation. Consistent with this analysis, and despite of the complexity of the molecule, only the C2 and C3 positions in ring A were fluorinated in a remarkable overall yield of 48% (81% net yield based on 59% conversion). The products of the reactions could be readily assigned from the diagnostic $^{19}$F-NMR spectrum and the characteristic proton J-couplings. Notably, a 5:1 α/β diastereoselectivity was observed for both C2 and C3 positions, probably reflecting the steric effect of the axial methyl group at C10.

The reaction was run according to the general procedure above using 5α-Androstan-17-one as a substrate. After the reaction was over, the mixture was subjected to the workup protocol outlined in the general procedure and purified by column chromatography (hexanes and then 30% DCM/hexanes). The assignment of the product structures was based on the diagnostic F-NMR spectrum. 2α(–172.4 ppm, dm), 2β(–172.8 ppm, qt), 3α (–181.5 ppm, qt), 3β (–168.3 ppm, dm).

Example 9

Sclareolide fluorination: the reaction was run according to the general procedure in Example 7 above using sclareolide as a substrate. Sclareolide fluorination afforded C2 and C3 fluorinated products in a net 56% yield (FIG. 2D). C2-fluorination was favored by nearly 3:1, probably due to the steric hindrance of the gem-dimethyl groups at C4. A similar selectivity has been observed for this substrate by Baran and Eshenmoser for rhodium-catalyzed amination of sclareolide (P. S. Baran, T. Newhouse, *Angew Chem Int Edit* 50, 3362 (2011); and K. Chen, A. Eschenmoser, P. S. Baran, *Angew Chem Int Edit* 48, 9705 (2009), which are incorporated herein by reference as if fully set forth) and by White et al. for a Fe(pdp)/H$_2$O$_2$ oxidation system. (M. C. White, M. S. Chen. *Science* 318, 783 (2007), which is incorporated herein by reference as if fully set forth). After the reaction was over, the mixture was subjected to the workup protocol outlined in the general procedure and purified by column chromatography (hexanes and then 10% EtOAc/hexanes). The assignment of the product structures was based on the diagnostic F-NMR spectrum. 2α (–180.3 ppm, dm), 2β (–172.6 ppm, qt), 3α (–187.8 ppm, qt), 3β (–185.6 ppm, dm). The major 2α-fluoro isomer could be isolated a white solid on a second column chromatography. $^1$H NMR (400 MHz, CDCl$_3$) δ 4.83 (dtt, J=48.0, 11.3, 4.6 Hz, 1H), 2.45 (dd, J=16.2, 14.7 Hz, 1H), 2.27 (dd, J=15.8, 6.5 Hz, 1H), 2.12-1.85 (m, 6H), 1.70 (td, J=12.6, 4.1 Hz, 1H), 1.43-1.30 (m, 6H), 0.99 (s, 3H), 0.95 (s, 3H), 0.89 (s, 3H). 19F NMR –180.3 ppm. MS (EI) m/z cal'd C$_{16}$H$_{25}$FO$_2$ [M]$^+$: 268.2. found 268.2.

Example 10

Bornyl-acetate Fluorination (FIG. 26D): the reaction was run according to the general procedure in Example 7 above using bornyl acetate as a substrate. After the reaction was over, the mixture was subjected to the workup protocol outlined in the general procedure and purified by column chromatography using DCM:hexanes (1:4) as eluent. Reaction of bornyl acetate afforded a 55% isolated yield of the exo-5-fluoro-bornyl acetate (FIG. 2B). The characterization of the product was based on C—H correlation NMR spectroscopy and $^{19}$F-NMR spectroscopy. (L. F. Lourie et al., *J Fluorine Chem* 127, 377 (2006), which is incorporated herein by reference as if fully set forth). $^1$H NMR (500 MHz, CDCl$_3$) δ 4.71 (d, J=9.7 Hz, 1H), 4.56 (ddd, J=60, 7.6, 2.3 Hz, 1H), 2.33 (m, 1H), 1.98 (s, 1H), 1.63 (dd, J=35.3, 15.4 Hz, 1H), 0.97 (s, 3H), 0.85 (s, 3H), 0.83 (s, 3H), 0.68 (dd, J=14.5, 3.4 Hz, 1H). $^{13}$C NMR (125 MHz, CDCl$_3$) δ 95.8 (d, 186 Hz), 77.6, 50.5 (d, 17.6 Hz), 37.5 (d, 18.0 Hz), 32.2 (d, 11.1 Hz), 21.3, 20.2, 19.4, 12.6. $^{19}$F NMR −158.2 ppm. MS (EI) m/z cal'd C$_{12}$H$_{19}$FO$_2$ [M]$^+$: 214.1. found 214.1. It was anticipated that the C5 position of camphor would also be accessible, in analogy to the selectivity of P450cam (CYP101). (I. Schlichting et al. *Science* 287, 1615 (2000), which is incorporated herein by reference as if fully set forth). However, treating camphor under the standard fluorination conditions resulted in 95% recovered starting material. The low reactivity in this case is attributed to the electron withdrawing carbonyl group, which apparently deactivates the entire molecule toward fluorination.

Figure 3B:
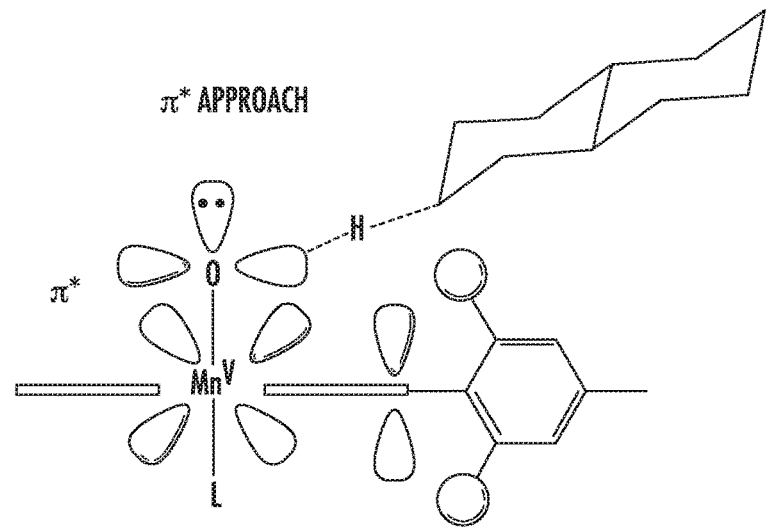

The catalytic cycle shown in FIG. 3A is suggested for this manganese porphyrin catalyzed fluorination. Oxidation of the resting Mn(TMP)Cl catalyst in the presence of fluoride ion could afford a reactive oxomanganese(V) species, O=Mn$^V$(TMP)F, which then abstracts a hydrogen atom from the substrate to produce a substrate-derived, carbon-centered radical and a HO—Mn$^{IV}$-F rebound intermediate. Fluoride binding to separately prepared Mn$^{IV}$(O)(TMP) was indicated by a UV spectral shift (423 nm to 427 nm) that was assigned to the formation of [Mn$^{IV}$(O)(F)(TMP)]-, in analogy to the well-characterized coordination of hydroxide to Mn$^{IV}$(O) (J. T. Groves, M. K. Stern. *J. Am. Chem. Soc.* 110, 8628 (1988), which is incorporated herein by reference as if fully set forth). A step in forming the fluorinated products is capture of the incipient substrate radicals either by HO—Mn$^{IV}$-F or a trans-difluoro-manganese(IV) species, which forms by reaction with AgF. The unusual methylene selectivity observed in these reactions is attributed to stereoelectronically enforced steric clashes between the substrate and the approaching oxoMn$^V$ catalyst (FIG. 3B). The LUMOs in a low-spin, d$^2$ oxoMn$^V$ complex are expected to be the two, orthogonal Mn—O π* orbitals, which would direct the approach of the scissile C—H bond into a bent π*-approach trajectory. (Jin, N.; firahim, M.; Spiro, T. G.; Groves, J. T., Trans-dioxo manganese(V) Porphyrins, J. Am. Chem. Soc. 2007, 129, 12416-12418; and Jin, N.; Lahaye, D. E.; Groves, J. T., A "Push-Pull" Mechanism for Heterolytic O-O Bond Cleavage in Hydroperoxo Manganese Porphyrins, Inorg. Chem. 2010, 24, 11516-11524, which are incorporated herein by reference as if fully set forth).

A number of experiments were conducted to examine this mechanistic hypothesis. Initial C—H hydroxylation was ruled out by controls showing that no fluorides were produced under these conditions with alcohols as starting materials. Initial C—H hydroxylation was ruled out by controls showing that cyclohexanol was oxidized to cyclohexanone under these conditions. No cyclohexylfluoride was detected. Also, the hydroxyl group of 1-methylcyclohexanol is stable to the reaction conditions (See entry 8 of Table 4, below). Deuterium kinetic isotope effects were evaluated by the reaction of a 1:1 mixture of cyclohexane and cyclohexane-d$_{12}$, producing an intermolecular competitive KIE of 6.1. A similar value (5.7) was observed with a mixture of ethylbenzene and ethylbenzene-d$_{15}$. The large KIE indicates that C—H bond cleavage is the rate-limiting step in the reaction, consistent with typical manganese porphyrins catalyzed hydroxylation reactions. Furthermore, reaction of norcarane, a diagnostic radical clock substrate, afforded 2-fluoronorcaranes and a significant amount of the rearranged fluorinated product, 3-fluoromethylcyclohexene, that is indicative of a carbon radical ring-opening process (Table 4, entry 6). The 2:1 ratio of these cyclopropylcarbinyl and homoallyl fluorides indicates a short radical lifetime of 2.5 ns, since the ring-opening rate constant for the 2-norcaranyl radical is 2×10$^8$M$^{-1}$s$^{-1}$. (J. T. Groves, *J Inorg Biochem* 100, 434 (2006), which is incorporated herein by reference as if fully set forth). Although a direct reaction between the incipient organic radical and silver fluoride cannot be ruled out at this point, the reaction between phenethyl radical, generated in situ by heating azo-bis-α-phenylethane with AgF, afforded only a trace amount of fluorinated products.

TABLE 4 manganese porphyrin-catalyzed fluorination of simple molecules.

| Entry | Substrate | Fluorination product | Entry | Substrate | Major fluorination product | Minor sites |
|---|---|---|---|---|---|---|
| 1 | cyclohexane | fluorocyclohexane (2, 49%) | 7 | methyl cyclohexanecarboxylate (COOMe) | trans-4-fluoro methyl cyclohexanecarboxylate (8, 46% dr = 6:1) | C4 14% |
| 2 | cycloheptane | fluorocycloheptane (3, 51%) | 8 | 1-methylcyclohexanol (OH) | 1-methyl-4-fluorocyclohexanol (9, 44% dr = 8:1) | C4 12% |

TABLE 4-continued manganese porphyrin-catalyzed fluorination of simple molecules.

| Entry | Substrate | Fluorination product | Entry | Substrate | Major fluorination product | Minor sites |
|---|---|---|---|---|---|---|
| 3 | cyclooctane | 4, 55% | 9 | cycloheptanone | 10, 42% | C3 11% |
| 4 | adamantane | 5, 53% 1:1.4 | 10 | F₃C-C(O)-N(Me)-cyclopentyl | 11, 51% dr = 1.5:1 | C2 < 2% |
| 5 | norbornane | 6, 49% exo:endo = 5.7 | 11 | cyclohexyl-OAc | 12a, 30% cis/trans = 1:1 | 12b, C3 27% cis/trans = 2:1 |
| 6 | norcarane | 7, 2:1* | 12 | cycloheptyl-OBz | 13, 49% dr = 1.6:1 † | C3 9% |

A trans-Mn$^{IV}$(TMP)F$_2$ (TMP: tetramesitylporphyrin), generated by ligand exchange between a hydroxyl manganese(IV) intermediate and fluoride source, was postulated to be the key intermediate that transfer fluorine to the carbon radical and make alkyl fluorides. The identification of trans-difluoroMn$^{IV}$(TMP) as the likely fluorinating agent was made possible by its isolation and structural characterization. Trans-Mn$^{IV}$(TMP)Cl$_2$, which has been characterized by Gross et al. (L. Kaustov, M. E. Tal, A. I. Shames, Z. Gross, Inorg Chem 36, 3503 (1997), which is incorporated herein by reference as if fully set forth) was chosen as the synthetic precursor of trans-Mn$^{IV}$(TMP)F$_2$. Treating Mn$^{IV}$(TMP)Cl$_2$ benzene solution with large access AgF (>50 equivalents) would lead to a color change from red to orange red within 30 minutes (FIG. 4). Pure crystals of the Mn$^{IV}$(TMP)F$_2$ were obtained by treating Mn$^{IV}$(TMP)Cl$_2$ (L. Kaustov, M. E. Tal, A. I. Shames, Z. Gross. Inorg. Chem. 36, 3503 (1997)., which is incorporated herein by reference as if fully set forth) with excess AgF. The molecular structure of this unique compound showed two axially bound fluoride ions with F—Mn$^{IV}$-F bond lengths of 1.7931(17) and 1.7968(16) Å (FIG. 3C; Tables 5-9, below). These bond lengths are very close to those of diammonium hexafluoromanganate(IV), the only other fluoromanganese(IV) species to be structurally characterized to date. (S. Kaskel, J. Strahle, Z Anorg Allgem Chem 623, 1259 (1997), which is incorporated herein by reference as if fully set forth). Mn$^{IV}$(TMP)F$_2$ could replace silver fluoride under the fluorination reaction conditions and that thermal decomposition of azo-bis-a-phenylethane in the presence of Mn$^{IV}$(TMP)F$_2$ afforded a 41% yield of 1-fluoroethylbenzene. Further, treatment of Mn$^{IV}$(O)(TMP) with fluoride ion produced a UV spectral shift (423 nm to 427 nm) assigned to the formation of [Mn$^{IV}$(O)(F)(TMP)]-, in analogy to the well-characterized coordination of hydroxide to oxoMn$^{IV}$ (J. T. Groves, M. K. Stern. J. Am. Chem. Soc. 110, 8628 (1988), which is incorporated herein by reference as if fully set forth). These observations indicate that Mn$^{IV}$(TMP)F$_2$ or the related hydroxy-fluoride may be involved in the fluorine delivery step and that the role of AgF is to replenish the manganese(IV) fluoride during turnover.

TABLE 5

Crystal data for Mn$^{IV}$ (TMP) F$_2$

| | |
|---|---|
| Empirical formula | C$_{61}$H$_{64}$F$_2$MnN$_4$ |
| Formula weight | 946.10 |

TABLE 5-continued

Crystal data for $Mn^{IV}$ (TMP) $F_2$

| | |
|---|---|
| Temperature | 100 K |
| Wavelength | Cu Kα radiation, λ = 1.54184 Å |
| Crystal system | Orthorhombic |
| Space group | Pbca |
| Unit Cell dimensions | a = 23.5969 (3) Å |
| | b = 16.1927 (2) Å |
| | c = 26.6602 (3) Å |
| Volume | 10186.8 (2) Å$^3$ |
| Z | 8 |
| Density (calculated) | 1.234 Mg/m$^3$ |
| Absorption coefficient | 2.50 mm$^{-1}$ |
| F(000) | 4008 |
| Crystal size | 0.17 × 0.10 × 0.05 mm |
| Theta range for data collection | 3.7 to 65.6° |
| Index ranges | h = −26 → 27, k = −18 → 14, l = −31 → 20 |
| Reflection collected | 38219 |
| Independent reflections | 8519 [$R_{int}$ = 0.029] |
| Absorption correction | multi-scan SADABS V2008/1 (Bruker AXS) |

TABLE 6

Structural refinement details for $Mn^{IV}$ (TMP) $F_2$

Refinement on F$^2$
Least-squares matrix: full
R [F$^2$ > 2σ (F$^2$)] = 0.052
wR (F$^2$) = 0.157
S = 1.07
Data completeness = 0.958
8519 reflections
614 parameters
3 restraints
Least-squares matrix: full
Primary atom site location: structure-invariant direct methods
Secondary atom site location: difference Fourier map
Hydrogen site location: inferred from neighbouring sites
H-atom parameters constrained
w = 1/[σ$^2$ (F$_o^2$) + (0.0739P)$^2$ + 11.7278P] where P = (F$_o^2$ + 2F$_c^2$)/3
(Δ/σ)$_{max}$ = 0.001
Δ>$_{max}$ = 0.69 e Å$^{-3}$
Δ>$_{min}$ = −0.55 e Å$^{-3}$ The X-Ray Structure was of High Quality.

The potential energy landscape and electronic structures of the intermediates and transition states proposed in FIGS. 3A-3D were explored using DFT and a polarizable continuum solvation model. Fluorine atom transfer from Mn(THP)F$_2$ to a cyclohexyl radical in the equatorial configuration was predicted to occur with a surprisingly low activation barrier of only 3 kcal/mol, very similar to the oxygen rebound barrier for hydroxylation reactions catalyzed by oxomanganese porphyrins. A slightly higher transition state was located for delivery of fluorine to a cyclohexyl radical in an axial configuration (4.2 kcal/mol). Further, the calculated barrier for fluorine transfer was ~3 kcal/mol lower for the trans-difluoroMn$^{IV}$ species (X=F) than for the analogous hydroxy-fluoride (X=OH). Thus, the manganese(IV) difluoride should react much faster with cyclohexyl radicals than its hydroxo-fluoro congener. Consistent with this low barrier for fluorine transfer, the transition state is very early in the reaction trajectory, showing an exceedingly long C—F distance of 2.48 Å and a Mn—F distance that is only very slightly elongated from the starting the manganese(IV) difluoride.

Figure 3C:
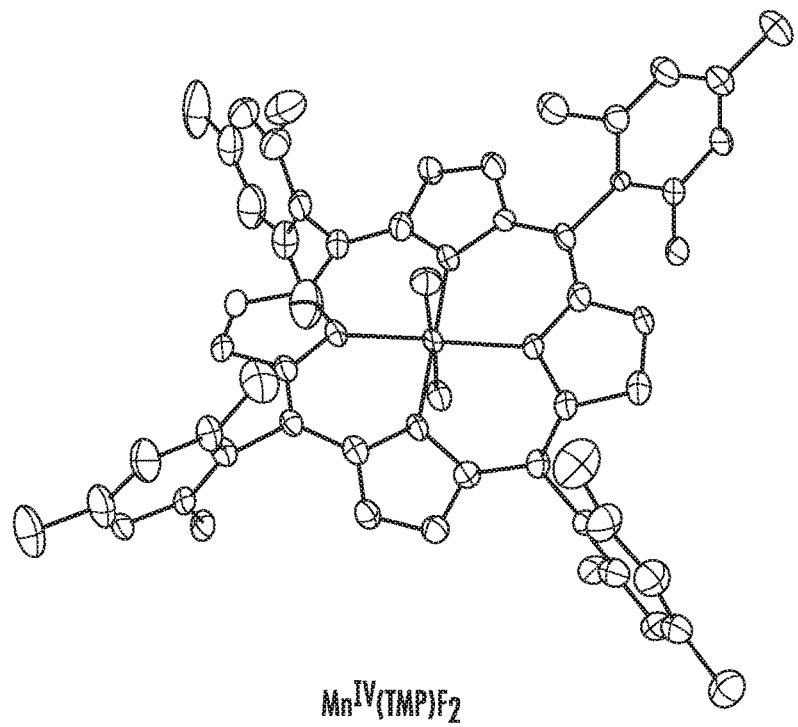
Figure 5A:
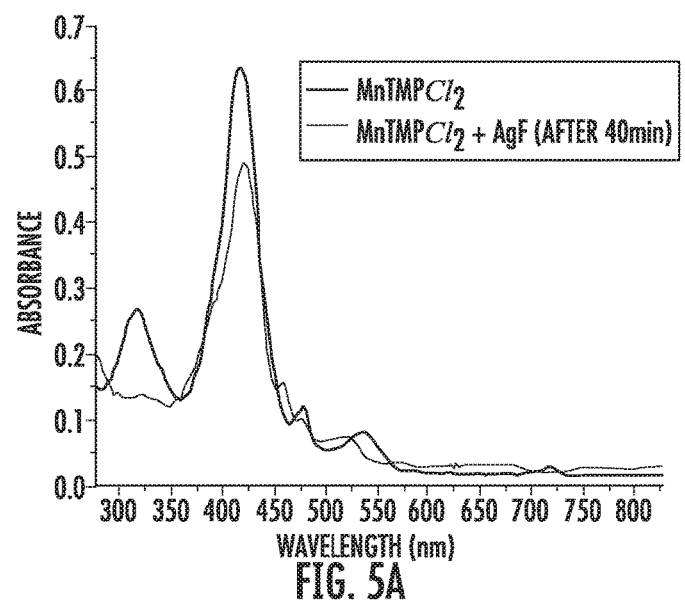
FIGS. 5A-5B.
Figure 5B:
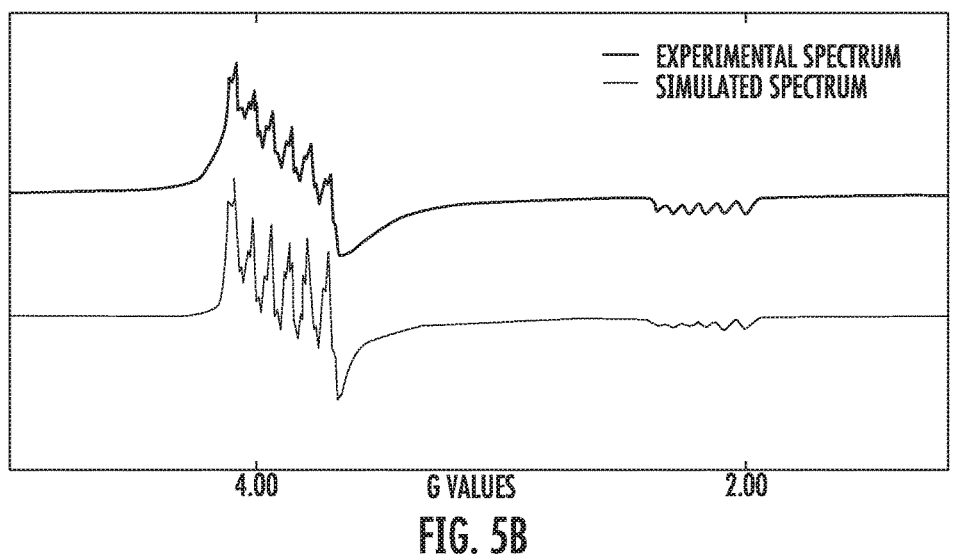

UV-vis spectrum showed that a new species with intense absorption around 420 nm, following two weaker absorptions at 520 and 680 nm appeared (FIG. 5A, upper MnTMPCl$_2$, lower MnTMPCl$_2$+AgF After 40 Min.). The EPR spectrum of the new species was shown in FIG. 5B (upper, experimental spectrum; lower, simulated spectrum). A strong signal at g≈4 and weaker signal at g≈2 is consistent with the characteristics of a high-spin d$^3$ ion with a large zero-field-splitting (ZFS) constant in an environment of axial symmetry. The six-line hyperfine splitting caused by I=5/2 $^{55}$Mn nucleus display at both g≈4 and g≈2 regions. Further triplet splitting was observed at g≈4 region, suggesting the existence of two fluorides as the axial ligands, since I=½ $^{19}$F nucleus was known to give apparent superhyperfine splitting in EPR spectroscopy. (Thuesen, C. A.; Barra, A. L.; Glerup, J. Inorg. Chem. 2009, 48, 3198, which is incorporated herein by reference as if fully set forth). The crystal structure of this new complex was acquired (FIG. 3C). Referring to FIG. 3D, selected bond lengths and angles of trans-Mn$^{IV}$(TMP)F$_2$ are illustrated. The bond length between the manganese and the axial ligands are 1.797 and 1.794 Å respectively, which is very similar to the Mn—F bond length of K$_2$Mn$^{IV}$F$_6$ (1.79 Å). (Bukovec, P.; Hoppe, R. J. Fluorine Chem. 1983, 23, 579, which is incorporated herein by reference as if fully set forth). The visible spectrum of the reaction mixture was complex, apparently due to the presence of several forms of the catalyst during turnover. However, the good yield of 1-fluoroethylbenzene from the generation of phenethyl radical in the presence of Mn(TMP)F$_2$ provides experimental support for these computational predictions that manganese(IV) fluorides are excellent radical fluorinating agents.

Figure 28:
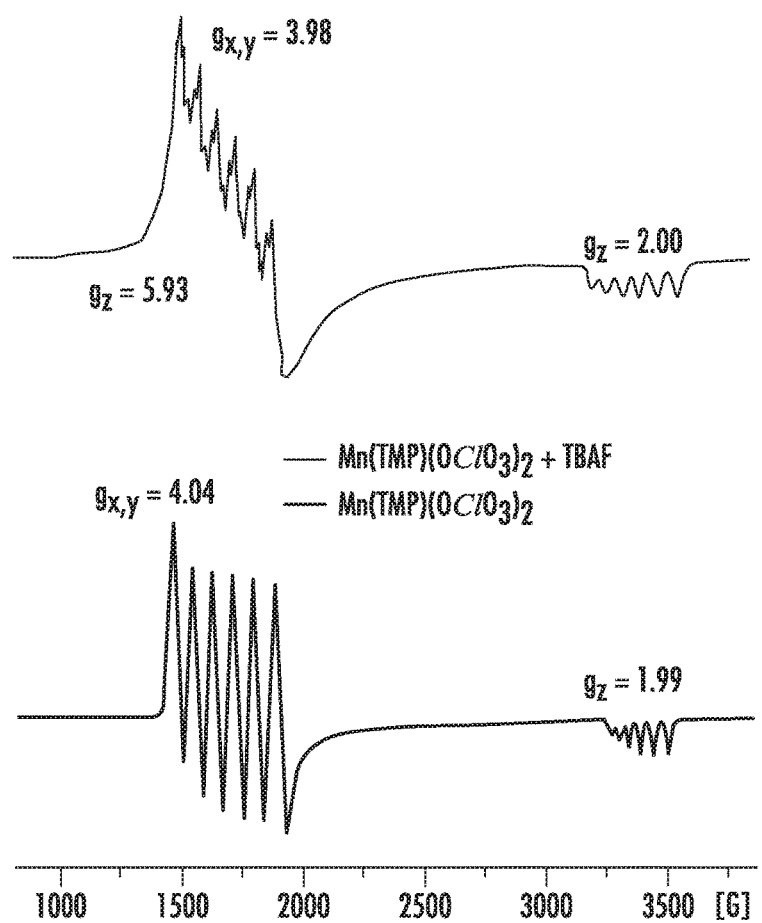
FIG. 28 illustrates an EPR spectra of $(X)_2MN^{IV}TMP$ complexes.

Referring to FIG. 28, the EPR spectra of (X)$_2$MN$^{IV}$TMP complexes is illustrated. The spectra demonstrate the presence of the rate 4+ species, which is effective as a catalyst herein.

The results described herein show selective fluorination of simple hydrocarbons, terpenoids and steroid derivatives. The yields are sufficiently high and the techniques sufficiently simple that the reaction can be performed without specialized apparatus or complicated precautions, other than normal care that should be taken whenever strong oxidants or fluoride-containing reagents are used. Given that the source of fluorine in this one-step, one-pot protocol is fluoride ion, these techniques may be readily applied to the incorporation of $^{18}$F into a wide variety of biomolecules and synthetic building blocks. Moreover, the isolation and structural characterization of the trans-difluoromanganese(IV) porphyrin, Mn$^{IV}$(TMP)F$_2$, suggest the existence of a rich chemistry of such transition metal fluorides for delivery of fluorine substituents.

Figure 6:
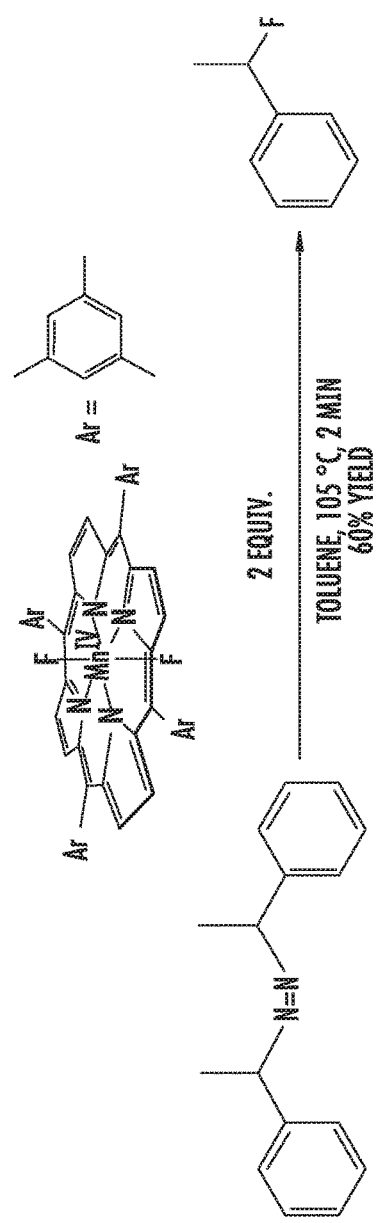
FIG. 6 illustrates the fluorine transfer of trans-Mn$^{IV}$(TMP)F$_2$ to alkyl radical.

The fluorine transfer ability of trans-Mn$^{IV}$(TMP)F$_2$ was tested using α-azobis-phenylethane as substrate (FIG. 10). Under 105° C., the corresponding alkyl fluorides can be made within 2 min with 60% yield, with the changing of trans-Mn$^{IV}$(TMP)F$_2$ to Mn$^{III}$(TMP)F. The computational study supports this observation, as it showed that the energy barrier of fluorine transfer from Mn$^{IV}$(THP)F$_2$ (THP: tetrahydroporphyrin) to a secondary alkyl radical was only 3 kcal/mol. Referring to FIG. 6, the fluorine transfer of trans-Mn$^{IV}$(TMP)F$_2$ to alkyl radical is illustrated.

A variety of simple alkanes and substituted alkanes, as well as larger natural product molecules, can be fluorinated effectively in the presence of catalytic amounts of the bulky manganese porphyrin, Mn(TMP)Cl. This oxidative aliphatic fluorination reaction is driven by iodosylbenzene as the oxo-transfer agent, using silver fluoride/tetrabutylammonium fluoride trihydrate as the fluoride source, both in stoichiometric excess. The excess of iodosylbenzene typically used in metalloporphyrin oxidations is due to the competing disproportionation of this reagent, which produces unreactive iodoxybenzene. The requirement for excess fluoride ion appears to derive from the stoichiometry of the fluorination reaction, which also produces hydroxide ions. AgF converts Mn—OH to Mn—F species and $Ag_2O$. Ultra-dry conditions are not required. Results for the initial exploratory reactions of a panel of simple substrates are presented in Table 4. Cycloalkanes afforded mono-fluorinated products in ~50% yield. Typically, conversions were ~70% with small amounts (15-20%) of alcohols and ketones also being produced. No products were detected in control experiments that omitted the manganese porphyrin or iodosylbenzene, whereas a ~2:1 ratio of oxygenated to fluorinated products was formed in the absence of tetrabutylammonium fluoride. Only oxygenated products were formed without silver fluoride. The benefit of both AgF and tetrabutyammonium fluoride apparently derives from the limited solubility of AgF in the reaction medium and the need for a higher fluoride ion concentration than can be maintained by AgF alone. The UV-vis $\lambda_{max}$ observed for (TMP)$Mn^{III}$-Cl (475 nm) changed immediately to that of a mixture of (TMP)$Mn^{III}$-F (453 nm) and [(TMP)$Mn^{III}$($F)_2$]-(440 nm) under the reaction conditions.

There were negligible amounts of difluorides produced at this level of conversion, probably due to the electron deficiency of the products induced by the fluorine atom. The high selectivity for monofluorination, the low reactivity of C—H bonds near carbonyl groups and the limited reactivity of the solvents as well as the tetrabutylammonium ion seem to reflect a very strong polar effect in the C—H bond cleavage step in this reaction.

A preliminary investigation of the substrate scope led to the results shown in Table 4 (entries 7-12). A range of substituted molecules, including ester, tertiary alcohol, ketone and amide substituents, proved to be good substrates for fluorination with Mn(TMP)Cl. Fluorination of methyl cyclohexylcarboyxlate (entry 7) and methyl cyclohexanol (entry 8) afforded trans-C3 fluorides as the major products. Mono-substituted five and seven-membered cycloalkanes (entries 9, 10, 12) were fluorinated exclusively at the C3 and C4 positions, respectively, suggesting subtle stereoelectronic effects on the selectivity of this reaction.

Having demonstrated that it is possible to redirect manganese-catalyzed hydroxylation to fluorination, we next aimed to apply this reaction to larger molecules. The reaction of trans-decalin under the same conditions afforded methylene monofluorination products with a 3.5 to 1 preference for C2 over C1 in an overall 51% yield and a 75% conversion (FIG. 26A). Very high methylene regioselectivity was observed for this substrate (>95%), similar to that observed for the manganese-catalyzed chlorination reaction we have recently reported, (Liu, W.; Groves, J. T., Manganese Porphyrins Catalyze Selective C—H Bond Halogenations, J. Am. Chem. Soc. 2010, 132, 12847-12849, which is incorporated herein by reference as if fully set forth) suggesting that a similar reactive oxo- or dioxo-manganese(V) intermediate (Jin, N.; firahim, M.; Spiro, T. G.; Groves, J. T., Trans-dioxo manganese(V) Porphyrins, J. Am. Chem. Soc. 2007, 129, 12416-12418, which is incorporated herein by reference as if fully set forth) is responsible for the hydrogen abstraction step in both reactions.

Stoichiometric amounts of $Mn^{IV}$(TMP)$F_2$ could replace silver fluoride in a single-turnover C—H fluorination of cyclooctane using Mn(TMP)Cl and iodosylbenzene. A 43% yield of cyclooctyl fluoride was obtained based on added $Mn^{IV}$(TMP)$F_2$. Thermal decomposition of azo-bis-α-phenylethane to generate the phenethyl radical in the presence of $Mn^{IV}$(TMP)$F_2$ led to a 41% yield of 1-fluoroethylbenzene. These observations indicate that after initial hydrogen abstraction, $Mn^{IV}$(TMP)$F_2$ can trap the substrate radicals in the fluorine delivery step (FIG. 3A). The moderate fluorination yields from these radical trapping experiments are probably due to the falling concentration of the manganese (IV) difluoride under these conditions. Crucial roles for silver fluoride in this scenario under catalytic conditions are first to convert the added Mn(TMP)Cl to the manganese(III) fluoride form of the catalyst and then to replenish the inventory of manganese(IV) fluoride during turnover. Although a direct reaction between the substrate radicals and AgF might also be considered, the reaction between AgF and phenethyl radicals generated in situ from azo-bis-α-phenylethane afforded only trace amounts of fluorinated products.

Example 11—Fluorination of Hydrocarbons (Table 4 Entry 1-5, FIG. 3A)

The reaction was run according to the general procedure above using the hydrocarbon listed as the substrate. When the reaction was completed, the solution was allowed to cool to room temperature and was then passed through a short pad of silica gel (washing with dichloromethane). The filtrate was analyzed by GC/MS. The assignment of the products was based on the comparison of GC retention time and mass fragmentation with the authentic samples. The products of trans-decalin fluorination were assigned by comparing the GC retention time with authentic samples, prepared by treating corresponding alcohols with DAST.

Example 12—Fluorination of Norcarane (Table 4 Entry 6)

The reaction was run according to the general procedure in Example 7 above using bicyclo[4.1.0]heptane (norcarane) as a substrate (2) and 0.5 equiv. iodosylbenzene as the oxidant. When the reaction was completed, the solution was allowed to cool to room temperature and was then passed through a short pad of silica gel (washing with dichloromethane). The filtrate was analyzed by GC/MS. The rearranged product, 3-fluoromethylcyclohexene, was identified by the characteristic m-$CH_2F$ peak in the mass spectrum.

Example 13—Kinetic Isotope Effect of the Fluorination Reaction

The reaction was run according to the general procedure in Example 7 above using cyclohexane/cyclohexane-$d_{12}$ (1:1) or ethylbenzene/ethylbenzene-$d_{10}$ (1:1) as the substrate and 0.5 equiv. iodosylbenzene as the oxidant. When the reaction was completed, the solution was allowed to cool to room temperature and was then passed through a short pad of silica gel (washing with dichloromethane). The filtrate was analyzed by GC/MS. The kinetic isotope effect was determined by calculating the ratio of corresponding peak intensities (82/92 [M-HF]$^+$ for cyclohexane/cyclohexane-$d_{12}$ and 105/114 [M-F]$^+$ for ethylbenzene/ethylbenzene-$d_{15}$).

Preparation of $Mn^{IV}$(TMP)$F_2$ $Mn^{IV}$(TMP)$F_2$ was prepared by treating $Mn^{IV}$(TMP)$Cl_2$, prepared as previously reported (P. B. Zanzonico et al., J Nucl Med 45, 1966 (2004), which is incorporated herein by reference as if fully set forth), with excess silver fluoride. In a typical experiment, silver fluoride (1.6 mmol) was added in solid form to a solution of $Mn^{IV}$(TMP)$Cl_2$ (30 mg, 0.033 mmol) in 1.5 mL benzene. The reaction was stirred vigorously at room temperature. After 2 hours, the solution was filtered to remove the insoluble silver salts, and the filtrate was concentrated under vacuum. The purple solid thus obtained was redissolved in 0.5 mL of benzene and the solution was filtered again. The solvent was removed under vacuum to afford Mn$^{IV}$(TMP)F$_2$ as a purple solid (24 mg, 84% yield). The shiny purple crystals suitable for X-ray crystal structure analysis were grown by the diffusion of a pentane layer (3 mL) into 0.5 mL benzene solution at 2° C. (Tables 5-6.

Example 14—Reaction of Azo-Bis-α-Phenylethane with Mn$^{IV}$(TMP)F$_2$

The thermal decomposition of azo-bis-α-phenylethane was conducted at 105° C. in the presence of freshly prepared Mn$^{IV}$(TMP)F$_2$. In a typical experiment, silver fluoride (1.6 mmol) was added in solid form to a solution of Mn$^{IV}$(TMP)Cl$_2$ (30 mg, 0.033 mmol) in 1.5 mL benzene-d$_6$. The reaction mixture was stirred vigorously at room temperature. After 2 hours, the solution was filtered into a 4 mL vial, and azo-bis-α-phenylethane (3 mg, 0.4 equiv) was added to the filtrate. The solution was degassed by three freeze-pump-thaw cycles and was then heated at 105° C. for 4 min. The vial was then cooled to room temperature and the yield of (1-fluoroethyl)benzene was determined by $^{19}$F NMR (δ, −167.2 ppm) using trifluorotoluene as the internal standard.

Example 15—Single Turnover Fluorination of Cyclooctane with Mn$^{IV}$(TMP)F$_2$

The single turnover fluorination reaction was carried out in the presence of Mn(TMP)Cl with Mn$^{IV}$(TMP)F$_2$ in place of silver fluoride. In a typical experiment, an oven-dried 25 mL Schlenk flask equipped with a magnetic stir bar was charged with the following: Mn(TMP)Cl (30 mg, 0.034 mmol), TBAF.3H$_2$O (0.3 mmol) and Mn$^{IV}$(TMP)F$_2$ (30 mg, 0.034 mmol. The flask was capped and purged with nitrogen for min. Then, CH$_3$CN (1.5 mL) and CH$_2$Cl$_2$ (0.5 mL) containing cyclootane (1.5 mmol) were added via syringe and the flask was heated at 50° C. in an oil bath. Iodosylbenzene (11 mg, 0.05 mmol) was added in one portion to the mixture and the reaction was stirred for 30 minutes. The solution was allowed to cool to room temperature and was then passed through a short pad of silica gel (washing with dichloromethane). The filtrate was analyzed by GC/MS and the yield of cyclooctyl fluoride (43%) was calculated based on Mn$^{IV}$(TMP)F$_2$ loaded using ethylbenzene as an internal standard. There was negligible fluorination under these conditions without Mn$^{IV}$(TMP)F$_2$.

Example 16—Table 4, Entry 7, Compound 8

The reaction was run according to the general procedure in Example 7 above using methyl cyclohexanecarboxylate as the substrate. Purification by column chromatography (hexanes and then 5% EtOAc/hexanes). The regiochemical assignment was made on the basis of the unsymmetrical $^{13}$C NMR. The stereochemical assignment was made on the basis of the obvious vicinal, trans-diaxial H—F J-coupling and small vicinal H—H couplings (δ 4.85, dtt, J=47.7, 5.7, 2.3 Hz). $^1$HNMR (500 MHz, CDCl$_3$) δ 4.85 (dt, J=47.7, 2.3 Hz, 1H), 3.61 (s, 3H), 2.67 (tt, J=11.6, 3.8 Hz, 1H), 2.11 (m, 1H), 1.89 (m, 2H), 1.72-1.38 (m, 5H). $^{13}$C APT NMR (125 MHz, CDCl$_3$) 176, 88.6, 51.8, 37.8, 33.1, 30.2, 28.1, 19.6 ppm. $^{19}$F NMR −183.0 ppm. MS (EI) m/z cal'd C$_8$H$_{13}$FO$_2$ [M]$^+$: 160.1. found 160.1.

Example 17—Table 4, Entry 8, Compound 9

The reaction was run according to the general procedure in Example 7 above using methyl cyclohexanol as a substrate. Purification by column chromatography (hexanes and then 10% ethyl acetate/hexanes). The regiochemical assignment was made on the basis of the unsymmetrical $^{13}$C NMR. The stereochemical assignment was made on the basis of the obvious J-coupling between the fluorine and the hydroxylproton, δ 2.50 (d, J=10.7 Hz). $^1$HNMR (500 MHz, CDCl$_3$) δ 4.86 (dtt, J=48.1, 5.3, 2.9 Hz, 1H), 2.50 (d, J=10.7 Hz, 1H), 1.97 (m, 1H), 1.84 (m, 2H), 1.64 (m, 2H), 1.41 (m, 3H), 1.14 (s, 3H). $^{13}$C NMR (125 MHz, CDCl$_3$) 91.6, 42.8, 38.4, 30.4, 29.7, 16.7 ppm. $^{19}$F NMR −179.2 ppm. MS (EI) m/z cal'd C$_7$H$_{13}$FO [M]$^+$: 132.1 found 132.1.

Example 18—Table 4, Entry 9, Compound 10

The reaction was run according to the general procedure in Example 7 above using methyl cycloheptanone as a substrate. Purification by column chromatography (hexanes and then 4% ethyl acetate/hexanes). The regiochemical assignment was made on the basis of the three-bond F—C2 coupling, 36.4 ppm (d, J=8.7 Hz). $^1$HNMR (500 MHz, CDCl$_3$) δ 4.75 (dtt, J=45.6, 7.4, 2.7 Hz, 1H), 2.73, (m, 1H), 2.49, (m, 1H), 2.40 (m, 1H), 2.30 (ddd, J=15.4, 9.2, 2.5 Hz, 1H), 2.08-1.76 (m, 5H). 1.58 (m, 1H). $^{13}$C APT NMR (125 MHz, CDCl$_3$) 91.7, 43.5, 36.4, 35.4, 29.7, 17.6 ppm. $^{19}$F NMR −175.3 ppm. MS (EI) m/z cal'd C$_7$H$_{11}$FO [M]$^+$: 130.1. found 130.1.

Example 19—Table 4, Entry 10, Compound 11

The reaction was run according to the general procedure in Example 7 above using N-methyl-trifluoroacetylcyclopentylamine as the substrate. Purification by column chromatography (hexanes and then 4% ethyl acetate/hexanes). The regiochemical assignment was made the on the basis of the two-bond F—C2 coupling, 36.7 ppm (d, J=22.0 Hz). The stereochemical assignments were made on the basis of the $^{19}$FNMR chemical shifts. The cis-isomer (−171.0 ppm) exhibits a smaller upfield shift than the trans-isomer (168.8) due to the shielding of the fluorine by the amide group. For trans-11: $^1$HNMR (500 MHz, CDCl$_3$) δ 5.13-4.39 (m, 2H), 2.93 (d, 3H), 2.23 (dddd, J=35.8, 15.9, 10.6, 5.0 Hz, 1H), 2.07 (m, 1H), 1.96-1.71 (m, 3H), 1.67-1.49 (m, 1H). $^{13}$C APT NMR (125 MHz, CDCl$_3$) 157.2, 116.5, 94.5, 56.4, 54.0, 36.7, 35.5, 32.9, 29.0, 27.5, 25.8 ppm. $^{19}$F NMR −68.7 (s), −70.2 (s), −168.8 (m) ppm. MS (EI) m/z cal'd C$_7$H$_{11}$FO [M]+: 213.1. found 213.1.

Example 20—Table 4, Entry 11, Compound 12a (cis)

The reaction was run according to the general procedure in Example 7 above using cyclohexylacetate as a substrate. Purification by column chromatography (1% ethyl acetate/petroleum ether). The regiochemical assignment was made the on the basis of the symmetric $^{13}$C NMR. The stereochemical assignment was made on the basis of the obvious vicinal, trans-diaxial H—F J-coupling and the small vicinal H—H coupling, δ 4.63 (dtt, J=52.1, 5.8, 2.9 Hz). $^1$H NMR (500 MHz, CDCl$_3$) δ 4.75-4.57 (m, 2H), 1.99 (s, 3H), 1.93 (m, 2H), 1.74 (m, 2H), 1.68-1.57 (m, 4H). $^{13}$C APT NMR (125 MHz, CDCl$_3$) 170.7, 88.7, 70.6, 28.9 26.6, 21.5 ppm.

$^{19}$F NMR −180.4 ppm. MS (EI) m/z cal'd C$_8$H$_{12}$O$_2$ [M-HF]$^+$: 140.1. found 140.1.

Example 21—Table 4, Entry 11, Compound 12b (cis)

The regiochemical assignment was made the on the basis of the unsymmetrical $^{13}$C NMR. The stereochemical assignment was made on the basis of the H—F J-coupling and the large vicinal H—H coupling, δ 4.48 (dtt, J=48.0, 10.1, 4.4 Hz, 1H). $^1$H NMR (500 MHz, CDCl$_3$) δ 4.65 (m, 1H), 4.48 (dtt, J=48.0, 10.1, 4.4 Hz, 1H), 2.28 (m, 1H), 2.04-1.93 (m, 2H), 1.98 (s, 3H). 1.81 (m, 2H), 1.60-1.40 (m, 3H), $^{13}$C APT NMR (125 MHz, CDCl$_3$) 170.5, 89.5, 69.9, 37.9, 31.5, 30.5, 21.4, 18.8 ppm. $^{19}$F NMR −180.4 ppm. MS (EI) m/z cal'd C$_8$H$_{12}$O$_2$ [M-HF]$^+$: 140.1. found 140.1.

Compounds 12a (trans) and Compound 12b (trans) were isolated as an inseparable mixture. $^1$H NMR (500 MHz, CDCl$_3$) δ 5.07-5.46 (m, 2H), 1.97 (s, 3H), 1.95-1.32 (m, 8H). $^{19}$F NMR −180.0, −181.1 ppm.

Example 22—Table 4, Entry 12, Compound 13

The reaction was run according to the general procedure above using cycloheptyl benzoate as the substrate. Purification by column chromatography (hexanes and then 1% ethyl acetate/hexanes) and products isolated as a mixture of cis and trans isomers. The regiochemical assignment was made the on the basis of the three-bond F—C2 coupling, 26.6 ppm (d, J=10.0 Hz). $^1$HNMR (500 MHz, CDCl$_3$) δ 7.96 (m, 2H), 7.49 (m, 2H), 7.38 (m, 1H), 5.20-4.70 (m, 2H). 2.50-1.50 (m, 10H). $^{19}$F NMR −164.6, −166.7 ppm. MS (EI) m/z cal'd C$_{14}$H$_{17}$FO$_2$ [M]$^+$: 236.1. found 236.1.

Example 23—FIG. 26B. Sclareolide Fluorination

Reaction was run according to the general procedure in Example 7 above using sclareolide as a substrate. After the reaction was over, the mixture was subjected to the workup protocol outlined in the general procedure and purified by column chromatography (hexanes and then 10% EtOAc/hexanes). The assignment of the product structures was based on the diagnostic F-NMR spectrum. 2α (−180.3 ppm, dm), 2β(−172.6 ppm, qt), 3α (−187.8 ppm, qt), 3β (−185.6 ppm, dm). The major 2α-fluoro isomer could be isolated a white solid on a second column chromatography. $^1$H NMR (400 MHz, CDCl$_3$) δ 4.83 (dtt, J=48.0, 11.3, 4.6 Hz, 1H), 2.45 (dd, J=16.2, 14.7 Hz, 1H), 2.27 (dd, J=15.8, 6.5 Hz, 1H), 2.12-1.85 (m, 6H), 1.70 (td, J=12.6, 4.1 Hz, 1H), 1.43-1.30 (m, 6H), 0.99 (s, 3H), 0.95 (s, 3H), 0.89 (s, 3H); $^{19}$F NMR −180.3 ppm. MS (EI) m/z cal'd C$_{16}$H$_{25}$FO$_2$ [M]$^+$: 268.2. found 268.2.

Example 24—FIG. 3C. 5α-Androstan-17-One Fluorination

Reaction was run according to the general procedure in Example 7 above using 5α-androstan-17-one as a substrate. After the reaction was over, the mixture was subjected to the workup protocol outlined in the general procedure and purified by column chromatography (hexanes and then 30% DCM/hexanes). The assignment of the product structures was based on the diagnostic F-NMR spectrum. 2α (−172.4 ppm, dm), 2β (−172.8 ppm, qt), 3α (−181.5 ppm, qt), 3β (−168.3 ppm, dm). The major product 3α-fluoro-5α-Androstan-17-one was isolated by a second column chromatography (4% ethyl acetate/hexanes). $^1$HNMR (500 MHz, CDCl$_3$) δ 4.75 (dm, J=48.7, 2.5 Hz, 1H), 2.37 (dd, J=19.1, 8.9 Hz, 1H), 2.01 (dt, J=19.4, 9.1 Hz, 1H), 1.85 (m, 2H), 1.73 (m, 2H), 1.60 (m, 3H), 1.53-1.32 (m, 6H), 1.28-1.09 (m, 6H) 0.95 (m, 1H), 0.79 (s, 3H), 0.74 (s, 3H). $^{13}$C APT NMR (125 MHz, CDCl$_3$) 221.6, 89.4, 54.2, 51.4, 47.8, 39.4, 35.9, 35.0, 33.9, 32.4, 31.5, 30.8, 28.0, 27.1, 21.8, 20.1, 13.9, 11.2 ppm. $^{19}$F NMR −181.5 ppm. MS (EI) m/z cal'd C$_{19}$H$_{29}$FO [M]$^+$: 292.2. found 292.2.

Figure 26D:
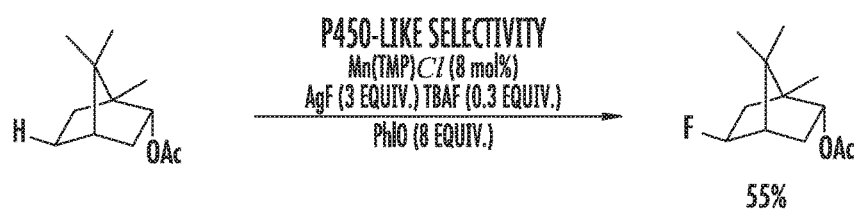

Example 25—FIG. 26D. Bornyl-acetate Fluorination

Reaction was run according to the general procedure in Example 7 above using bornyl acetate as a substrate. After the reaction was over, the mixture was subjected to the workup protocol outlined in the general procedure and purified by column chromatography using DCM:hexanes (1:4) as eluent. The product was obtained in 55% yield. Colorless oil. $^1$H NMR (500 MHz, CDCl$_3$) δ 4.71 (d, J=9.7 Hz, 1H), 4.56 (ddd, J=60, 7.6, 2.3 Hz, 1H), 2.33 (m, 2H), 2.05-1.95 (m, 1H) 1.98 (s, 3H), 1.63 (dd, J=35.3, 15.4 Hz, 1H), 0.97 (s, 3H), 0.85 (s, 3H), 0.83 (s, 3H), 0.68 (dd, J=14.5, 3.4 Hz, 1H). $^{13}$C APT NMR (125 MHz, CDCl$_3$) 95.8 (d, 186 Hz), 77.6, 50.5 (d, 17.6 Hz), 37.5 (d, 18.0 Hz), 32.2 (d, 11.1 Hz), 21.3, 20.2, 19.4, 12.6 ppm. $^{19}$F NMR −158.2 ppm. MS (EI) m/z cal'd C$_{12}$H$_{19}$FO$_2$ [M]$^+$: 214.1. found 214.1. The $^1$H-NMR splitting pattern of the proton at 4.55 (ddd) indicates that the fluorination occurred at a secondary carbon position adjacent to a methylene group. The $^{13}$C NMR spectrum displays a doublet for the C4 carbon with a coupling constant of 16 Hz, consistent with a 2J $^{13}$C—F coupling, which, together with the $^1$H NMR data, clearly designates C5 as the fluorination position. The exo-fluorine configuration was confirmed by the $^{19}$F-NMR signal at −158 ppm, whereas the endo product would have a signal at −190 ppm.

Example 26—Exemplary Fluorinations

Figure 9A:
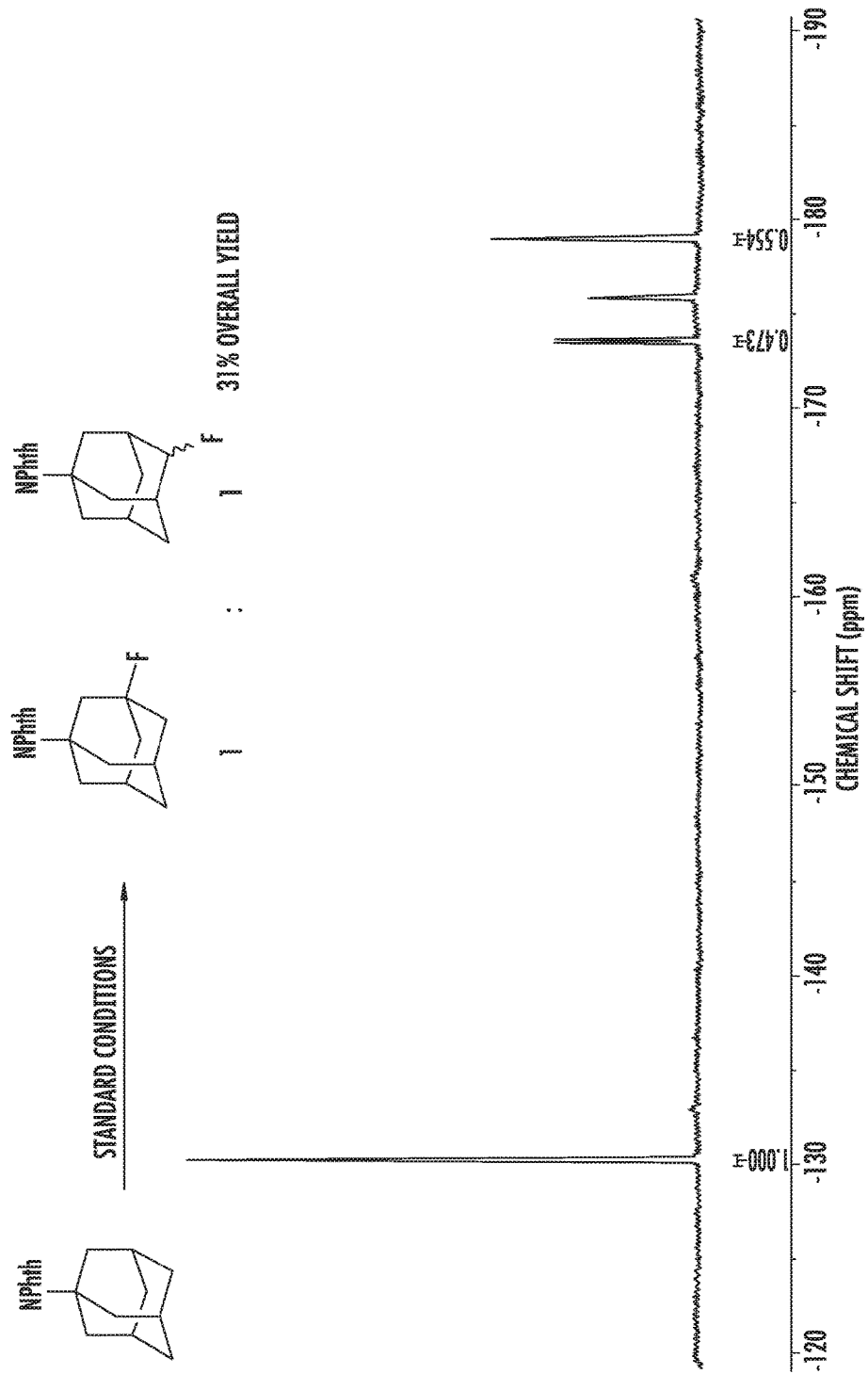
FIGS. 9A-9B illustrate fluorination of N-Phth amantadine.
Figure 9B:
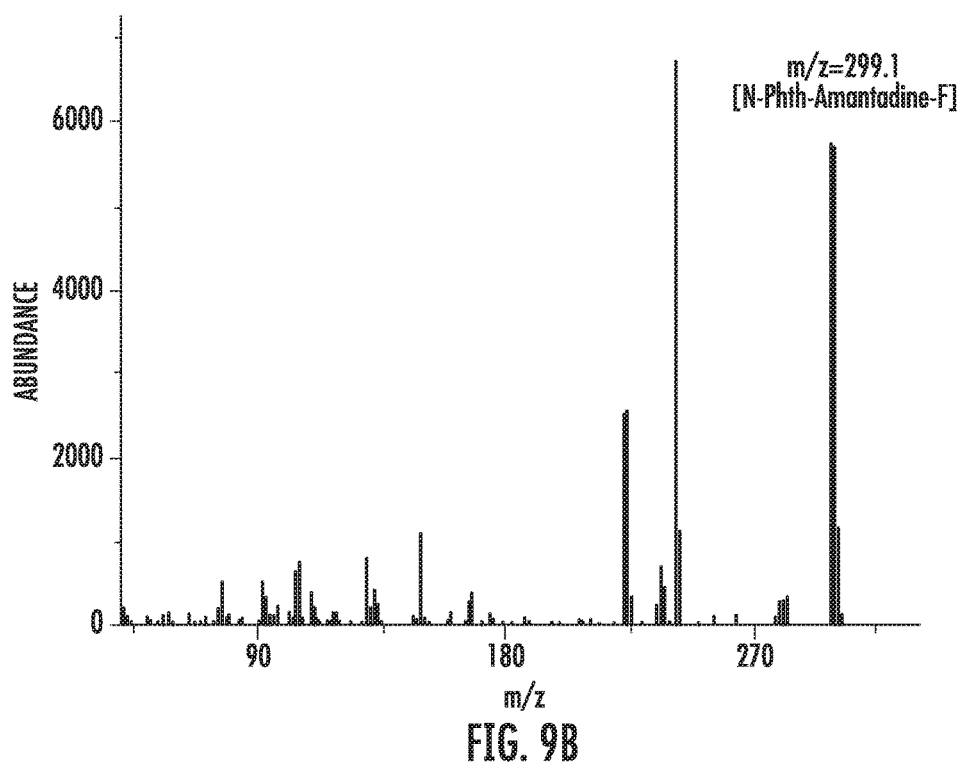
Figure 10A:
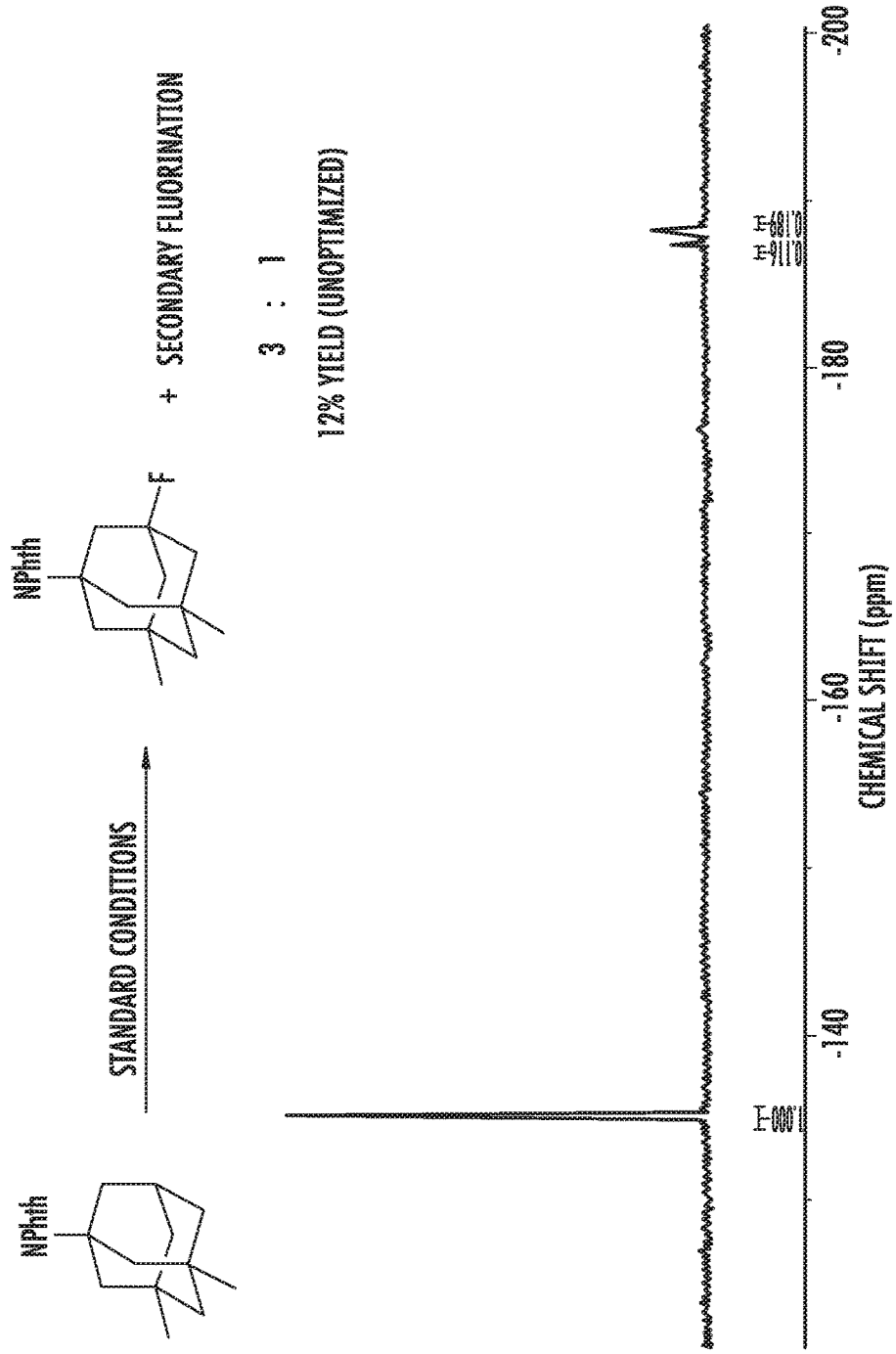
FIGS. 10A-10B illustrate fluorination of N-Phth Memantine.
Figure 10B:
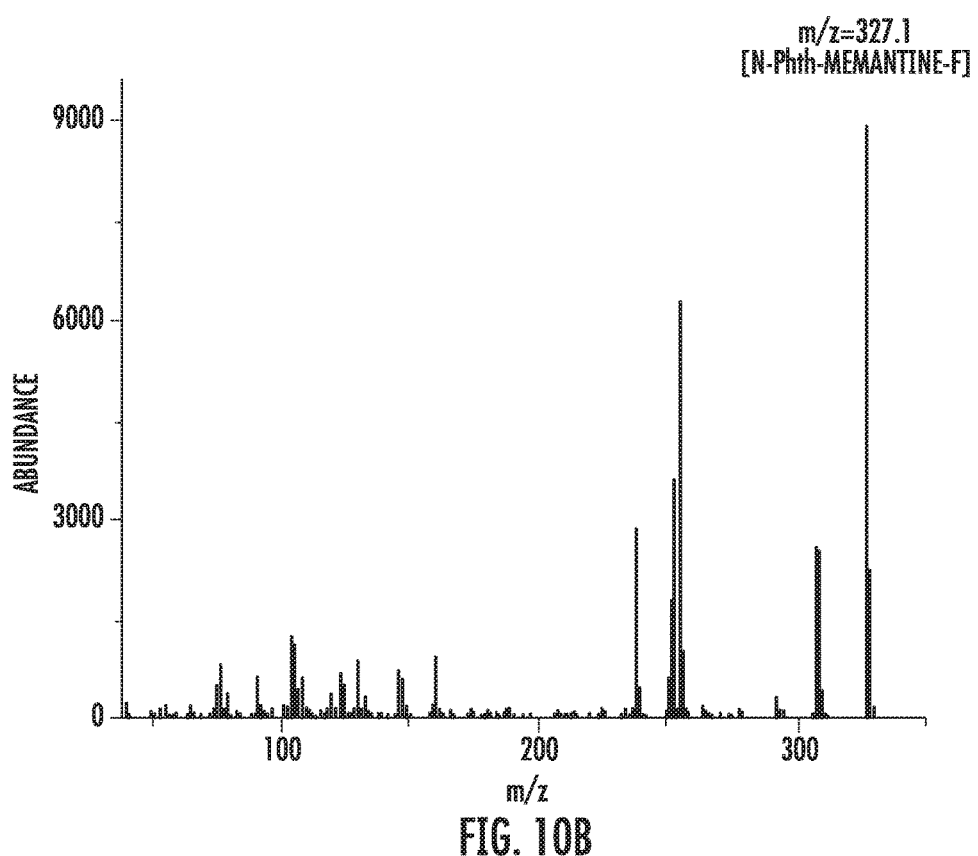
Figure 11B:
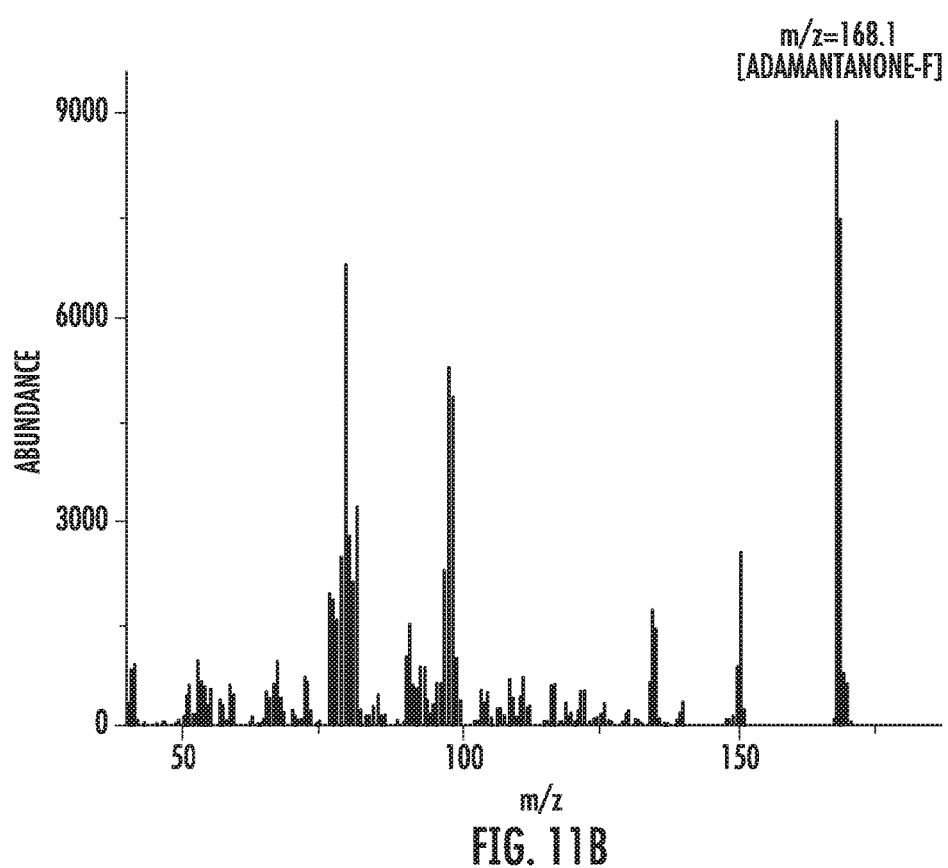
Figure 12B:
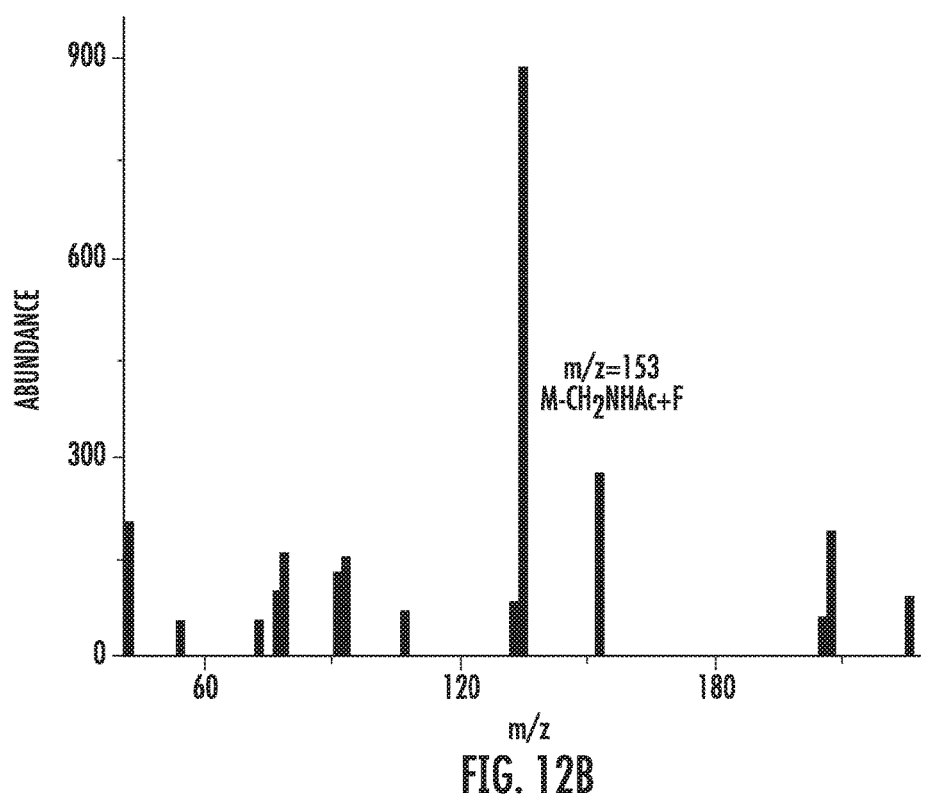
Figure 13A:
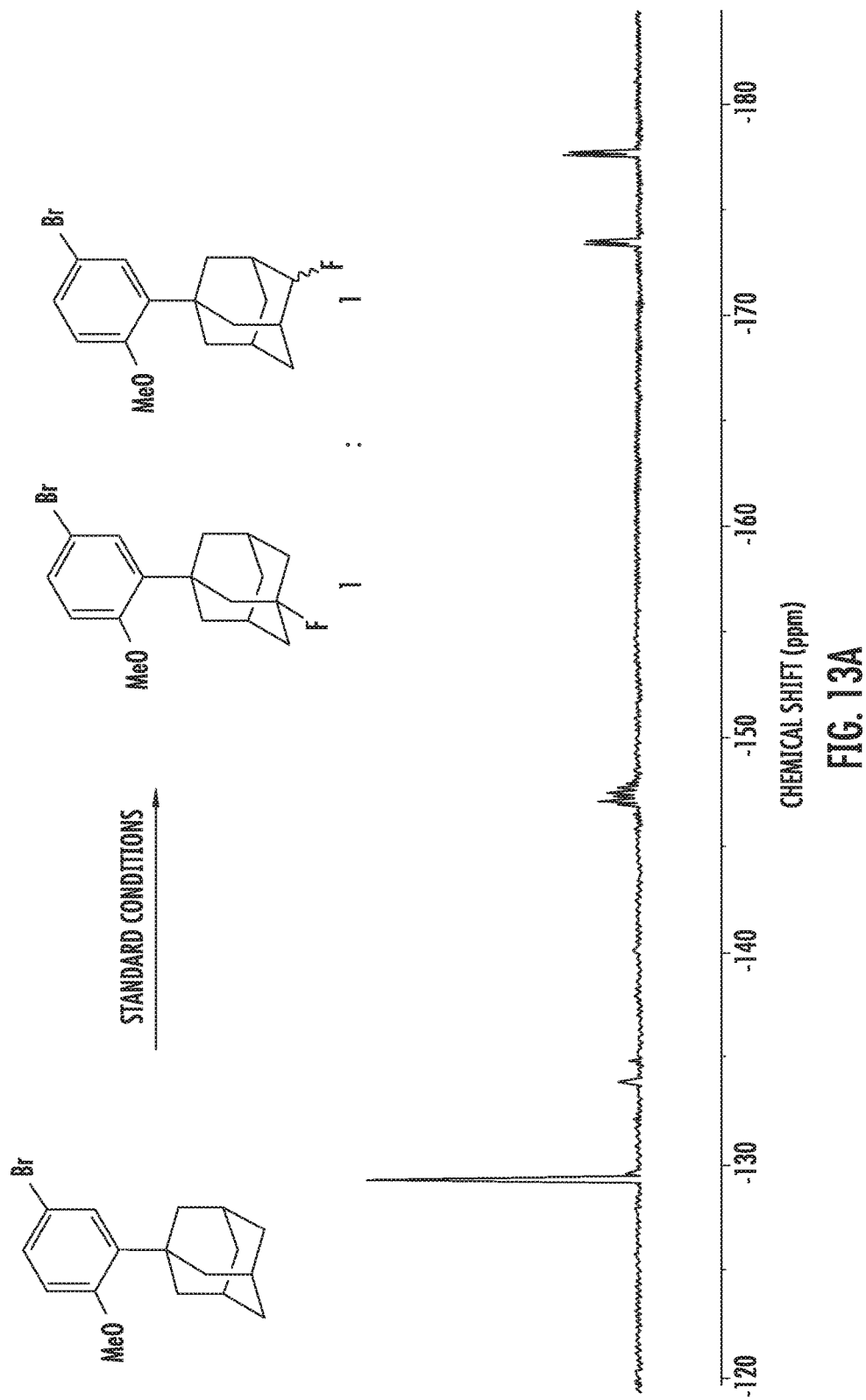
FIGS. 13A-13B illustrate fluorination of adapalene precursor.
Figure 13B:
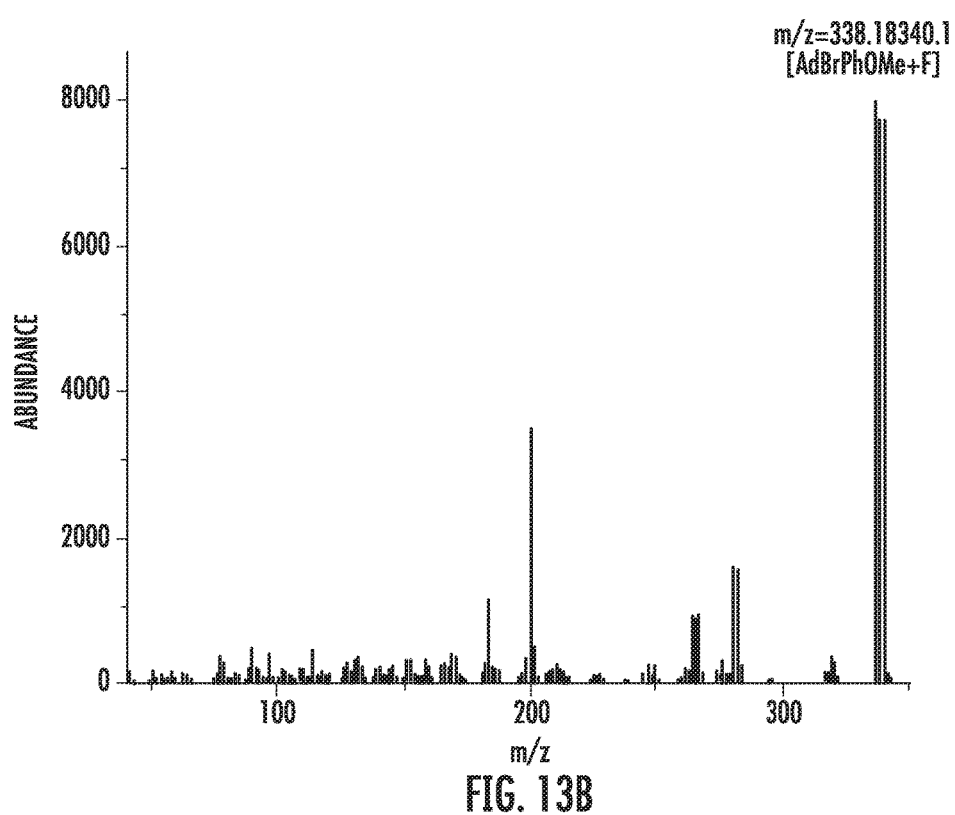
Figure 14B:
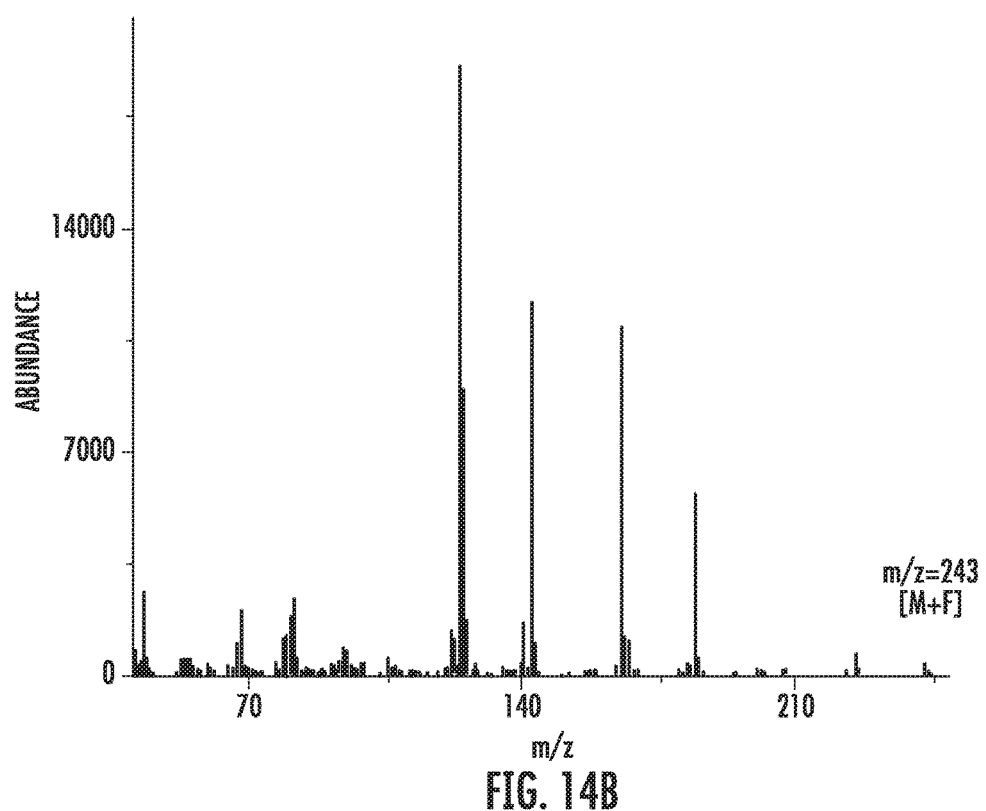
Figure 15A:
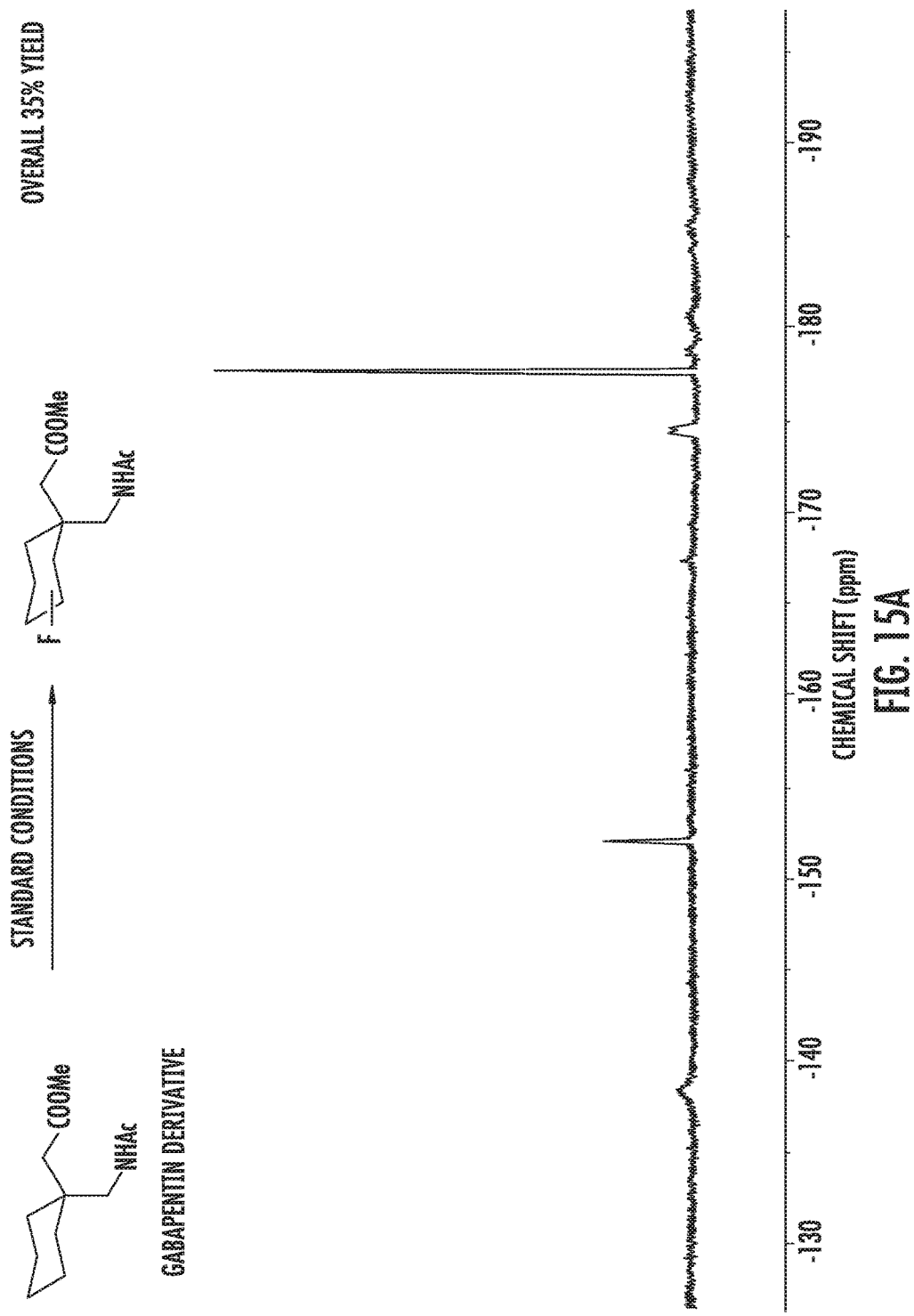
FIGS. 15A-15B illustrate fluorination of protected gabapentin.
Figure 15B:
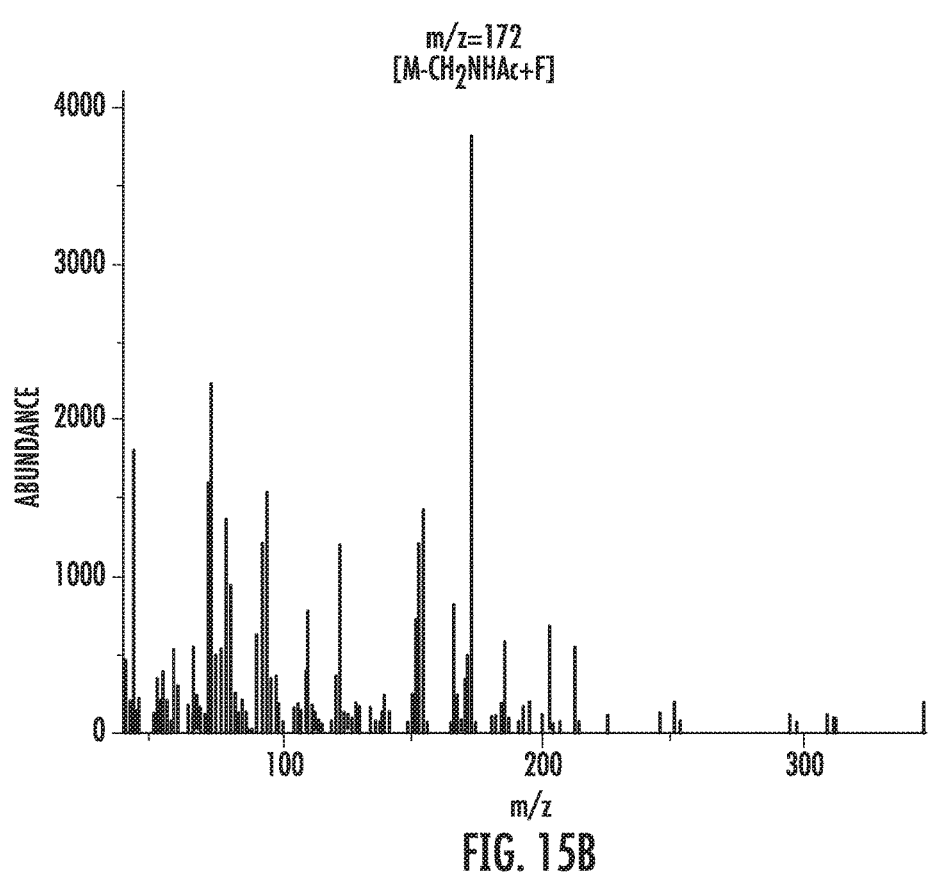
Figure 16A:
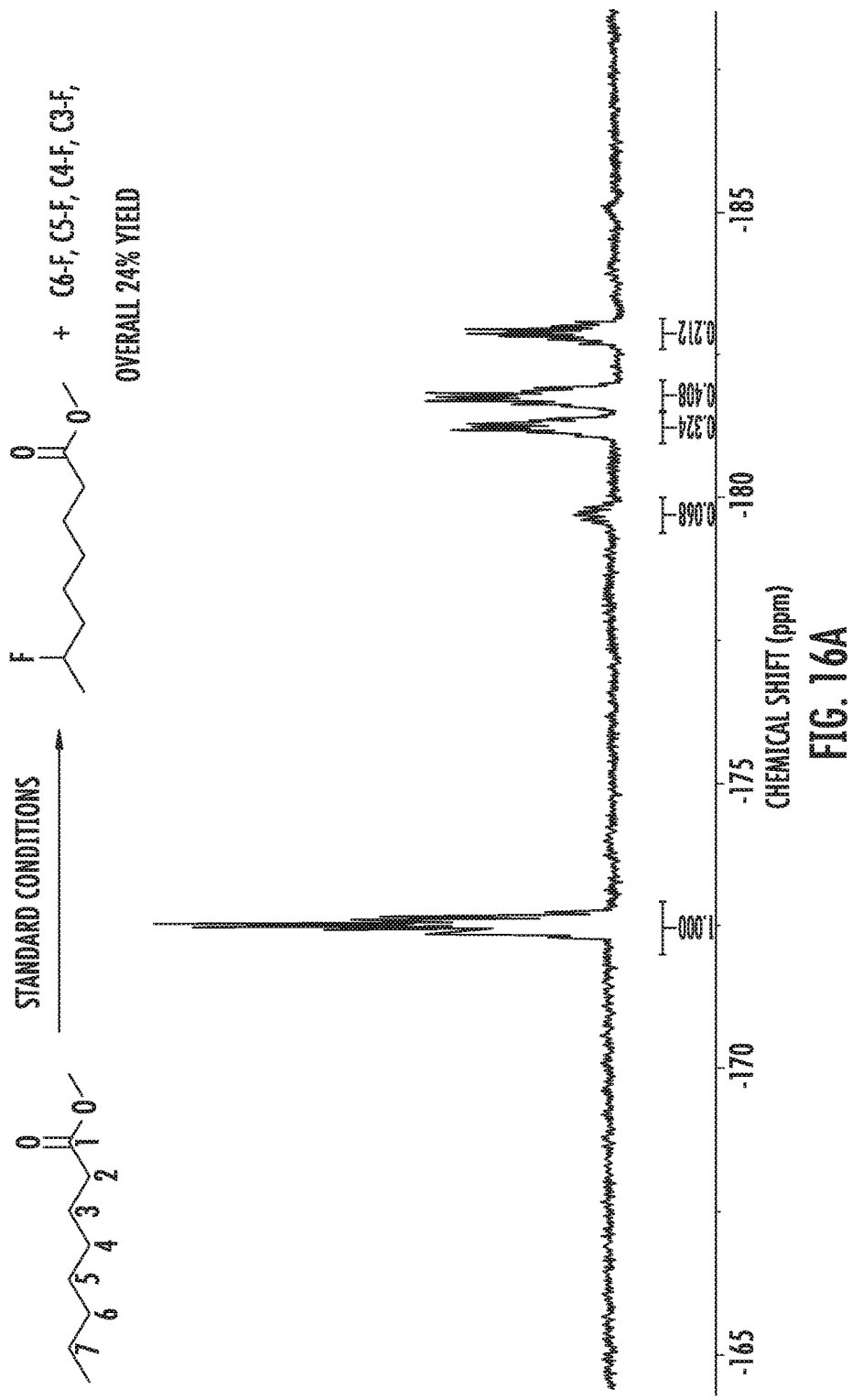
FIGS. 16A-16B illustrate fluorination of methyl octanoate.
Figure 16B:
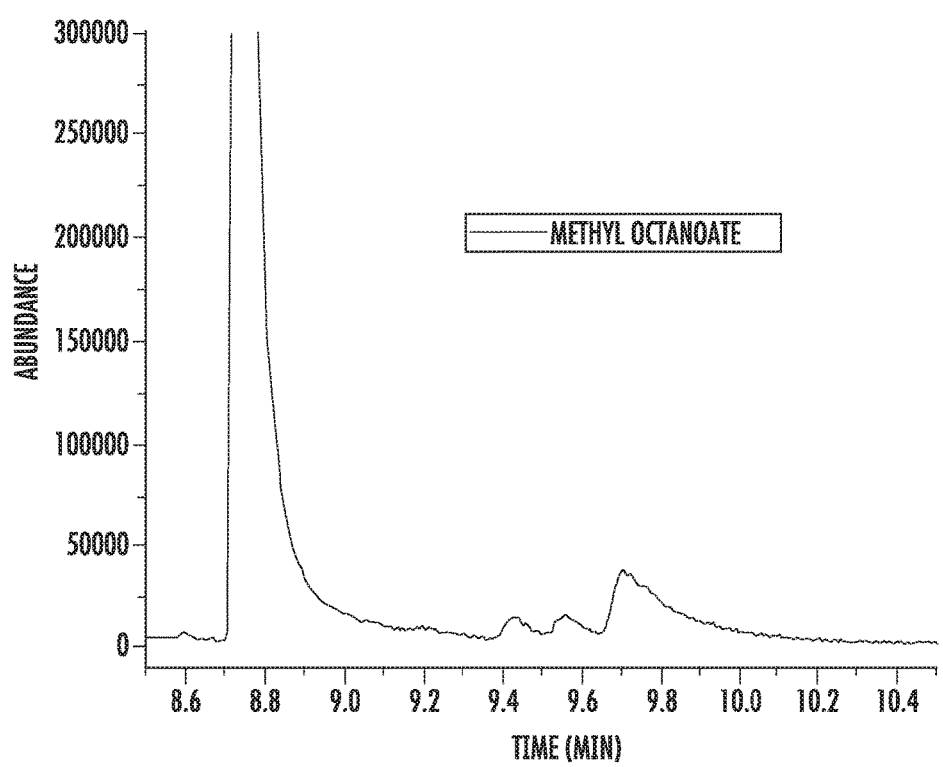
Figure 17A:
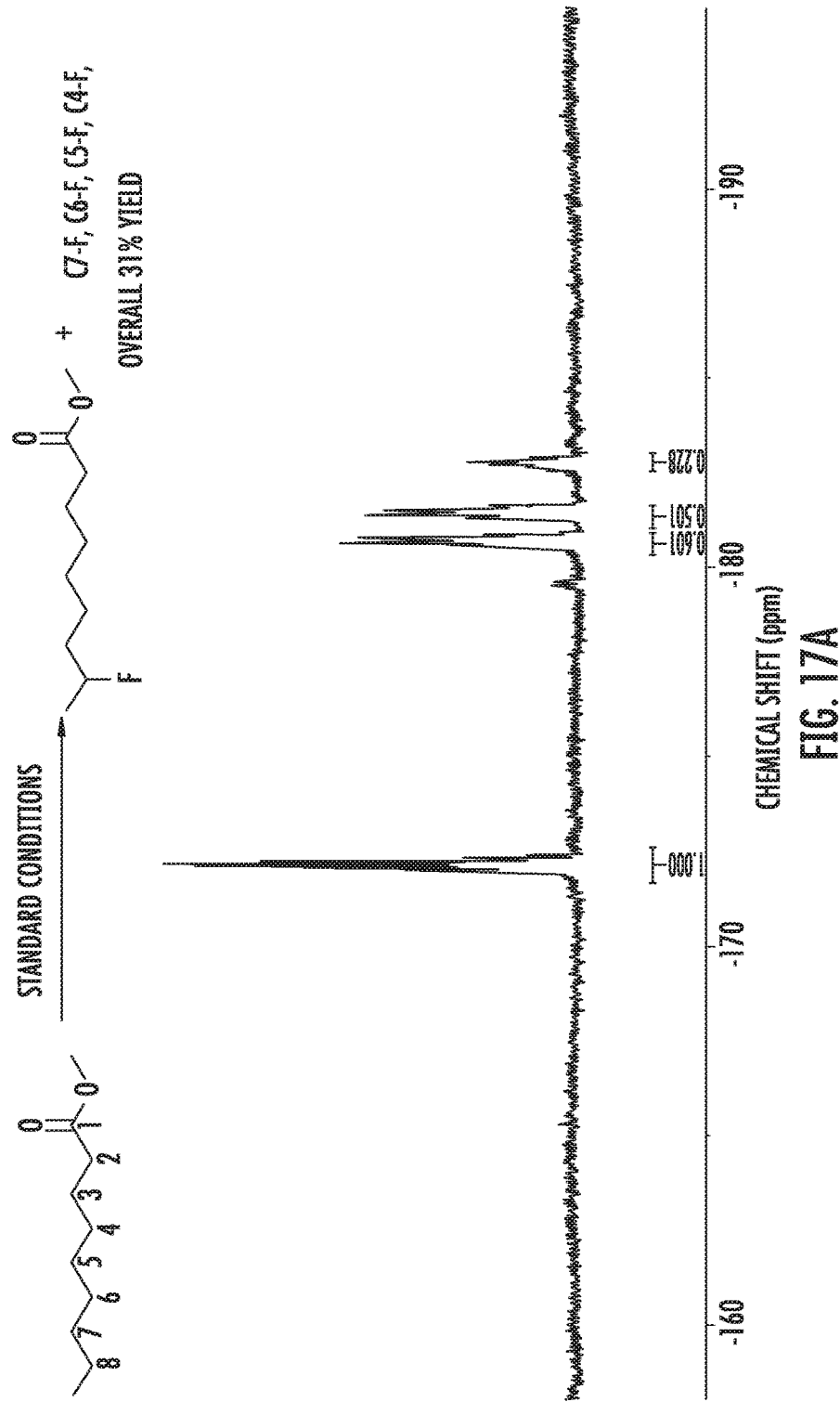
FIGS. 17A-17B illustrate fluorination of methyl nonanate.
Figure 17B:
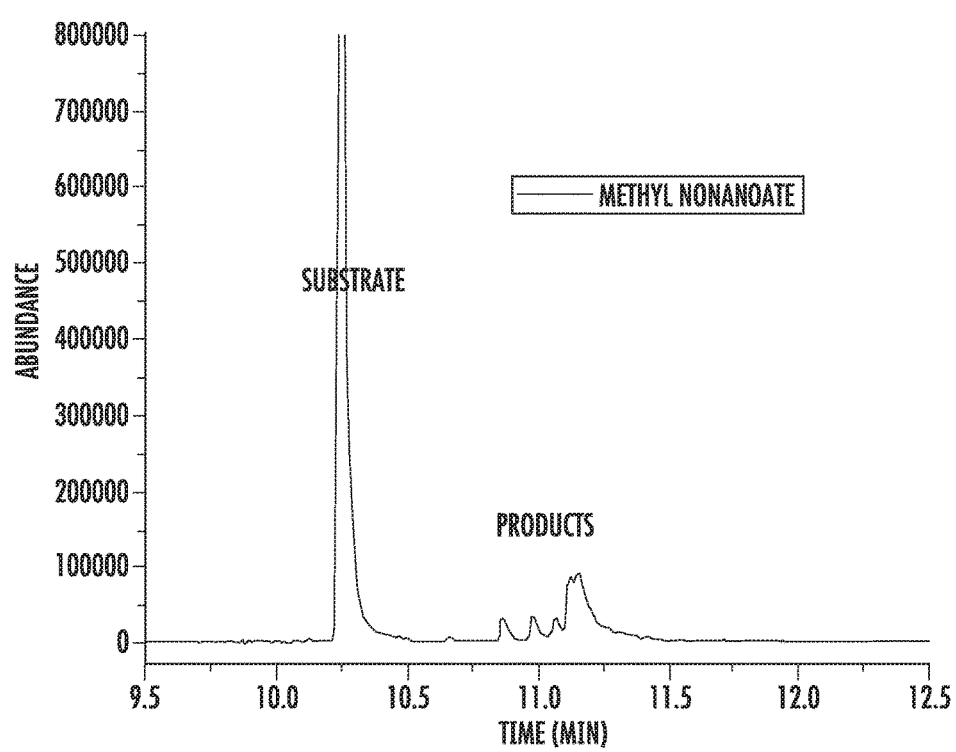
Figure 18B:
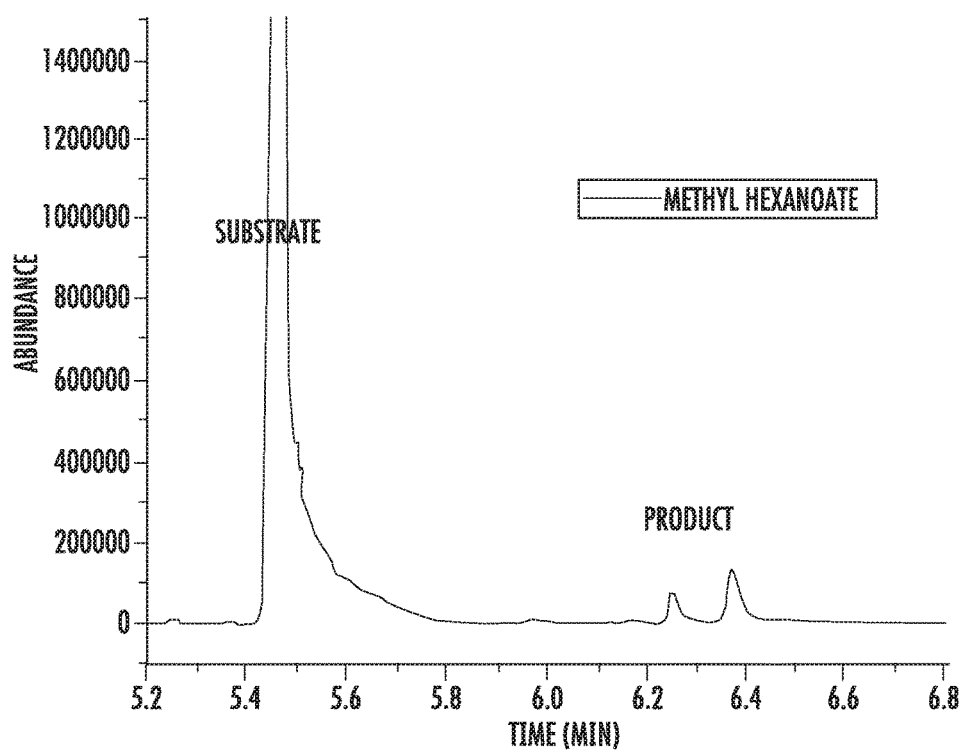
Figure 18C:
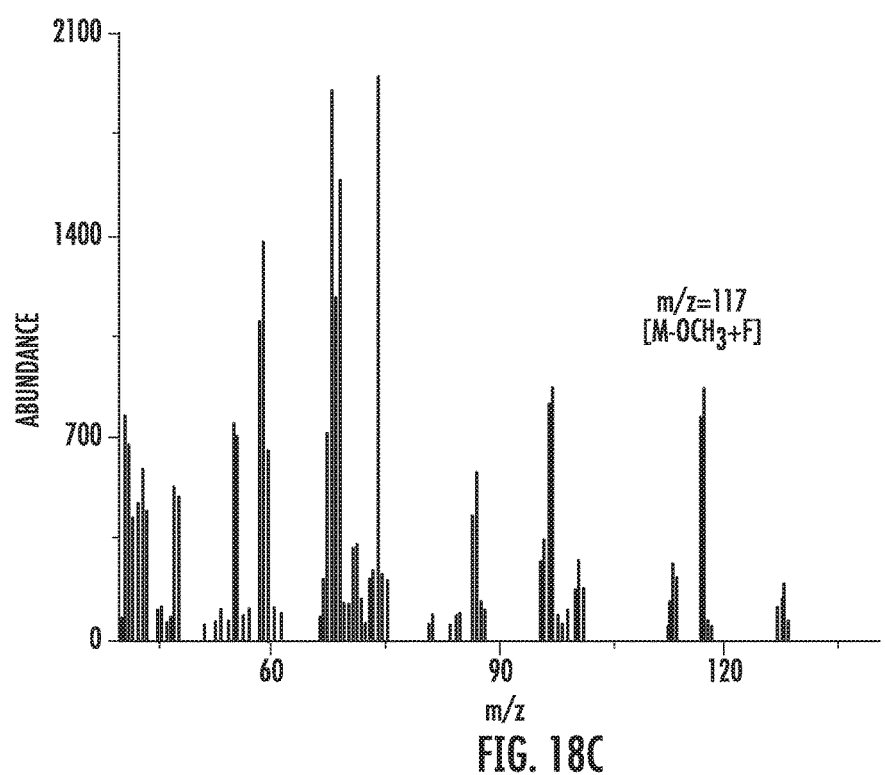
Figure 19B:
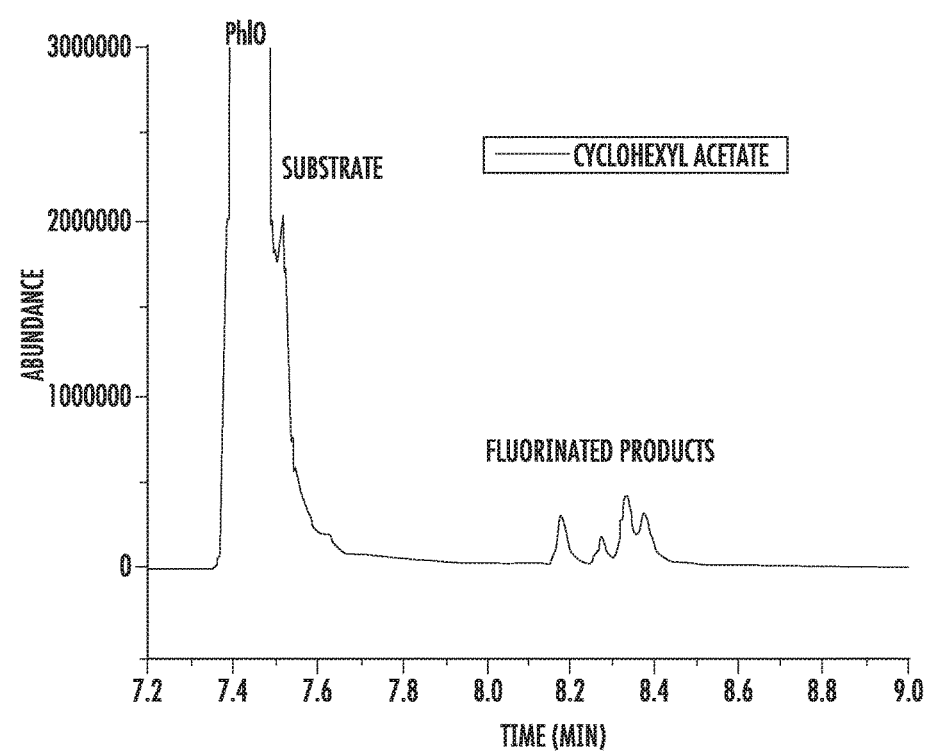
Figure 19C:
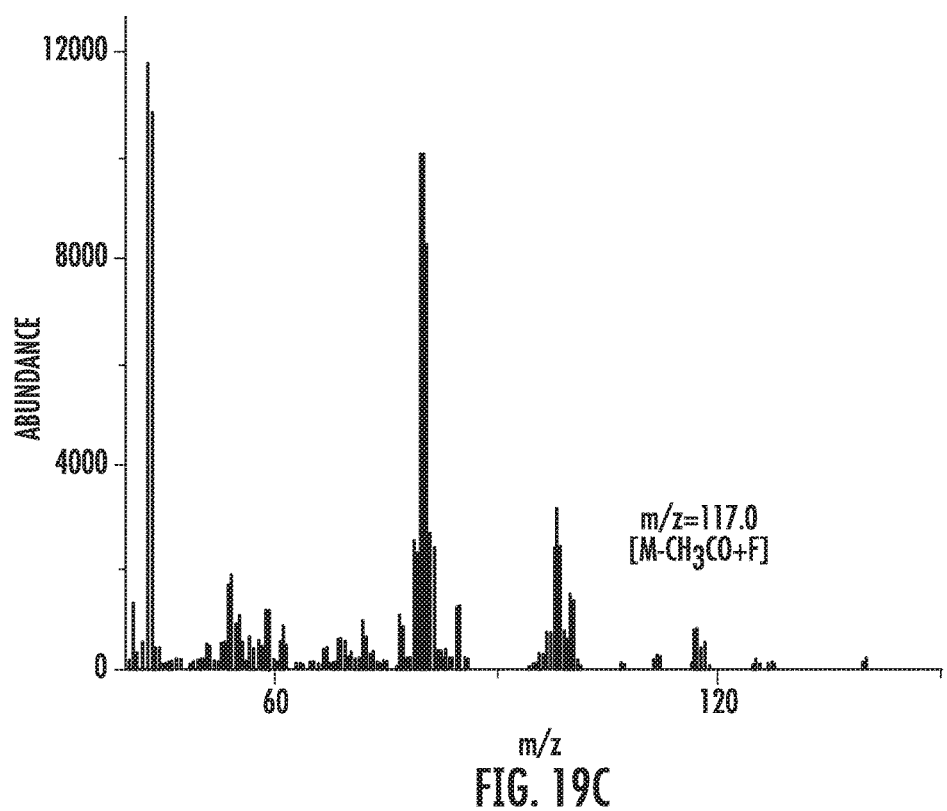
Figure 20A:
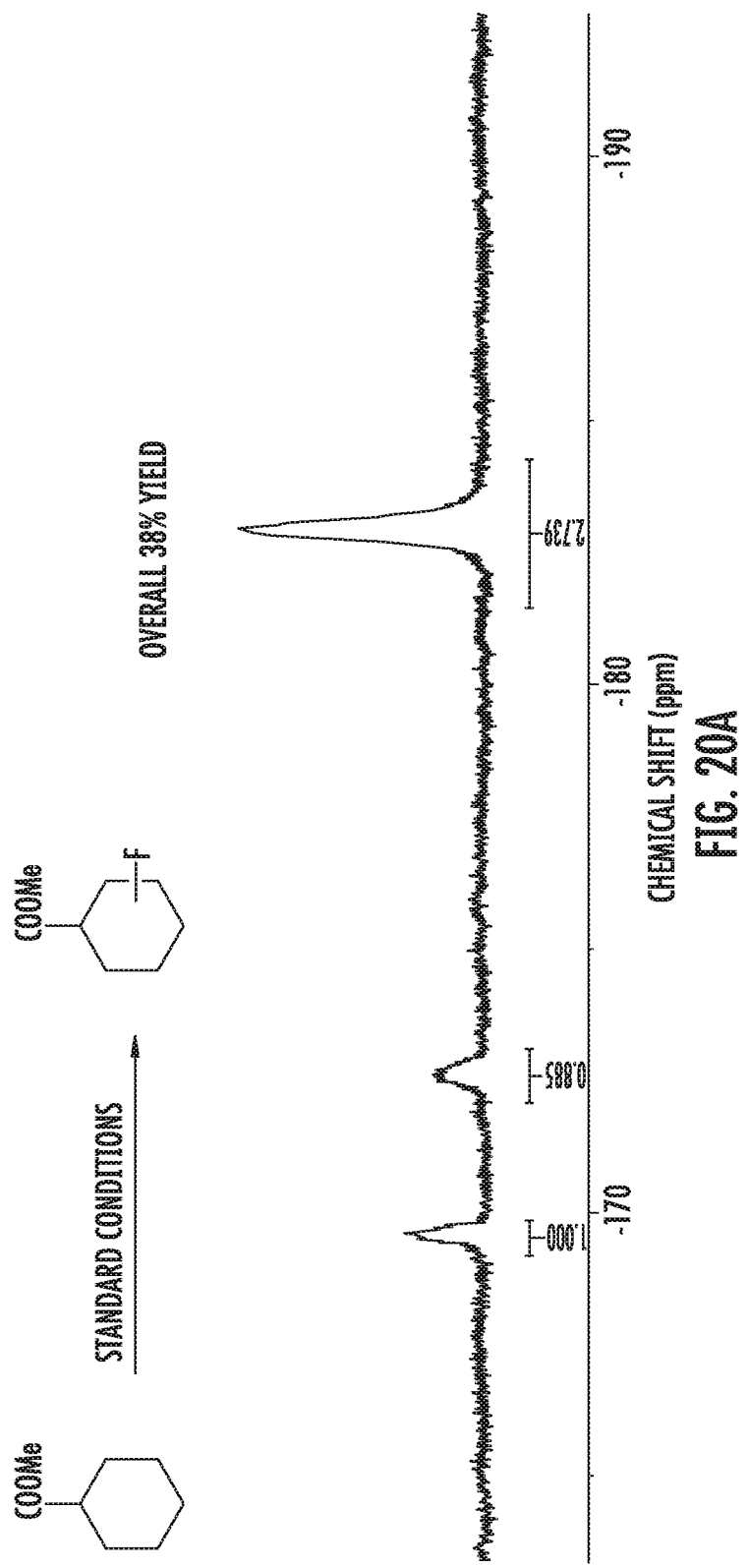
FIGS. 20A-20C illustrate fluorination of cyclohexane carboxylic acid methyl ester.
Figure 20B:
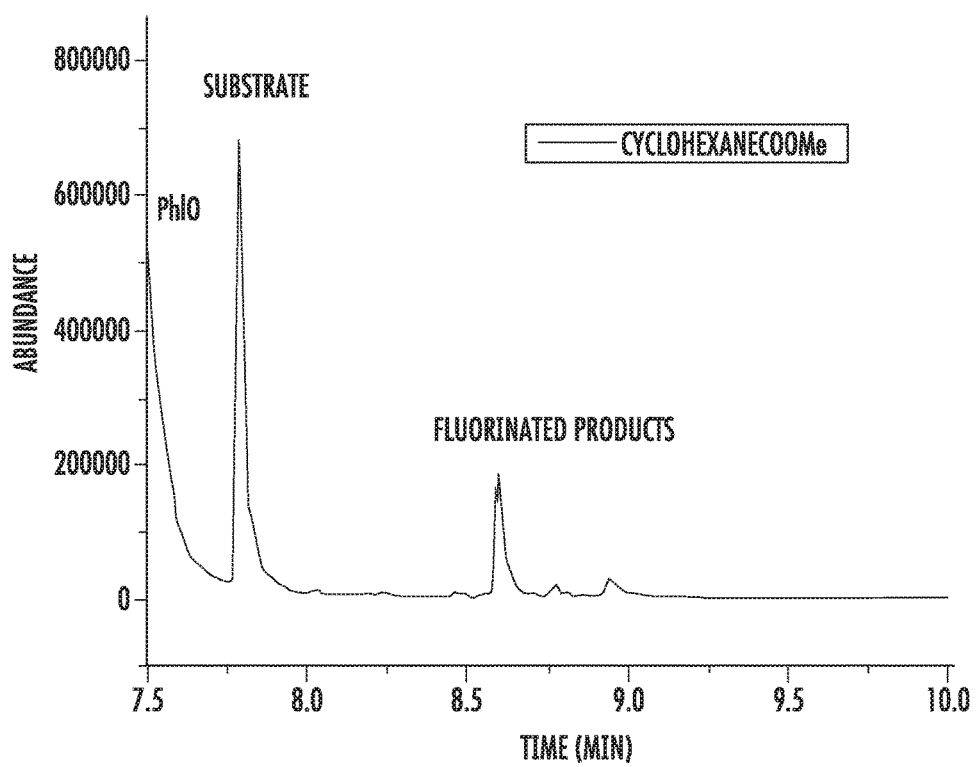
Figure 20C:
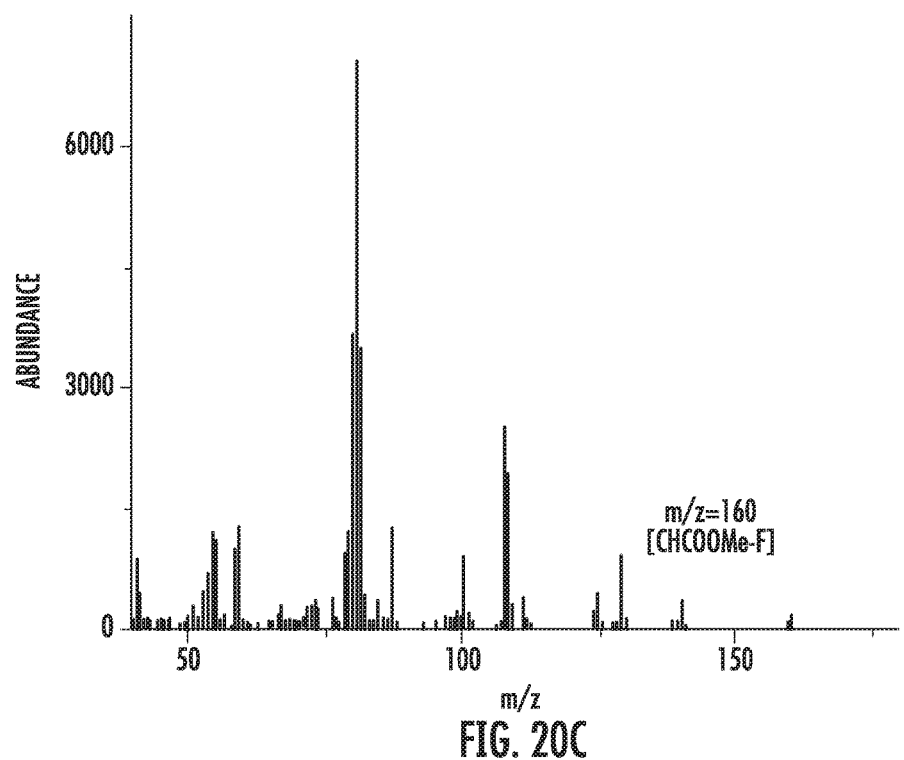
Figure 21:
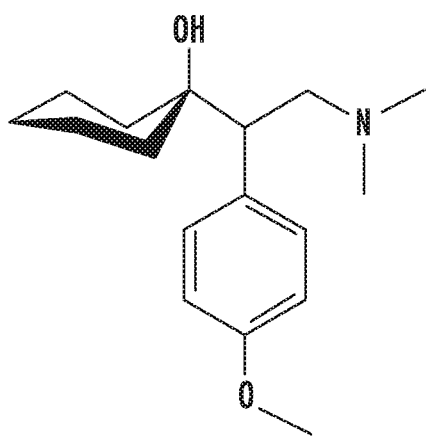
FIG. 21 illustrates lyrica (pregabalin) with venlafaxin-fluorine introduced into the cyclohexyl ring at positions C3 and C4.
Figure 22:
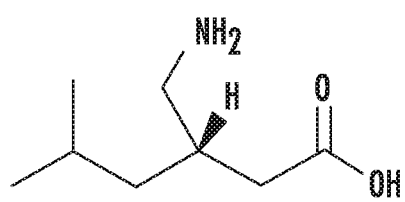
FIG. 22 illustrates fluorine introduced into the secondary and tertiary positions of the isobutyl substituent.

Referring to FIGS. 9A-9B, fluorination of N-Phth amantadine is illustrated. Referring to FIGS. 10A-10B, fluorination of N-Phth Memantine is illustrated. Referring to FIGS. 11A-11B, fluorination of 2-adamantanone is illustrated. Referring to FIGS. 12A-12B, fluorination of rimantadine analogue is illustrated. Referring to FIGS. 13A-13B, fluorination of adapalene precursor is illustrated. Referring to FIGS. 14A-14B, fluorination of perindopril precursor is illustrated. Referring to FIGS. 15A-15B, fluorination of protected gabapentin is illustrated. Referring to FIGS. 16A-16B, fluorination of methyl octanoate is illustrated. Referring to FIGS. 17A-17B, fluorination of methyl nonanate is illustrated. Referring to FIGS. 18A-18C, fluorination of methyl hexanoate is illustrated. Referring to FIGS. 19A-19C, fluorination of cyclohexyl acetate is illustrated. Referring to FIGS. 20A-20C, fluorination of cyclohexane carboxylic acid methyl ester is illustrated. Referring to FIG. 21, lyrica (pregabalin) with venlafaxin-fluorine introduced into the cyclohexyl ring at positions C3 and C4 is illustrated. Referring to FIG. 22, fluorine introduced into the secondary and tertiary positions of the isobutyl substituent is illustrated.

Example 27—Synthesis of Fluoro-Buspirone

Figure 7B:
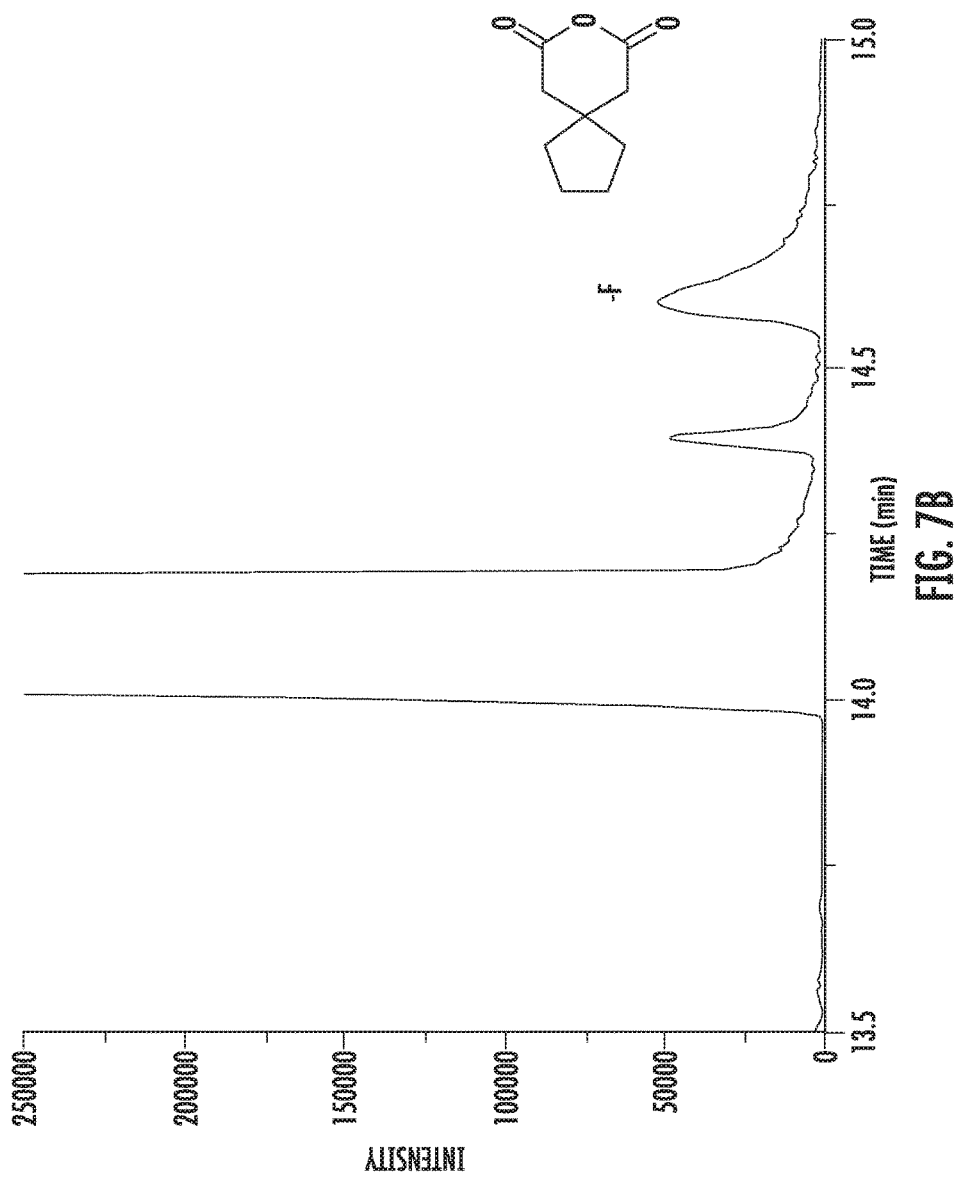
Figure 7C:
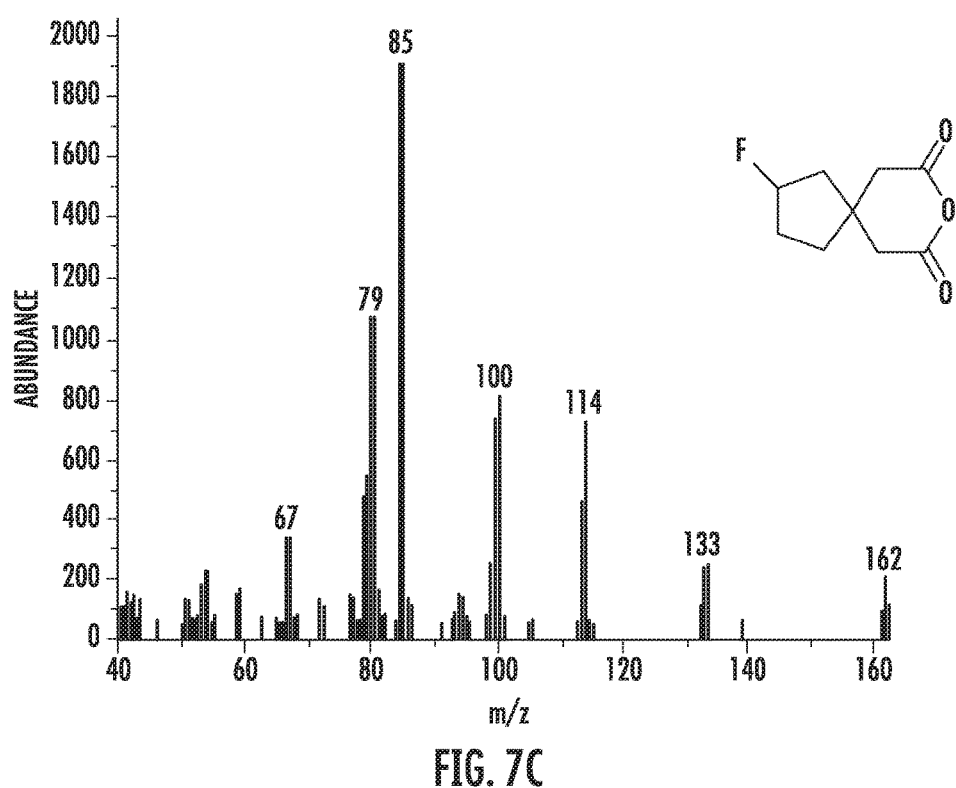
Figure 7D:
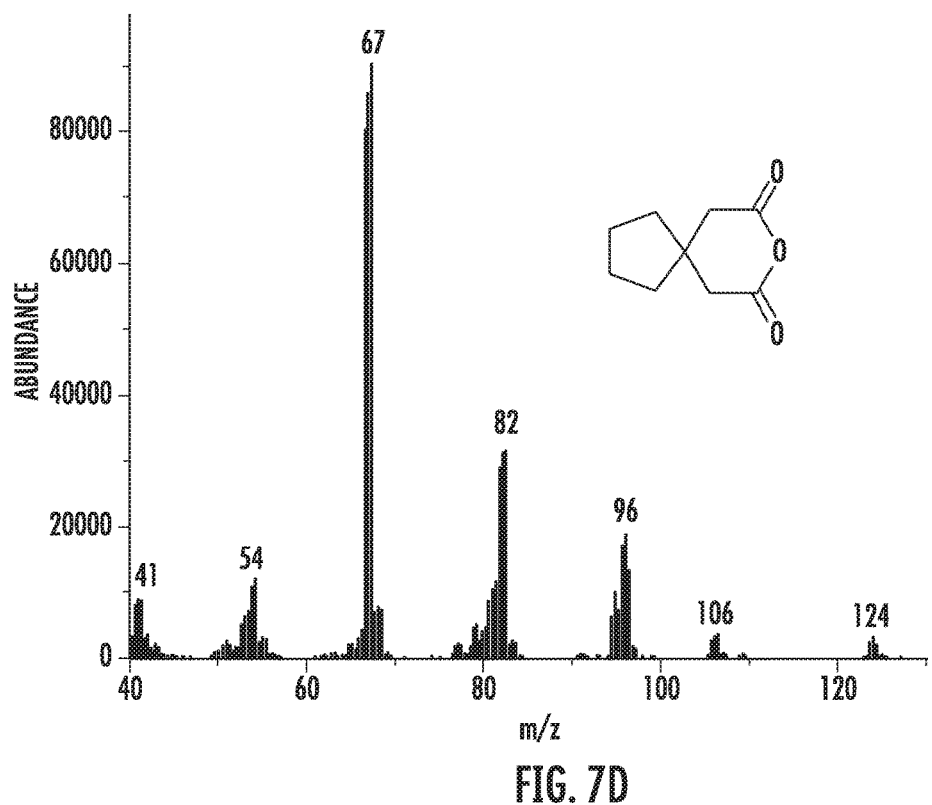

The parent drug, Buspirone (brand name Buspar) is a psychoactive drug and pharmaceutical medication of the piperazine and azapirone chemical classes. It is used primarily as an anxiolytic, specifically for generalized anxiety disorder. Bristol Myers Squibb gained FDA approval for buspirone in 1986 for generalized anxiety disorder, and it became available as a generic in 2001. Referring to FIG. 7A, the fluorinated buspirone derivative is illustrated. FIG. 7B illustrates that fluorination of buspirone precursor affords fluorinated product with another unknown product. Referring to FIG. 7C, the mass spectrum of the fluorinated buspirone peak is illustrated. Referring to FIG. 7D, the mass spectrum of the buspirone precursor starting material is illustrated. The fluorinated derivative described here appears to be a new composition of matter. A large proportion of new drugs are fluorinated in particular places both the affect binding to their targets and to decrease the incidence of toxic metabolism. This new method produces a novel fluorinated derivative of the generic drug. There are at present few if any ways to incorporate fluorine atoms selectively into complex compounds. In this case we have incorporate fluorine into an otherwise inaccessible part of the molecular scaffold of this drug. The new fluorination technology previously described has been employed to incorporate fluorine either into the immediate anhydride precursor of buspirone and directly into the drug itself. The fluorine is located in the five-membered ring.

Example 28—Decarboxylative Fluorination Reaction

Figure 29:
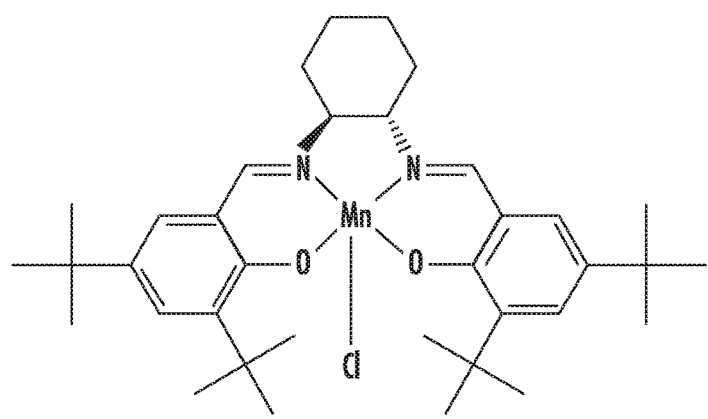
FIG. 29 illustrates a manganese salen catalyst.

Since C—H fluorination can also be achieved at room temperature, reaction conditions under room temperature were searched. Cumene-like 2-methyl-2-phenylpropanoic acid was chosen as the substrate for reaction optimization. Initial investigation showed that in the presence of excess TBAF (the same as C—H fluorination conditions, about 30 equiv vs. catalyst), white solids would precipitated and the whole reaction solution became slurry. Accordingly, only trace amounts of fluorinated product could be detected by GC-MS under those conditions. This was attributed to the deprotonation of carboxylic acids aided by the large amount of basic TBAF, which then facilitated the formation of silver carboxylate and prevent the activation of carboxylic acids by oxomanganese porphyrin. The amount of TBAF was then decreased to 5 equiv vs. catalyst. Significantly, the yield of fluorination product was increased to 18% (based on oxidant, the same below), with 8% of desaturation product and less than 1% oxygenated product (FIG. 29). Control experiments omitting the manganese porphyrin showed no detectable fluorination product by GC-MS, suggesting the crucial importance of manganese porphyrin catalyst. The decarboxylative fluorination reaction based on the manganese porphyrin system will be very promising to be a powerful tool of fluorination. It appears that the unique and unprecedented manganese(IV) difluoride (Mn(TMP)F$_2$) isolated and structurally characterized is the fluorinating catalyst. This is the first catalytic decarboxylative fluorination system to be reported to date. The reaction conditions are very mild and the yield may be largely increased by further optimized the reaction conditions.

Example 29—Additional Halogenating Catalysts

Figure 23A:
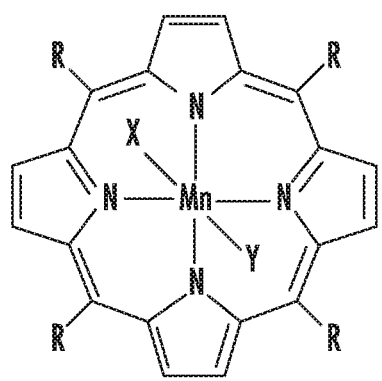
FIGS. 23A-23D illustrate examples of ligands that will assist C—H fluorination.
Figure 23B:
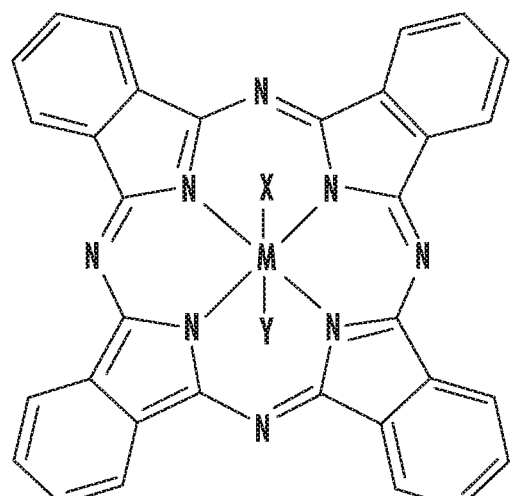
Figure 23C:
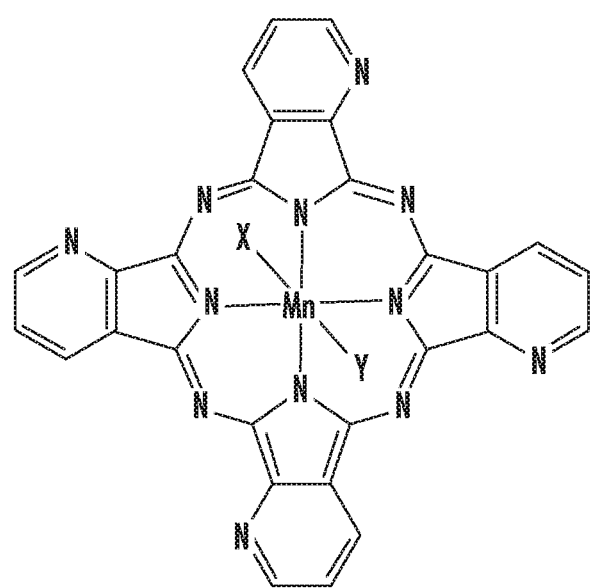
Figure 23D:
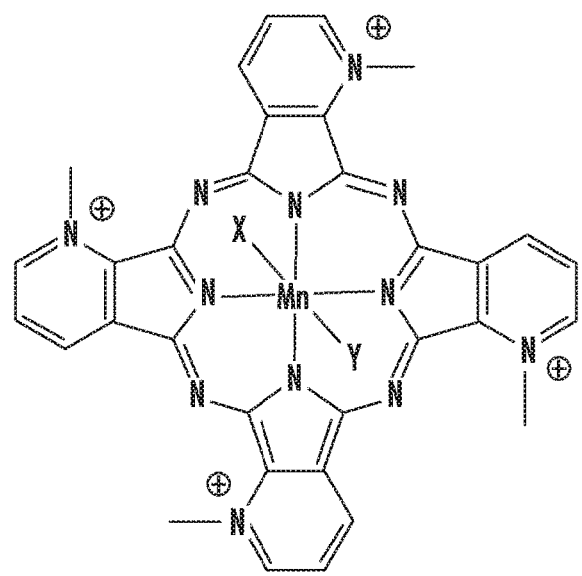

Additional halogenating catalysts may include additional metal ligand complexes. Referring to FIGS. 23A-23D, examples of ligands hat will assist C—H fluorination are illustrated. Referring to FIG. 23A, a porphyrin is illustrated. Referring to FIG. 23B a phthalocyanine is illustrated. Referring to FIG. 23C, a porphyrazine is illustrated. Referring to FIG. 23D, a tetra-N-methyl-tetra-2-pyridoporphyrazine is illustrated.

Figure 24A:
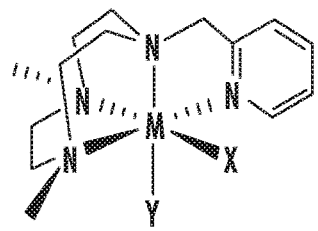
FIGS. 24A-24G illustrate examples of ligands that will assist oxidative C—H fluorination.
Figure 24B:
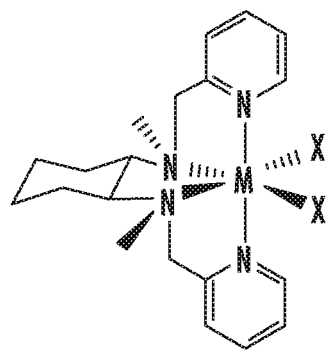
Figure 24C:
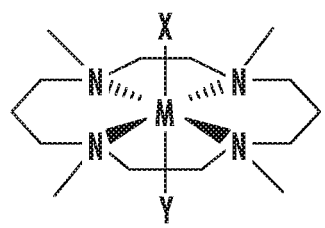
Figure 24D:
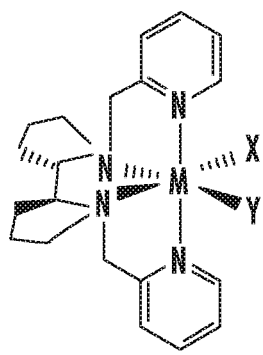
Figure 24E:
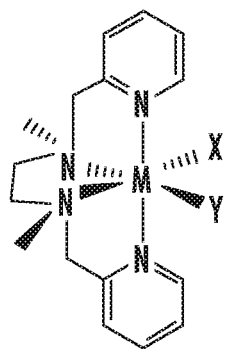
Figure 24F:
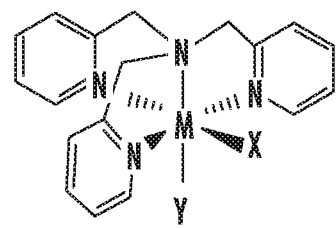
Figure 24G:
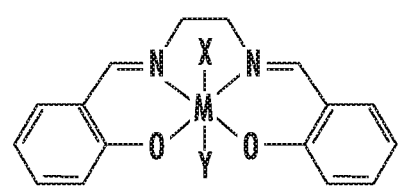

Further examples of ligands that may assist oxidative C—H fluorination are illustrated in FIGS. 24A-24G. Referring to FIG. 24A an N-pyridylmethyl-tri-aza-cyclononane is illustrated. Referring to FIG. 24B, an N,N-dipyridylmethyl cyclohexadiamine is illustrated. Referring to FIG. 24C, a tetra-aza-cyclotetra-decane is illustrated. Referring to FIG. 24D, an N,N-dipyridylmethyl 2,2'-dipyrrolidine is illustrated. Referring to FIG. 24E, an N,N-dipyridylmethyl ethylenediamine is illustrated. Referring to FIG. 24F, a tripyridyl amine (TPA). Referring to FIG. 24G, salen is illustrated. Any one or more of the ligands in FIGS. 23A-24G, along with a metal, may be provided as a fluorinating catalyst.

Figure 30:
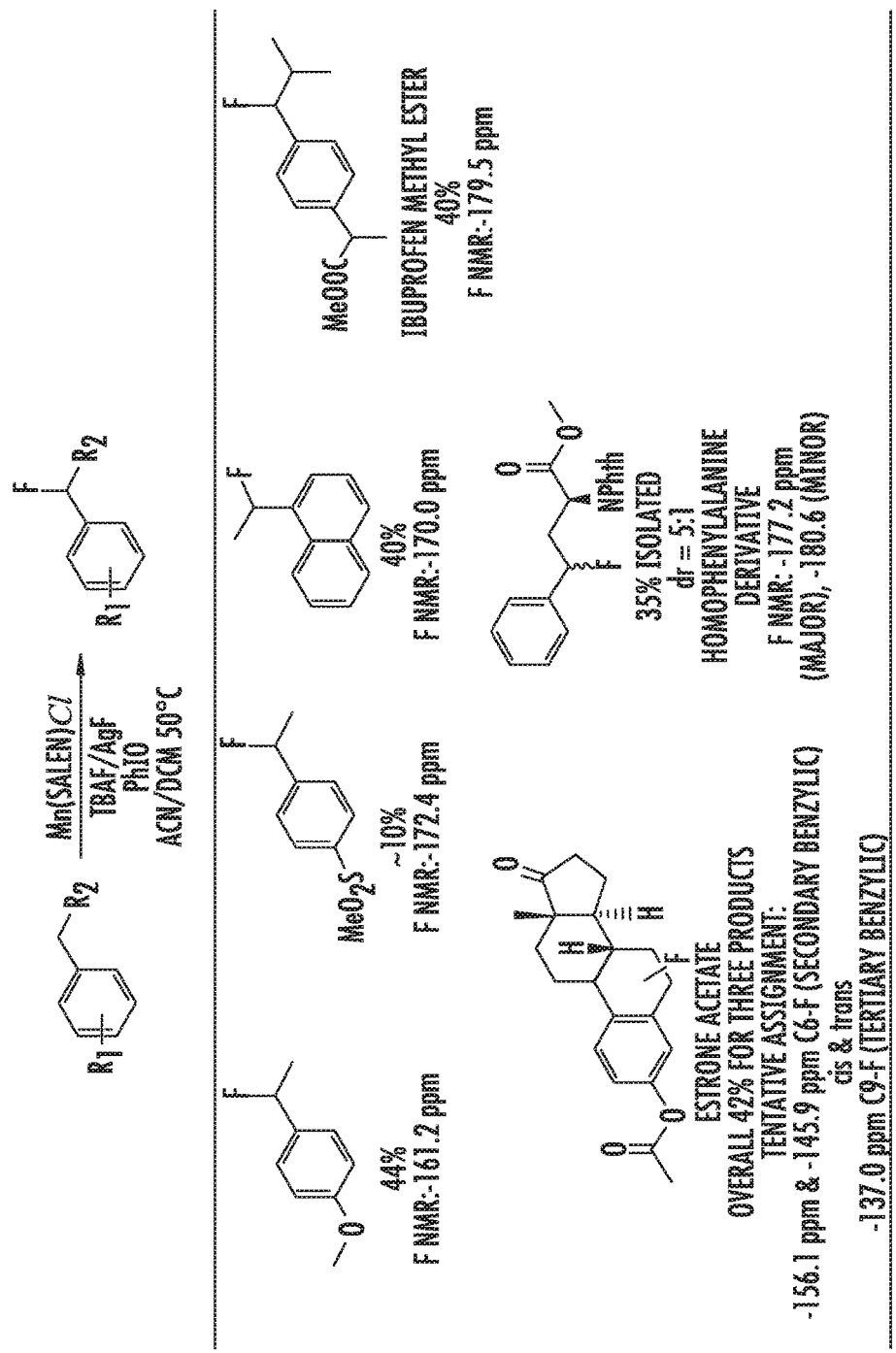
FIG. 30 illustrates manganese salen catalyzed benzylic C—H fluorination.
Figure 31:
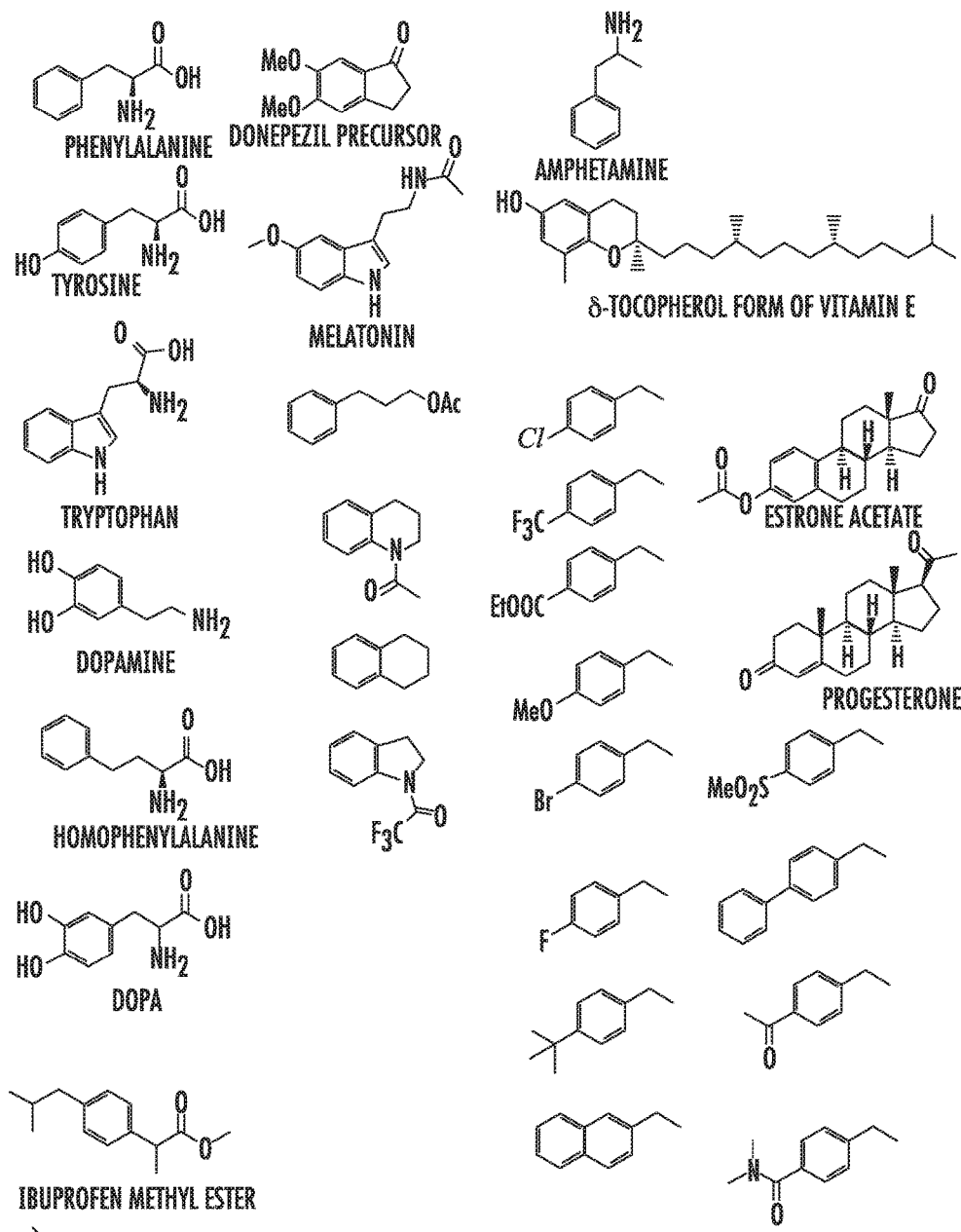
FIG. 31 illustrates potential manganese salen catalyzed benzylic C—H fluorination substrates.
Figure 32:
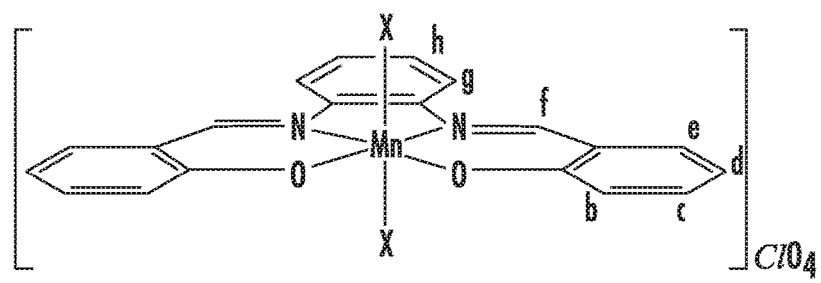
FIG. 32 illustrates a manganese salophen complex.
Figure 33:
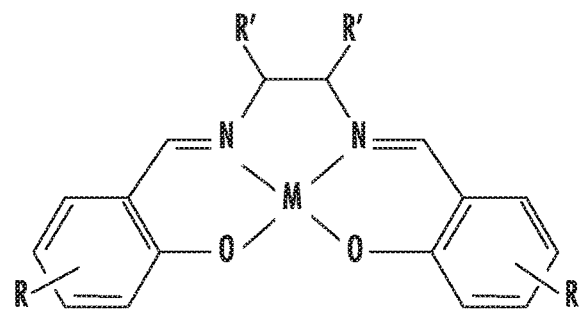
FIG. 33 illustrates a manganese salen complex.

Salen, salophen, phthalocyanine and porphyrazine ligands for manganese may also be used as a fluorinating catalyst. It was found that in the presence of a manganese salen (FIG. 29) species as the catalyst, different substrates with benzylic protons can be selectively fluorinated. Substrates that have been tested so far are illustrated in FIG. 30. Substrates that are likely to work by analogy are illustrated in FIG. 31. Reactions were run as described for the manganese porphyrin catalyst just substituting the manganese salen catalyst. Generalized ligand structures are illustrated in FIGS. 32 and 33. Referring to FIG. 32, a manganese salophen complex is illustrated. Axial ligands and the counter ion can typically be halide, acetate (or other carboxylic acids), perchlorate, etc. Typical substitutions at carbons b-h can be alkyl, aryl or halogen. Substituents could also be carboxylate, sulfonate or trialkylammonium to afford higher solubility on polar solvents such as water. Referring to FIG. 33, manganese salen complex (M=Mn) is illustrated. Typical substituent groups can be alkyl, such as t-butyl, or aryl, such as phenyl, or halide. The groups R' can be alkyl or aryl, such as phenyl, in either the cis or trans stereochemical arrangement. The two R' groups together with the ethano group can form a cycloalkyl substituent such as cyclopentyl or cyclohxyl. The ring fusion in such cases can be cis or trans.

Figure 34:
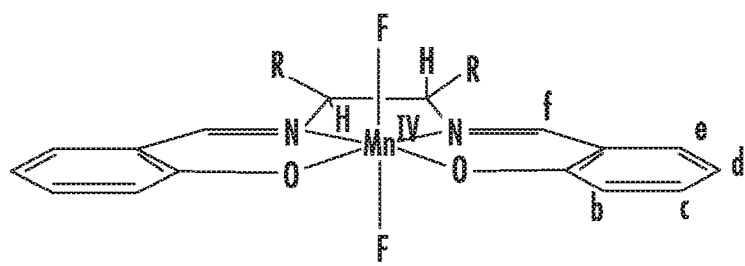
FIG. 34 illustrates trans-difluoro-manganese(IV) salen complexes.
Figure 35:
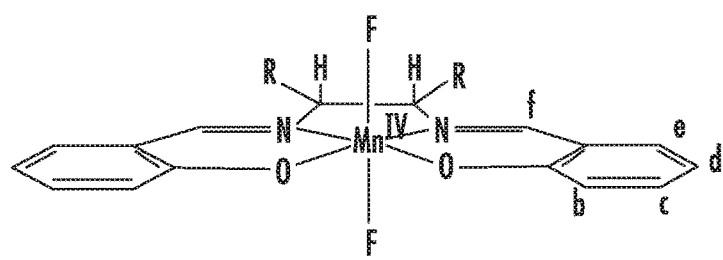
FIG. 35 illustrates trans-difluoro-manganese(IV) salen complexes.
Figure 36:
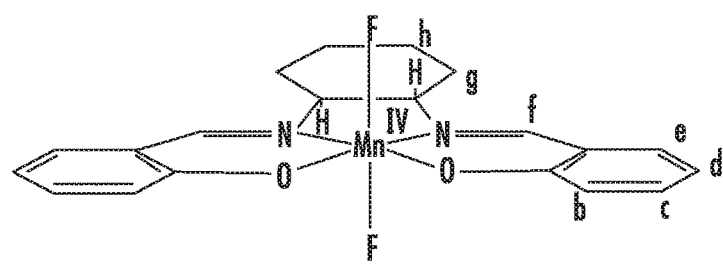
FIG. 36 illustrates trans-difluoro-manganese(IV) cyclohxyl-salen.
Figure 37:
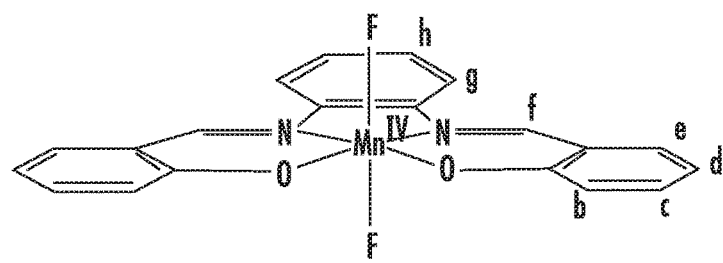
FIG. 37 illustrates trans-difluoro-manganese(IV) salophen complexes.

Referring to FIGS. 34-37, trans-difluoro-manganese(IV) complexes for C—H fluorination are illustrated. Referring to FIG. 34, trans-difluoro-manganese(IV) Salen complexes are illustrated where R can be alkyl or aryl, and b-f can be alkyl, aryl or halogen. Referring to FIG. 35, trans-difluoro-manganese(IV) Salen complexes are illustrated where R can be alkyl or aryl, and b-f can be alkyl, aryl or halogen. Referring to FIG. 36, trans-difluoro-manganese(IV) cyclohxyl-salen is illustrated where b-f can be alkyl, aryl or halogen. Referring to FIG. 37, trans-difluoro-manganese(IV) salophen complexes are illustrated, where b-h can be alkyl, aryl or halogen.

Example 30—Additional Substrates

Figure 38:
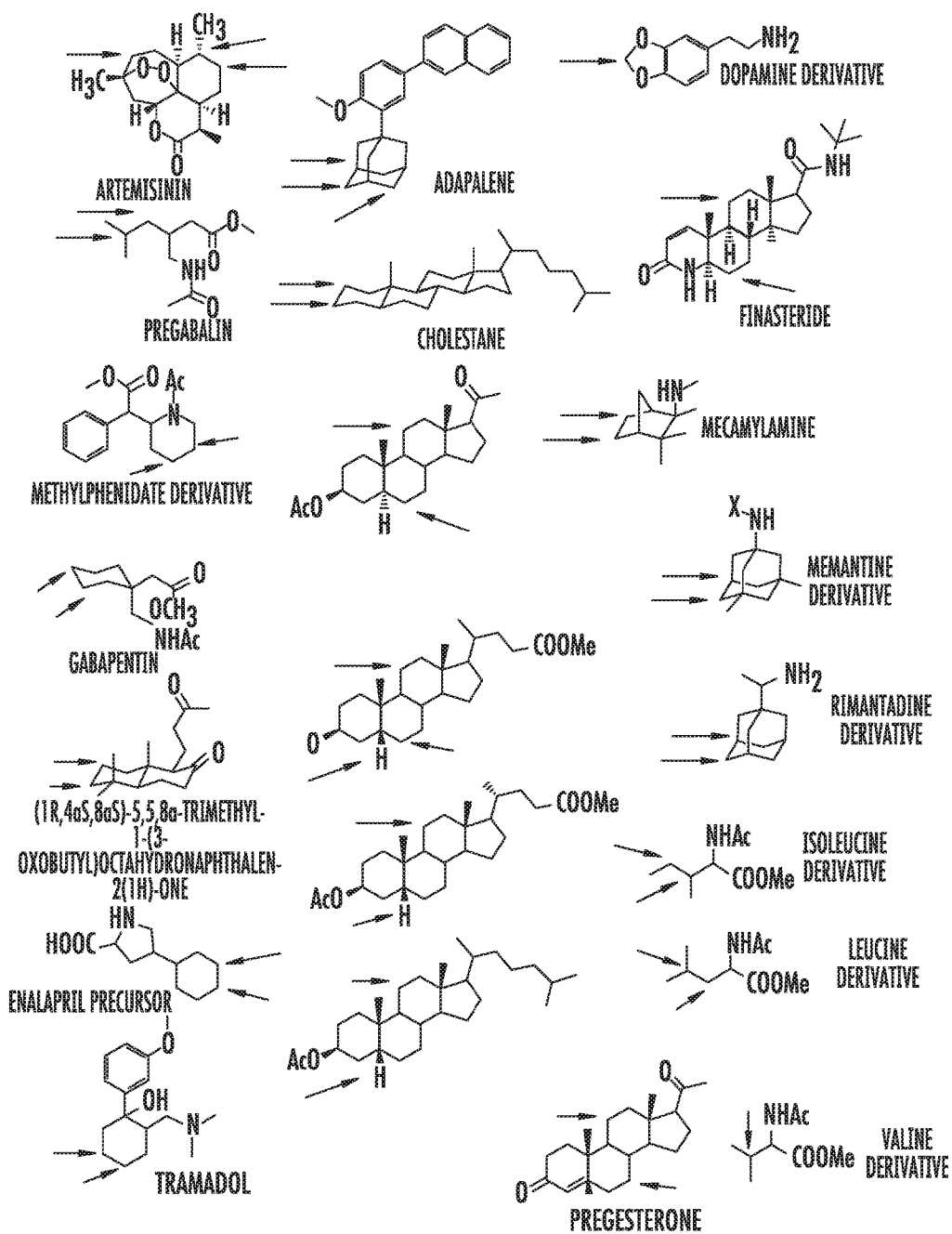
FIG. 38 illustrates exemplary substrates that may be used in any method contained herein.
Figure 39:
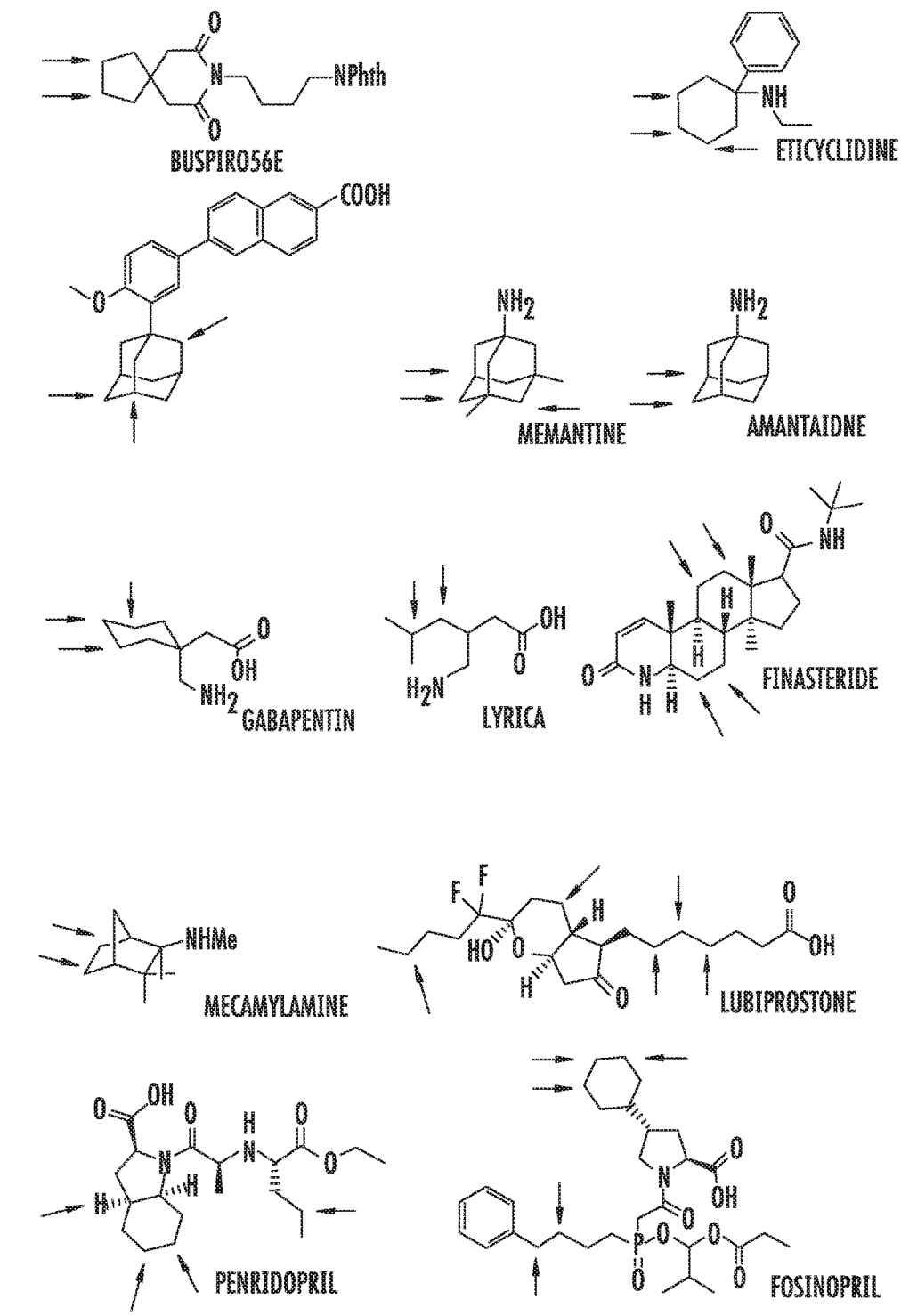
FIG. 39 illustrates exemplary substrates that may be used in any method contained herein.

Referring to FIGS. 38 and 39, additional substrates are illustrated that may be used in any method contained herein in the form illustrated, or as an analog thereof.

As used herein, a carbon containing compound may also be referred to as a target or substrate. As used herein, an analog of a carbon containing compound refers to a compound of a similar structure and/or ring system in which one or several atoms or substituents are substituted for atoms or substituents in the parent structure but retaining the overall shape of the molecule. In some aspects, an analog may bind to the same biological target and exert a similar biological activity.

Example 31—Additional Ligands

The phenyl substituent in a tetraphenyl or tetramesityl porphyrin herein could be naphthyl, and these aryl groups could also have -ethyl, trifluoromethyl, halogen or -nitro substituents attached to the phenyl or aryl groups.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

Any single embodiment herein may be supplemented with one or more element from any one or more other embodiment herein.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of halogenating a carbon containing compound having an sp3 C—H bond, the method comprising:
    combining the carbon containing compound, a halogenating agent comprising a halogen, a halogenating catalyst, and a phase transfer catalyst, wherein
    the halogenating catalyst is a manganese phthalocyanine, a manganese porphyrin, a manganese salophen, or a manganese porphyrazine and is present in a OH—Mn(IV)-L intermediate, where L is O, OH, or OX and X is a halide, after the step of combining, the halogenating agent is present in an amount of 1-10 equivalents based the amount of carbon containing compound, and the halogenating agent is selected from the group consisting of hypohalites, N-chlorosuccinimide (NCS), N-bromosuccinimide, hypochlorites, NaOCl, NaOBr, and calcium hypochlorite, and
    the halogen replaces the hydrogen in the sp3 C—H bond.

2. The method of claim 1, wherein the carbon containing compound is added in a concentration from 1 mM to 1 M, the halogenating agent is added in a concentration from 1 mM to 3 M, the halogenating catalyst is added in a concentration from 1 to 20 mole percent, and the phase transfer catalyst is added in a concentration from 1 to 20 mole percent.

3. The method of claim 1, further comprising allowing the carbon containing compound, the halogenating agent, the halogenating catalyst, and the phase transfer catalyst to react for 30 minutes to 12 hours.

4. The method of claim 1, further comprising maintaining the carbon containing compound, the halogenating agent, the halogenating catalyst, and the phase transfer catalyst at a temperature from 0° C. to 80° C.

5. The method of claim 1, wherein combining further comprises:
    mixing the phase transfer catalyst, the halogenating catalyst and the carbon containing compound in a solvent to form a first mixture; and
    adding the halogenating agent to the first mixture to form a second mixture.

6. The method of claim 5, further comprising providing an inert gas over at least one of the first mixture or the second mixture.

7. The method of claim 6, wherein the inert gas is N2.

8. The method of claim 5, wherein the solvent is at least one selected from the group consisting of dichloromethane, dichlorobenzene, acetonitrile and 1,2-dichloroethane.

9. The method of claim 1, wherein the carbon containing compound is selected from the group consisting of neopentane; toluene; cyclohexane; norcarane; trans-decalin; 5a-cholestane; sclareolide; 1, 3, 5(10)-estratrien-17-one; (1R, 4aS, 8aS)-octahydro-5,5,8a-trimethyl-1-(3-oxobutyl)-napthalenone; (1R, 4S, 6S, 10S)-4, 12, 12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholestane; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R, 4aS, 8aS)-5, 5, 8a-trimethyl-1-(3-oxobutyl)octahydronaphthalen-2(1H)-one; phenylalanine; donepezil precursor; amphetamine; 6-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; and cyclohexane carboxylic acid methyl ester; or an analog of any one of the foregoing.

10. The method of claim 1, wherein the carbon containing compound is a drug or drug candidate precursor.

11. The method of claim 1, wherein the halogenating agent is the hypohalite, which is provided by setting conditions to produce a hypohalite in situ.

12. The method of claim 1, wherein the halogenating catalyst is selected from the group consisting of Mn(TPP)Cl, Mn (TMP)Cl, Mn [tetra-2,6-dichlorophenyl porphyrin], Mn [tetra-2-nitrophenyl porphyrin], Mn[tetra-2-naphthyl porphyrin], Mn[pentachlorophenyl porphyrin, Mn [tetraphenyl-2,3,7,8,12,13,17,18-octachloroporphyrin], Mn[tetraphenyl-2,3,7,8,12,13,17,18-octabromoporphyrin], and Mn[tetraphenyl-2,3,7,8,12,13,17,18-octanitroporphyrin].

13. The method of claim 1, wherein the phase transfer catalyst is selected from the group consisting of tetrabutylammonium chloride, tetraalkyl ammonium, mixed alkyl ammonium, aryl ammonium, benzyl-trimethylammonium chloride, benzalkonium chloride, benzyl tributylammonium chloride, benzyl triethylammonium chloride, tetrabutyl phosphonium chloride, tetramethyl phosphonium chloride, and dimethyldiphenyl phosphonium chloride.

14. The method of claim 1, wherein the halogenating agent is the hypohalite.

15. The method of claim 14, wherein the hypohalite has a pH of 11 prior to combining.

16. The method of claim 15, wherein after combining the halogenating catalyst comprises at least one axial ligand selected from O, OH, or OX, where X is a halide.

17. The method of claim 16, wherein the at least one axial ligand is OX and X is Cl.

18. The method of claim 17 further comprising monitoring reaction progress.

19. The method of claim 18 further comprising adding additional halogenating agent.

20. The method of claim 1, wherein after combining, the halogenating catalyst comprises at least one axial ligand selected from O, OH, or OX, where X is a halide.

21. The method of claim 20, wherein the at least one axial ligand is OX and X is Cl.

22. The method of claim 1, wherein the halogenating agent is present in an amount of 3 equivalents based the amount of carbon containing compound.

23. The method of claim 1, wherein the halogenating agent is the hypochlorite, which was provided by adding chlorine gas to a water solution of sodium or potassium hydroxide.

24. The method of claim 1, wherein the step of combining forms a mixture having an aqueous phase with a pH=12.

25. A method of fluorinating a carbon containing compound having an sp3 C—H bond, the method comprising:
conducting the method of claim 1 to replace the hydrogen of the sp3 C—H bond with Cl, Br, I or At;
obtaining a halogenated product; and
conducting nucleophilic substitution on the halogenated product with a fluorine source, wherein
the fluorine replaces the Cl, Br, I or At.

26. The method of claim 25, wherein the fluorine source is potassium fluoride.

27. The method of claim 26, wherein the step of nucleophilic substitution is conducted in the presence of a phase transfer catalyst.

28. The method of claim 25, wherein the carbon containing compound includes a compound selected from the group consisting of neopentane; toluene; cyclohexane; norcarane; trans-decalin; 5a-cholestane; sclareolide; 1, 3, 5(10)-estratrien-17-one; (1R, 4aS, 8aS)-octahydro-5,5,8a-trimethyl-1-(3-oxobutyl)-napthalenone; (1R, 4S, 6S, 10S)-4, 12, 12-trimethyl-tricyclo[8.2.0.04,6]dodecan-9-one; levomethorphan; lupine; 20-methyl-5alpha(H)-pregnane; isolongifolanone; caryophyllene acetate; N-acetyl-gabapentin methyl ester; acetyl-amantidine; phthalimido-amantadine; methyloctanoate; saturated fatty acid esters; N-acetyl-Lyrica methyl ester; artemisinin, adapalene; finasteride; N-acetyl-methylphenidate; mecamylamine; N-acetyl-mecamylamine; N-acetyl-memantine; phthalimidi-memantine; N-acetyl-enanapril precursor methyl ester; progesterone; artemisinin; adapalene; dopamine derivative; pregabalin; cholestane; finasteride; methylphenidate derivative; mecamylamine; gabapentin; memantine derivative; gabapentin; rimantadine derivative; isoleucine derivative; leucine derivative; valine derivative; pregesterone; tramadol; enalapril precursor; (1R, 4aS, 8aS)-5, 5, 8a-trimethyl-1-(3-oxobutyl)octahydronaphthalen-2(1H)-one; phenylalanine; donepezil precursor; amphetamine; 6-tocopherol form of vitamin E; tyrosine; melatonin; tryptophan; estrone acetate; progesterone; dopamine; homophenylalanine; DOPA; ibuprofen methyl ester; buspirone; eticyclidine; memantine; amantadine; lyrica; lubiprostone; penridopril; fosinopril; N-Phth amantadine; N-Phth Memantine; 2-adamantanone; rimantadine analogue; adapalene precursor; perindopril precursor; protected gabapentin; methyl octanoate; methyl nonanate; methyl hexanoate; cyclohexyl acetate; and cyclohexane carboxylic acid methyl ester; or an analog of any one of the foregoing.

29. The method of claim 25, wherein the carbon containing compound is a drug or drug candidate precursor.

30. The method of claim 25, wherein the halogenating agent is the hypohalite, which is provided by setting conditions to produce a hypohalite in situ.

31. The method of claim 25, wherein the halogenating catalyst is selected from the group consisting of Mn(TPP)Cl, Mn (TMP)Cl, Mn[tetra-2,6-dichlorophenyl porphyrin], Mn[tetra-2-nitrophenyl porphyrin], Mn[tetra-2-naphthyl porphyrin], Mn[pentachlorophenyl porphyrin, Mn [tetraphenyl-2,3,7,8,12,13,17,18-octachloroporphyrin], Mn [tetraphenyl-2,3,7,8,12,13,17,18-octabromoporphyrin], Mn [tetraphenyl-2,3,7,8,12,13,17,18-octanitroporphyrin].

32. The method of claim 25, wherein the phase transfer catalyst includes a substance selected from the group consisting of tetrabutylammonium chloride, tetraalkyl ammonium, mixed alkyl ammonium, aryl ammonium, benzyltrimethylammonium chloride, benzalkonium chloride, benzyl tributylammonium chloride, benzyl triethylammonium chloride, tetrabutyl phosphonium chloride, tetramethyl phosphonium chloride, and dimethyldiphenyl phosphonium chloride.

33. The method of claim 25, wherein the halogenating agent is the hypochlorite, which was provided by adding chlorine gas to a water solution of sodium or potassium hydroxide.

34. The method of claim 25, wherein the step of combining forms a mixture having an aqueous phase with a pH=12.

35. The method of claim 25, wherein the step of conducting the method of claim 1 replaces the hydrogen of the sp3 C—H bond with Cl or Br.

36. A method of halogenating a carbon containing compound having an sp3 C—H bond, the method comprising:
combining the carbon containing compound, a halogenating agent comprising a halogen, a halogenating catalyst, and a phase transfer catalyst, wherein
the halogenating catalyst is a manganese phthalocyanine, a manganese porphyrin, a manganese salophen, or a manganese porphyrazine, and after combining the halogenating catalyst comprises at least one axial ligand selected from O, OH, or OX, where X is a halide, and
the halogenating agent is a hypohalite, and
the halogen replaces the hydrogen in the sp3 C—H bond.

37. The method of claim 36, wherein the hypohalite has a pH of 11 prior to combining.

38. The method of claim 36, wherein the halogenating catalyst is the manganese porphyrin.

39. The method of claim 38, wherein the hypohalite has a pH of 11 prior to combining.

40. The method of claim 36, wherein the halogenating catalyst is the manganese porphyrazine, and after combining comprises at least one axial ligand selected from OX, where X is a halide.

41. The method of claim 40, wherein the hypohalite has a pH of 11 prior to combining.

42. A method of fluorinating a carbon containing compound having an sp3 C—H bond comprising:
conducting the method of claim 36 to replace the hydrogen of the sp3 C—H bond with Cl, Br, I, or At; obtaining a halogenated product; and conducting nucleophilic substitution on the halogenated product with a fluorine source, wherein the fluorine replaces the Cl, Br, I, or At.

43. The method of claim 42, wherein the step of conducting the method of claim 36 replaces the hydrogen of the sp3 C—H bond with Cl or Br.

\* \* \* \* \*